(12) United States Patent
Zhang et al.

(10) Patent No.: US 9,211,310 B2
(45) Date of Patent: Dec. 15, 2015

(54) USE OF A CHINESE MEDICINE COMPOSITION IN PREPARING MEDICAMENTS FOR TREATING SECONDARY PREVENTION OF MYOCARDIAL INFARCTION

(75) Inventors: Boli Zhang, Tianjin (CN); Hongcai Shang, Tianjin (CN); Chen Yao, Tianjin (CN); Baoyan Liu, Tianjin (CN); Weiliang Weng, Tianjin (CN); Yuxia Zhao, Tianjin (CN); Guohua Dai, Tianjin (CN); Xiumei Gao, Tianjin (CN); Ming Ren, Tianjin (CN); Junhua Zhang, Tianjin (CN); Hongbo Cao, Tianjin (CN); Jingyuan Mao, Tianjin (CN); Xuejun Hu, Tianjin (CN); Zhisheng Jin, Tianjin (CN); Junping Zhang, Tianjin (CN); Yiyu Cheng, Tianjin (CN); Xijun Yan, Tianjin (CN); Jiazhen Qu, Tianjin (CN); Hui Wang, Tianjin (CN); Hongjuan Xu, Tianjin (CN); Wenke Zheng, Tianjin (CN)

(73) Assignee: TASLY PHARMACEUTICAL GROUP CO., LTD, Tianjin (CN)

( * ) Notice: Subject to any disclaimer, the term of this patent is extended or adjusted under 35 U.S.C. 154(b) by 380 days.

(21) Appl. No.: 13/807,500

(22) PCT Filed: Jun. 28, 2011

(86) PCT No.: PCT/CN2011/076499
§ 371 (c)(1),
(2), (4) Date: Jan. 22, 2013

(87) PCT Pub. No.: WO2012/000425
PCT Pub. Date: Jan. 5, 2012

(65) Prior Publication Data
US 2013/0209590 A1 Aug. 15, 2013

(30) Foreign Application Priority Data
Jun. 28, 2010 (CN) .......................... 2010 1 0219730

(51) Int. Cl.
| A61K 36/00 | (2006.01) |
| A61K 36/537 | (2006.01) |
| A61K 36/482 | (2006.01) |
| A61K 36/258 | (2006.01) |
| A61K 36/48 | (2006.01) |
| A61K 36/481 | (2006.01) |

(52) U.S. Cl.
CPC ............ *A61K 36/537* (2013.01); *A61K 36/258* (2013.01); *A61K 36/48* (2013.01); *A61K 36/481* (2013.01)

(58) Field of Classification Search
None
See application file for complete search history.

(56) References Cited

U.S. PATENT DOCUMENTS

| 7,438,935 B2 | 10/2008 | Wei et al. | |
| 2007/0053999 A1* | 3/2007 | Wei et al. | ...................... 424/728 |

FOREIGN PATENT DOCUMENTS

| CN | 1375316 | 10/2002 | ................ A61P 9/10 |
| CN | 1861114 | 11/2006 | ........... A61K 36/537 |
| CN | 101239099 A | 8/2008 | |
| CN | 101450106 | 6/2009 | ........... A61K 36/537 |
| CN | 101507765 A | 8/2009 | |
| EP | 1 741 439 A1 | 10/2007 | |

OTHER PUBLICATIONS

Stryuk et al, "Internal Diseases," *Univeristy Textbook Moscow*, GEOTAR-Media Publishers 2008, pp. 81-83 (w/English Abstract) (3 pages).
Database TCM [Online] SIPO; Dec. 30, 2009, Zhai Xiuxiang: "A medicine for treating coronary heart disease", XP002716281,; & CN 101 612 349 A (Xiuxiang Zhai) Dec. 30, 2009.
Database TCM [Online] Jun. 10, 2009, Cheng Yiyu et al.: "A Chinese medicine composition with vascularization of ischemic cardiac muscle promoting effect", XP002716282,; & CN 101 450 106 A (Univ Zhejiang [CN]) Jun. 10, 2009.
Database TCM [Online] SIPO; Oct. 26, 2005, Zhao Hongwei: "A Chinese patent medicine for the prevention and treatment of apoplexy",XP002716303,; & CN 1 686 510 A (Zhao Hongwei [CN] Oct. 26, 2005.
Database WPI Week 200863 Thomson Scientific, London, GB; AN 2008-K46820 XP002716304, &CN 101 049 462 A (Beijing Increase Biological Prod Res Inst) Oct. 10, 2007.
Database WPI Week 200968 Thomson Scientific, London, GB; AN 2009-P08794 XP002716305, Cheng X. et al.: & CN 101 530 467 A (Ianjin Tianshili Medicine MFR Co Ltd) Sep. 16, 2009.
Database TCM [Online] SIPO; Aug. 29, 2001, Zheng Guopeng: "A traditional Chinese medicine for the treatment of coronary heart disease", XP002716306,; & CN 1 309 991 A (Zheng Guopeng [CN]) Aug. 29, 2001.
Xiang, Y. et al. "Secondary Prevention of Myocardial Infarction and Applicable Prospect of Traditional Chinese Medicine." Medical Recapitulate. vol. 13, No. 34, Feb. 2007 (3 pages).
Xie, D. et al. "Clinical Observation of the Effects of QSYQ Drop Pills on Secondary Treatment of Coronary Heart Disease." Chinese Journal of Information on Traditional Chinese Medicine. vol. 15, No. 8, Aug. 2008 (1 page).
Yan, F. et al. "Effects of QSYQ Drop Pills on Secondary Treatment of Myocardial Infarction and the Mechanism." Chinese Doctoral Dissertations Full-text Database Medicine and Health Sciences. No. 12, Dec. 2008 (153 pages).

(Continued)

*Primary Examiner* — Qiuwen Mi
(74) *Attorney, Agent, or Firm* — Nixon Peabody LLP

(57) ABSTRACT

The present invention relates to a use of Chinese medicine composition in preparation of medicine for secondary prevention of myocardial infarction. Said Chinese medicine composition is prepared from a formula comprising the crude drugs by the following weight percentages: Radix Astragali 22.2%~66.8%, Radix Salviae Miltiorrhizae 11.6%~33.4%, Radix Notoginseng 2.5%~13.5%, and Lignum Dalbergiae Odoriferae 14.5%~44.3%.

19 Claims, 8 Drawing Sheets

(56) References Cited

OTHER PUBLICATIONS

Figure 1:
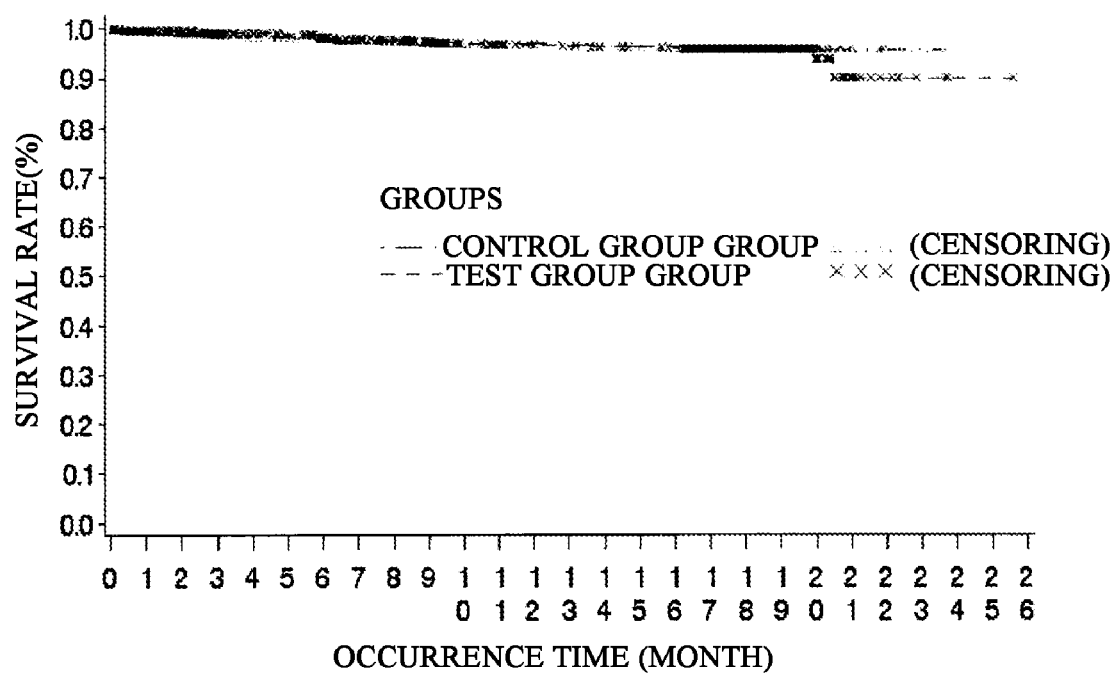

International Search Report mailed Oct. 13, 2011 which issued in corresponding International Patent Application No. PCT/CN2011/076499 (12 pages).

Written Opinion mailed Oct. 13, 2011 which issued in corresponding International Patent Application No. PCT/CN2011/076499 (8 pages).

Jiquin et al., "Formulas of Traditional Chinese Medicine," Shanghai Science and Technology Press, 1983, p. 8.

* cited by examiner

USE OF A CHINESE MEDICINE COMPOSITION IN PREPARING MEDICAMENTS FOR TREATING SECONDARY PREVENTION OF MYOCARDIAL INFARCTION

CROSS-REFERENCE TO RELATED APPLICATIONS

This application is a U.S. national stage of International Patent Application No. PCT/CN2011/076499, filed Jun. 28, 2011, which claims priority of Chinese Patent Application No. 201010219730.2, filed on Jun. 28, 2010, the contents of which are each incorporated herein by reference in its entirety.

FIELD OF THE INVENTION

The present invention relates to the field of medicine, in particular to a use of Chinese medicine composition in preparing medicaments for treating secondary prevention of myocardial infarction.

BACKGROUND OF THE INVENTION

Cardiovascular disease is a common and frequent disease, threatening human life and health seriously. Annually, there are about 20 million persons dying of acute cardiovascular events worldwide, and more than half of them died of acute myocardial infarction (AMI). With population aging in China, the incidence of AMI showed a clear upward trend, which has been already close to the international average level. In recent years, raised monitoring and treating level has lowered the mortality of myocardial infarction. But the survivals are still at a high risk of reoccurrence of acute cardiovascular events, e.g. the myocardial infarction, congestive heart failure and sudden death etc. Accordingly, except active treatment in acute phase, the secondary prevention of myocardial infarction should be strengthened.

The secondary prevention of myocardial infarction refers to the prevention of cardiovascular events and improvement patients' life quality after occurrence of myocardial infarction. As shown by many studies, there are a lot of drugs reported to have an active and positive effect on long-term secondary prevention of myocardial infarction, e.g. platelet inhibitors (aspirine), β-receptor blockers, statins and angiotensin converting enzyme inhibitors (ACEI) etc. In addition, efficacy of these drugs are not influenced by patients' other conditions, such as age and gender etc.

As confirmed by a large-scale medicine clinical trial results, although afore-mentioned drugs, e.g. platelet inhibitors (aspirine), β-receptor blockers, statins and angiotensin converting enzyme inhibitors (ACEI) etc can significantly decrease the mortality rate caused by AMI, a great many survivals are usually led to disability or death due to the cardiovascular events, such as re-infarction, severe arrhythmia and heart failure etc. Moreover, these drugs more or less have some adverse reactions, some of which are even very serious. In addition to this, some westerners became gradually aware of that the effect of single drug on secondary prevention may not be as good as that of combined drugs, and developed a series of compound western medicine preparations for secondary prevention of myocardial infarction. In fact, herbal prescriptions have been mainly used for treating disease in Traditional Chinese Medicine (TCM) for thousands of years. Even a single herb medicine can be considered as a small compound prescription, because it contains complicated ingredients. Besides, the TCM prescriptions have the advantages of eased efficacy, attenuated toxicity and increased effect by drug compatibility and reduced side effect, which is accordingly suitable for long-term administration as secondary prevention medicine.

SUMMARY OF THE INVENTION

Objective of present invention is to provide a use of Chinese medicine composition in preparing medicaments for treating secondary prevention of myocardial infarction. Said Chinese medicine composition is prepared from a formula comprising the crude drugs by the following weight percentages:

| | |
|---|---|
| Radix Astragali (Huangqi in TCM) | 22.2%-66.8%, |
| Radix Salviae Miltiorrhizae (Danshen) | 11.6%-33.4%, |
| Radix Notoginseng (Sanqi) | 2.5%-13.5%, and |
| Lignum Dalbergiae Odoriferae (Jiangxiang) | 14.5%-44.3%. |

According to the present invention, said Chinese medicine composition has effects of decreasing the occurrence of cardiovascular events in patients after acute myocardial infarction. Said cardiovascular events include following diseases: a). re-infarction; b). severe arrhythmia; c). heart failure; d). Cardiogenic shock; e). revascularization (interventional therapy and coronary artery bypass grafting).

According to the present invention, said Chinese medicine composition has effects of decreasing the occurrence of non-cardiovascular events in patients after acute myocardial infarction. Said non-cardiovascular events include following diseases: a). stroke; b) pulmonary embolism; c). peripheral vascular events; d). tumor.

According to the present invention, said Chinese medicine composition has effects of decreasing the occurrence of death events in patients after acute myocardial infarction. Said death events include following ones: a). coronary heart disease (CHD) death; b). other cardiovascular death; c). non-cardiovascular disease death.

According to the present invention, said Chinese medicine composition can alleviate the attack of angina pectoris in patients after acute cardiovascular infarction, e.g. reducing the frequency of attack, shortening the duration, relieving pain degree, decreasing the dose of nitroglycerin and improving the symptoms of chest pain, chest tightness, short breath, fatigue, palpitation, spontaneous perspiration as well as pale complexion.

According to the present invention, said Chinese medicine composition can improve life quality in patients after acute myocardial infarction. After use of said Chinese medicine composition, the limitation degree of physical activity, steady status of angina pectoris and attack frequency of angina pectoris are significantly ameliorated.

According to the present invention, said Chinese medicine composition is preferably prepared from a formula comprising the crude drugs by weight percentages:

| | |
|---|---|
| Radix Astragali (Huangqi) | 30.8%-57.2% |
| Radix Salviae Miltiorrhizae (Danshen) | 15.4%-28.6% |
| Radix Notoginseng (Sanqi) | 3.5%-6.5%, and |
| Lignum Dalbergiae Odoriferae (Jiangxiang) | 20.6%-38.2%. |
| Most preferably, | |
| Radix Astragali (Huangqi) | 44.7%, |
| Radix Salviae Miltiorrhizae (Danshen) | 26.7%, |

| | |
|---|---|
| Radix Notoginseng (Sanqi) | 6.3%, and |
| Lignum Dalbergiae Odoriferae (Jiangxiang) | 22.3%. |
| Or, | |
| Radix Astragali (Huangqi) | 41.2%, |
| Radix Salviae Miltiorrhizae (Danshen) | 23.8%, |
| Radix Notoginseng (Sanqi) | 4.5%, and |
| Lignum Dalbergiae Odoriferae (Jiangxiang) | 30.5%. |

According to the present invention, said Chinese medicine composition can be prepared by extracting the individual crude drug in accordance with conventional extraction methods or the ones known in the prior art and mixing. Preferably, said Chinese medicine composition is prepared by a method comprising: extracting pulverized Sanqi and Danshen with water, filtering, properly concentrating the filtrate, performing alcohol precipitation, recovering the obtained supernatant and concentrating continuously to give an extract, namely Danshen & Sanqi extract; extracting pulverized Huangqi with water, filtering, properly concentrating the filtrate, performing alcohol precipitation, recovering the obtained supernatant and concentrating continuously to give an extract, namely Huangqi extract; reflux extracting Jiangxiang with water and collecting volatile oil; mixing well aforesaid two extracts, volatile oil and excipients to prepare into any one of pharmaceutically acceptable dosage forms, preferably dripping pill. Furthermore, the dripping pill is prepared by following steps: providing aforesaid Danshen & Sanqi extract, Huangqi extract and PEG-6000 with 2~5 times the total weight of extracts, dissolving on water bath to mix well, adding the Jiangxiang volatile oil and harmonizing to prepare the dripping pills by a conventional method. Likewise, the tablet can be obtained by a conventional method.

In order to better understand the present invention, a multi-center, randomized, double-blind, double-dummy and positive drug controlled trial had been conducted. 3508 patients who were in accordance with the diagnostic standards of AMI for 28 days to 2 years and differentiated as Qi deficiency and blood stagnation syndrome by TCM were studied. 0.5 g Chinese medicine composition prepared by the method of EXAMPLE 1 (Coded as QSYQ) was administrated half an hour after meal, 3 times per day. Aspirine was used as a positive drug. The patients were treated for 1 year and observed for 6 months. As shown in the results, there was no statistical difference in non-fatal re-infarction, non-fatal stroke, cardiovascular deaths in patients after acute myocardial infarction between the Qi Shen Yi Qi dripping pill (prepared in accordance with the present invention) and aspirine (log-rank test used for inter-group comparison). Moreover, as compared with the aspirine, no statistical difference had been found in decreasing the incidence of end point of death, reducing the severity score, frequency and duration of angina pectoris, lowering nitroglycerin dose, improving a series of TCM symptoms, e.g. chest tightness, palpitation, spontaneous perspiration, pale complexion as well life quality (Seattle Angina Questionnaire (SAQ) used). It is illustrated that the Chinese medicine composition of present invention has a similar effect with the aspirine on secondary prevention in patients after acute myocardial infarction.

ILLUSTRATION OF THE ABBREVIATION AND STATISTICS IN PRESENT INVENTION

AE Adverse Event
FAS Full Analysis Set
SS Safety Set
PP Per-Protocol, PP
LOCF Last Observation Carried Forward
PP Per Protocol
Mean Mean number
SD Standard Deviation
Median Median value
Min Minimum value
Max Maximum value
CI Confidence Interval
HR Hazard Ratio Aim of Study First of all, the aim of this trial was to investigate whether there was an effect on decreasing the hazard ratio (HR) of non-fatal re-infarction, cardiovascular deaths and non-fatal stroke after long-term administration of QSYQ, and whether there was non-inferiority, as compared with the aspirine. The second was to understand the effect of QSYQ on other clinical events and the life quality in patients.

General Design

A multi-center, double blind, double dummy, randomized and positive drug controlled clinical study was carried out.

A large-scale randomized controlled trials (RCT) method was used. The trial was carried out simultaneously in 16 sub-centers (grade class III hospitals) of clinical trial in 5 regions of East, West, South, North and central China and 84 hospitals.

Randomized Method: Centralized Randomization

According to the ready-made Random Sequence Table (that was generated by the computer), the subjects were randomly assigned into any one of two treating groups in a ratio of 1:1 via an Interactive Voice Response System (IVRS).

When the subjects met inclusion/exclusion criteria, researchers called the IVRS, and the IVRS would assign a subject with a specific identification code and random number. The specific identification code and random number assigned by IVRS were unique. They were used to represent the subjects' identification and which drug the subjects received.

In order to achieve the purpose of double blind in this trial, a placebo of QSYQ had been developed. It was required that it should have the same packaging and essentially consistent appearance, shape and color with the QSYQ. Likewise, the placebo of aspirine tablet had the same packaging and essentially consistent appearance, shape and color with the aspirine. For each subject, one-month dosage was packaged into a small box, containing QSYQ and the placebo of aspirine or aspirine and the placebo of QSYQ. Three-month dosage was packaged into a large box and each medicine had a same number.

The unique numbers were pre-printed on the study medicine labels. Through the IVRS, the medicines were randomly assigned to the subjects who met the requirements. Said labels were divided into two parts: the part that was pasted on the box was to describe how to use the medicine and other information; the removable part was torn off and pasted on the Drug Distribution Table. In addition, the drug assigners should record the medicine number of each observation on the Drug Distribution Diary.

Positive Control Drug

The aspirine (AS) was used as a routine drug for secondary prevention of myocardial infarction.

Administration Method

1. QSYQ treating group: QSYQ 0.5 g, tid, administrated half an hour post meal, taken 100 mg placebo of enteric coated aspirine tablet (4 tablets) at the same time, once a day.

2. Aspirine control group: 100 mg enteric coated aspirine tablet (4 tablets), administrated half an hour post meal, once a day, taken 0.5 g placebo of QSYQ at the same time, tid.

Calculation of Sample Size

Sample size was calculated on the following assumptions. According to the previous clinical experience, the incidence of MI (myocardial infarction) within 1 year was about 5%. Assuming that the treatment could reduce the death risk to 50% (namely the HR was 0.5), the dropping rate 20%, at least total number of 3000 study subjects were required (trial group: 1800 cases, power=90%, bilateral alpha=0.05). The research time was 18 months, the first 12 months of which was the treatment period and later 6 months the follow-up period.

Evaluation Index

I.1 Definition of Index

I.1.1 Endpoint Events (1) Cardiovascular events include a. Re-infarction, b. Severe arrhythmia, c. Heart failure, d. Cardiogenic shock, e. Revascularization (Interventional Therapy and coronary artery bypass grafting).

(2) Non-cardiovascular events include a. Stroke, b Pulmonary Embolism, c. Peripheral Vascular events, d. tumor.

(3) Death events include a. Coronary heart disease death, b. other cardiovascular death, c. non-cardiovascular death.

I.1.2 Score of Angina Pectoris and TCM Symptom

I.2 Treatment Standard

Treatment standard was divided into 4 grades. The first grade standard belonged to the primary endpoint event, and the second, third and fourth grades to the secondary endpoint event.

The $1^{st}$ grade included the non-fatal re-infarction, non-fatal stroke and cardiovascular deaths.

The $2^{nd}$ grade included the severe arrhythmia, heart failure, cardiogenic shock and revascularization.

The $3^{rd}$ grade included the peripheral vascular events, pulmonary embolism and non-cardiovascular deaths.

The $4^{th}$ grade included the angina pectoris, TCM symptoms and SAQ.

The primary endpoint of this study was the incidence of endpoint events within 1 year from the first administration of medicine. The dropout subjects (e.g. revoked informed consent or out of follow-up) were removed in the last assessment. The endpoint of the study was 1 year after the last subject was randomly assigned into group (12 months).

I.2.1 Main Indexes for Therapeutic Effects

Incidence of Main Endpoint Events

The main endpoint events were defined as the first grade endpoint events, including non-fatal re-infarction, non-fatal stroke and cardiovascular death. As long as any one of the events occurred, it was regarded as occurrence of the main endpoint event. Other cases could be deleted.

|  | Standard of symptom score |
|---|---|
| Angina pectoris | |
| Frequency | 0 score: None; 2 score: 2~6 times a week; 4 score: 1~3 times a day; 6 score: 4 times or more a day. |
| Duration | 0 score: None; 2 score: duration of pain for each time ≤5 min; 4 score: 5-10 min; 6 score: ≥10 min. |
| Pain degree | 0 score: none; 2 score: attack was ameliorated after rest, and daily life not affected; 4 score: attack was treated with drug, and normal activity continued after remission; 6 score: daily activity was affected by frequent attacks (onset of symptoms could be induced by e.g. dressing, eating, walking, stool). |
| Dose of nitroglycerin | 0 score: none; 2 score: 1~4 tablets a week; 4 score: 5~9 tablets a week; 6 score: 10 tablets or more a week. |
| TCM symptoms | |
| Chest pain | 0score: none; 3 score: attack was ameliorated after rest, and daily life not affected; 6 score: attack was treated with drug, and normal activity continued after remission; 9 score: daily activity was affected by frequent attacks (onset of symptoms could be induced by e.g. dressing, eating, walking, stool). |
| Chest tightness | 0 score: none; 3 score: chest tightness was felt occasionally, which could be self relieved; 6 score: chest tightness attacked frequently, but didn't affect the nomal life and work; 9 score: chest tightness could not be relieved, and affected the normal life and work. |
| Short breath | 0 score: none; 2 score: short breath after activity; 4 score: short breath after slight activity; 6 score: short breath felt usually. |
| Fatigue | 0 score: none; 2 score: fatigue was felt after severe activity; 4 score: fatigue was felt after middle activity; 6 score: fatigue was felt after slight activity. |
| Palpitation | 0 score: none; 1 score: sporadic palpitation could be self relieved; 2 score: palpitation frequently attacked, but could continue working; 3 score: sustained palpitation could not be relieved, and affected the life and work. |
| spontaneous perspiration | 0 score: none; 1 score: occasional perspiration after activity; 2 score: apparent perspiration after activity; 3 score: often perspiration when taking rest. |
| pale complexion | 0 score: none; 1 score: pale complexion. |

I.1.3 Life Quality

There were 19 questions in the Seattle angina questionnaire (SAQ), including 5 parts: physical limitation (PL), anginal stability (AS), anginal frequency (AF), treatment satisfaction (TS) and disease perception (DP). After being given necessary explanation by doctors, the questions were answered independently by patients.

The main endpoint events time was calculated in accordance with the following method. If the endpoint events occurred, the time was defined as the duration from the first administration of drug to the time when any one of aforesaid events occurred (e.g. if there were plural endpoint events in a same disease, the most recent time when event occurred was deemed as the main endpoint events time.). If the subjects dropped out of the trial or lost follow-up for any reason before the end of study, the time was calculated on the basis of withdrawal or out of follow-up time. If the subjects survived to the last observation, the time was calculated on the basis of the last observation time.

I.2.2 Secondary Indexes for Therapeutic Effects

The secondary indexes included the overall survival time, angina pectoris score, TCM symptom score and SAQ.

Overall Survival Time

Death endpoint referred to the death caused by any reason during the period of study. Other cases were defined as censorship.

Death endpoint time was calculated in accordance with following method. The time referred to the duration from the first administration of drug to the time when the endpoint events occurred, and non-endpoint time was defined with reference to method of the main endpoint event.

I.3 Safety Indexes Mainly Include:

Adverse event referred to any adverse medical events that happened from the time when patients signed the Informed consent form (ICF) and were enrolled in trial to the end of treatment, whether having a relationship with the test drug or not.

Severe adverse event included death and other cases threatening life, events leading to hospitalization treatment, prolonged hospitalization treatment, permanently or severely causing disability or malformation.

Statistical Population

1. Full Analysis Set (FAS) Population

Ideal cases set was established as possible as in accordance with the intentional treatment principle, which was obtained from the randomized subjects, to the exclusion of the least or unreasonable cases.

Missing Data Processing (1). Endpoint events were processed in accordance with the survival data analysis. See the main indexes for therapeutic effects in section of statistical analysis.

(2). Other treatment indexes included angina pectoris score, TCM symptom score and various evaluation results that were recorded in the SAQ. The missing value for aforesaid indexes was estimated on the basis of the closest last observation carried forward (LOCF) estimation method.

2. Per-Protocol (PP) Population

Also, the PP population was called as valid cases, valid samples or evaluable cases. Full compliance with the trial program made it ensure that the data set was generated by the valid case subset shown by scientific model.

3. Safety Set (SS) Population

The SS population of this trial consisted of the subjects who received at least one treatment after randomization.

Division of the statistical analysis population was determined jointly by clinical researchers, data managers and statistical analysis experts on blind review meeting.

Statistical Analysis Method

I.4 General Principle

Two-sided test was used in all statistical tests. It was believed to have statistical significance ($p \leq 0.05$, unless otherwise indicated).

Quantitative indexes were expressed as mean value, standard deviation, median value, minimum value and maximum value.

Classification indexes were expressed as number of samples and its percentage.

I.5 Evaluation of Therapeutic Effect 1.5.1 Baseline

The baseline was defined as observation #1 of patients who entered the group before administration. The baseline evaluation was carried out in FAS population.

Either t-test or Wilcoxon rank sum test could be used for inter-group baseline comparison by total and single scores of angina pectoris, total and single scores of TCM symptom and the score of each question recorded in the SAQ.

I.5.2 Evaluation of Main Therapeutic Effects

Main therapeutic effects referred to the survival rate of main endpoint events.

Kaplan-Meier method was used to estimate the survival rate of main endpoint events in both trial and control group. The survival curve was established after calculating onset time at 25%, 50% and 75% quantile. Log-rank test was used for inter-group comparison.

Cox proportional hazard model was used to test the risk of endpoint events occurring in trial group in comparison with the control group to calculate its 95% confidence interval.

About the definition and calculation method of main endpoint events, see the relevant section of indexes of therapeutic effects.

I.5.3 Evaluation of Secondary Therapeutic Effects

They included the overall survival time, angina pectoris score, TCM symptom score and life quality score, where angina pectoris score, TCM symptom score and life quality score were evaluated at randomization, in $1^{st}$, $3^{rd}$, $6^{th}$, $9^{th}$, $12^{th}$ month after treatment and $18^{th}$ month after follow-up.

I.5.3.1 Overall Survival Time

Analysis method referred to the survival rate of main endpoint events. About the definition and calculation method of overall survival time, see the relevant section of indexes of therapeutic effects.

I.5.3.2 Angina Pectoris Score

Total angina pectoris score was described on every observation period and the change of observation in comparison with baseline. T-test or Wilcoxon rank sum test were used for inter-group comparison. Grade of total score was evaluated on every observation and Wilcoxon rank sum test was used for inter-group comparison. T-test and Pairing signed rank sum test were used for analyzing the change of total score on every observation between groups in comparison with the baseline.

Single angina pectoris score was depicted on every observation time-point and the change of observation in comparison with baseline. Wilcoxon rank sum test was used for inter-group comparison. Pairing signed rank sum test was used for analyzing the change of total score on every observation between groups in comparison with the baseline.

I.5.3.3 TCM Symptom Score

The analysis method referred to the angina pectoris score.

I.5.3.4 SAQ

All evaluation results of SAQ were described during the period of observation, and Wilcoxon rank sum test was used for inter-group comparison.

I.6 Evaluation of Safety

I.6.1 Patients' Exposure Time in Study

Observation time (day)=(ending date-starting date)+1
Medication time (day)=(last date-initial date)+1

I.6.2 Indexes for Evaluation of Safety

Adverse events were evaluated at any time after enrollment. Safety population was used for the indexes for evaluation of safety.

I.6.3 Safety Evaluation Method

Occurrence, proportion and number of the adverse events were described group by group in each treatment group. The patients who were aborted from trial by adverse events, and the ones of related adverse events and severe adverse events were described in list.

Results of Statistical Analysis

In this study, the data were for blind review and then locked.

After opening the blind on the spot, the results were divided into two groups of #A and #B for the first time and the main indexes for therapeutic effect was evaluated. After opening blind for the second time, #A group was trial group and #B group control group.

Total 3508 patients were enrolled in this study, 1748 patients in trial group and 1760 patients in control group respectively. There were 3505 patients entering the FAS population, respectively 1746 patients in trial group and 1759 patients in control group. There were 2956 patients entering the PP population, respectively 1456 patients in trial group and 1500 patients in control group. There were 3507 patients entering the SS population, respectively 1747 patients in trial group and 1760 patients in control group.

Indexes for Therapeutic Effect

Baseline:

Except there was statistically significant difference in fatigue indexes of TCM symptom between the groups ($P<0.05$), no statistically significant difference was found in other indexes ($P>0.05$).

Main Indexes for Therapeutic Effect:

Occurrence of Main Endpoint Events

TABLE 1 test of incidence of main endpoint events in two groups at different times (FAS)

| | Test method | statistic | P value |
|---|---|---|---|
| Time | Log-Rank test | 0.00 | 0.9523 |

TABLE 2

Cox model of survival time (risk rate and 95% CI) (FAS)-random method

| Items | Total (trial group = 1746, control group = 1759, N = 3505) |
|---|---|
| Survival time (Cox model) | |
| Trial group v. control group | 1.01 (0.72, 1.42) |
| Likelihood ratio (P) | 0.00 (0.952) |

Figure 2:
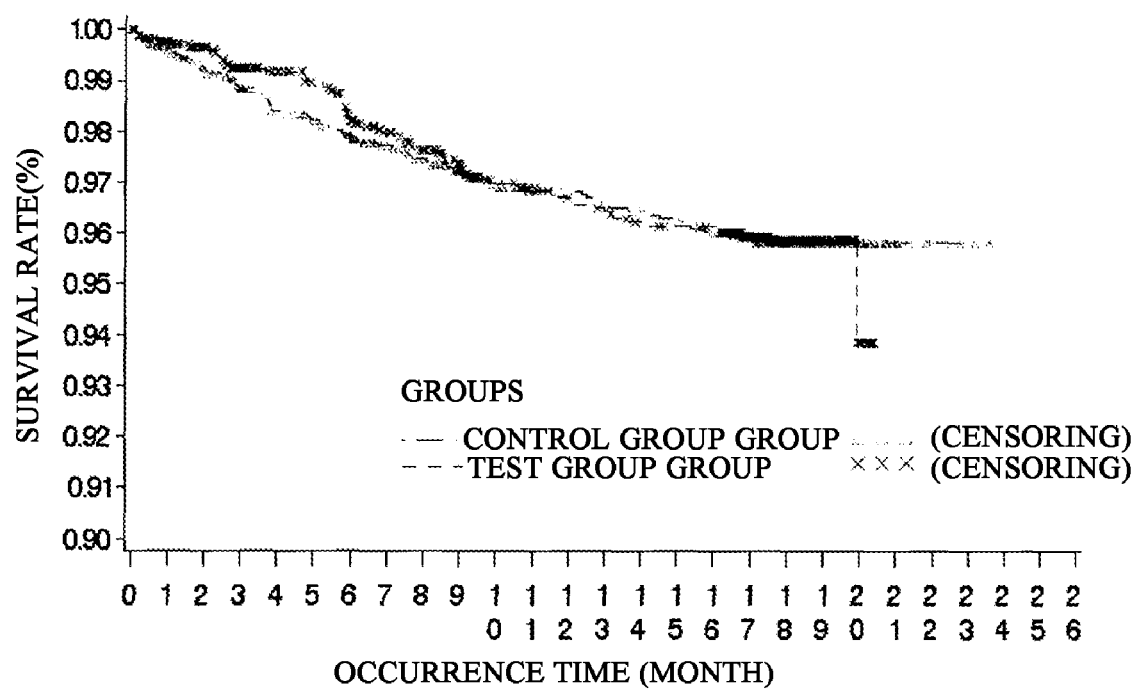

As for Kaplan-Meier time curve of main endpoint event (FAS), see FIG. 1 and FIG. 2.

TABLE 3 test of incidence of main endpoint events in two groups at different times (PP)

| | Test method | Statistic | P value |
|---|---|---|---|
| Time | Log-Rank test | 0.00 | 0.9788 |

TABLE 4

Cox model of survival time (risk rate and 95% CI)-random method

| Items | Total (trial group = 1456 control group = 1500 N = 2956) |
|---|---|
| Survival time (Cox model) | |
| Trial group v. control group | (1.00 (0.71, 1.42) |
| Likelihood ratio (P) | 0.00 (0.979) |

Figure 3:
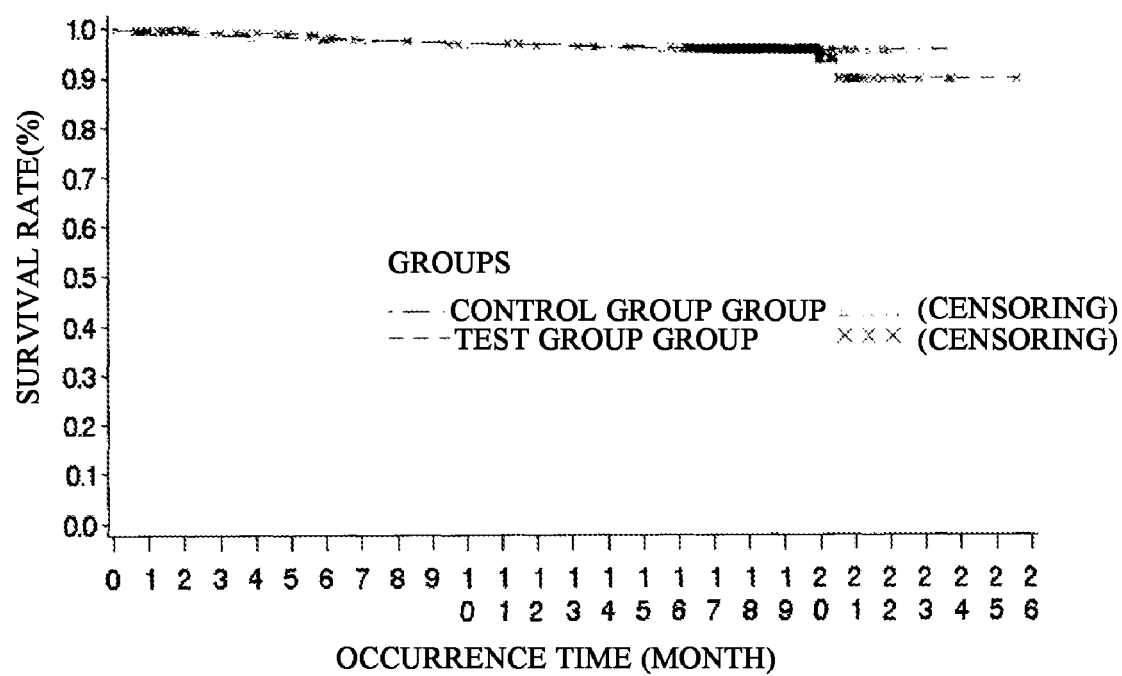
Figure 4:
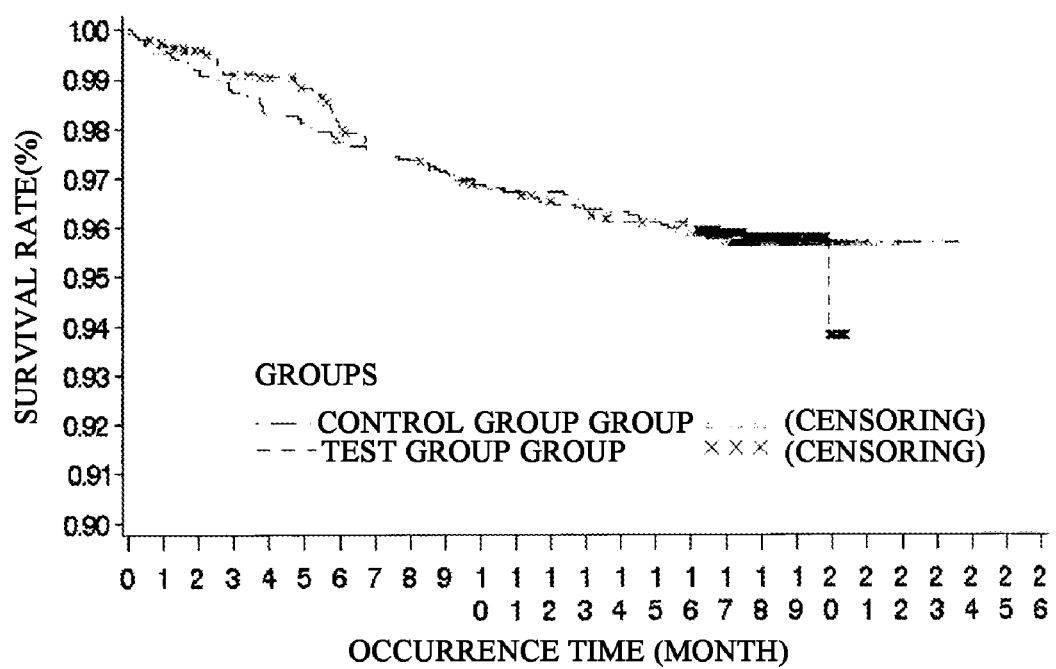

As for Kaplan-Meier time curve of main endpoint event (FAS), see FIG. 3 and FIG. 4.

TABLE 5 test of incidence of death endpoint events in two groups at different times (PP)

| | Test method | statistic | P value |
|---|---|---|---|
| Time | Log-Rank test | 1.27 | 0.2592 |

TABLE 6

Cox model of survival time (risk rate and 95% CI) (FAS)-random method

| Items | Total (trial = 1746 control = 1759 total = 3505) |
|---|---|
| Survival time (Cox model) | |
| Trial group vs. control group | 1.29 (0.83, 2.01) |
| Likelihood ratio (P) | 1.28 (0.259) |

Figure 5:
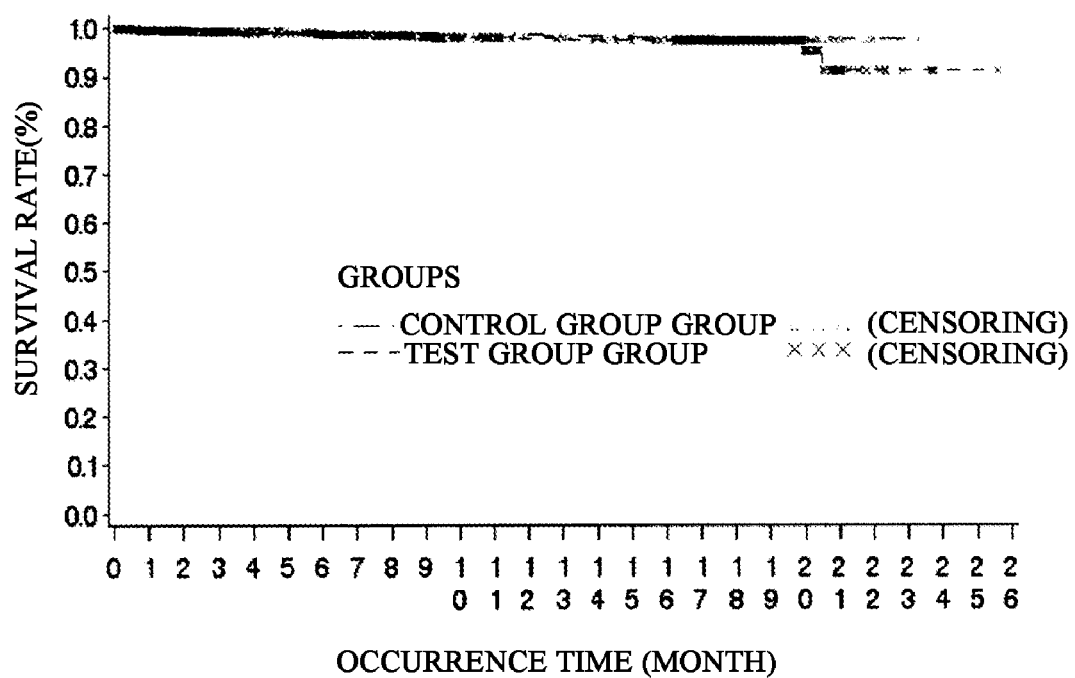
Figure 6:
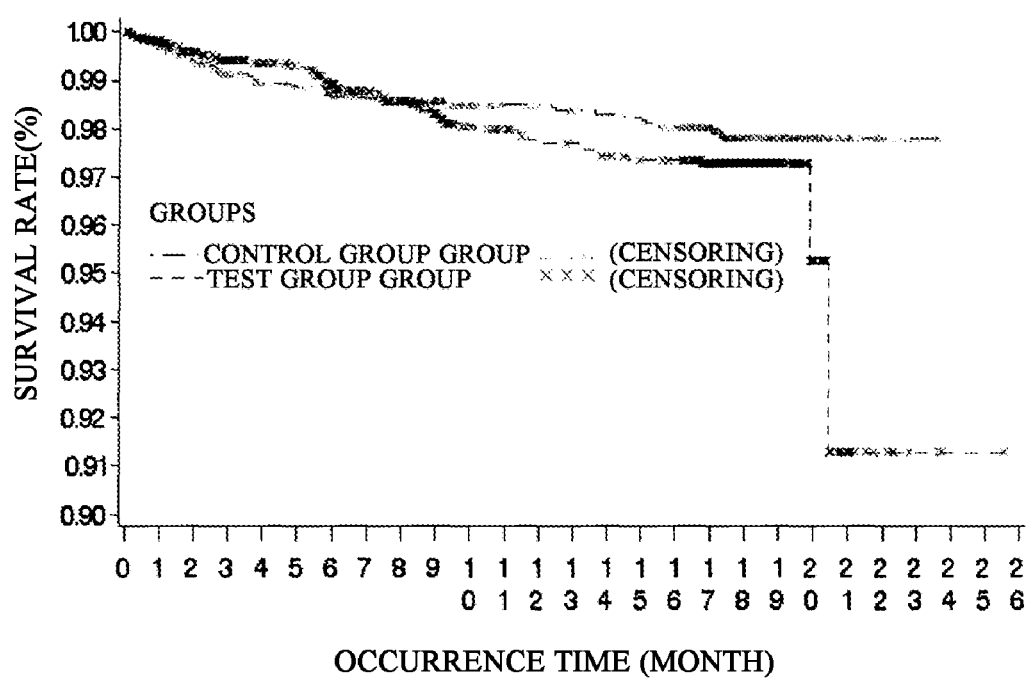

As for Kaplan-Meier time curve of death endpoint event (FAS), see FIG. 5 and FIG. 6.

TABLE 7 test of incidence of death endpoint events in two groups at different times (PP)

| | Test method | statistic | P value |
|---|---|---|---|
| Time | Log-Rank test | 1.19 | 0.2752 |

TABLE 8

Cox model of survival time (risk rate and 95% CI) (PP)-random method

| Items | Total (trial group = 1456 control group = 1500 N = 2956) |
|---|---|
| Survival time (Cox model) | |
| Group A Vs. Group B | 1.29 (0.82, 2.04) |
| Likelihood ratio (P) | 1.19 (0.275) |

Figure 7:
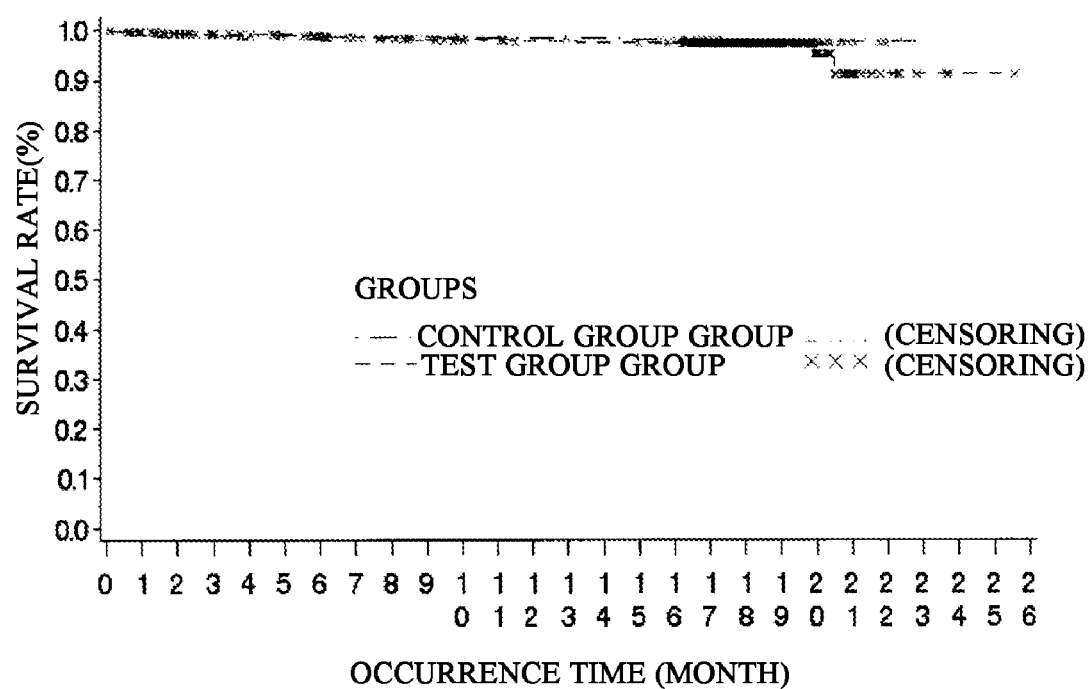
Figure 8:
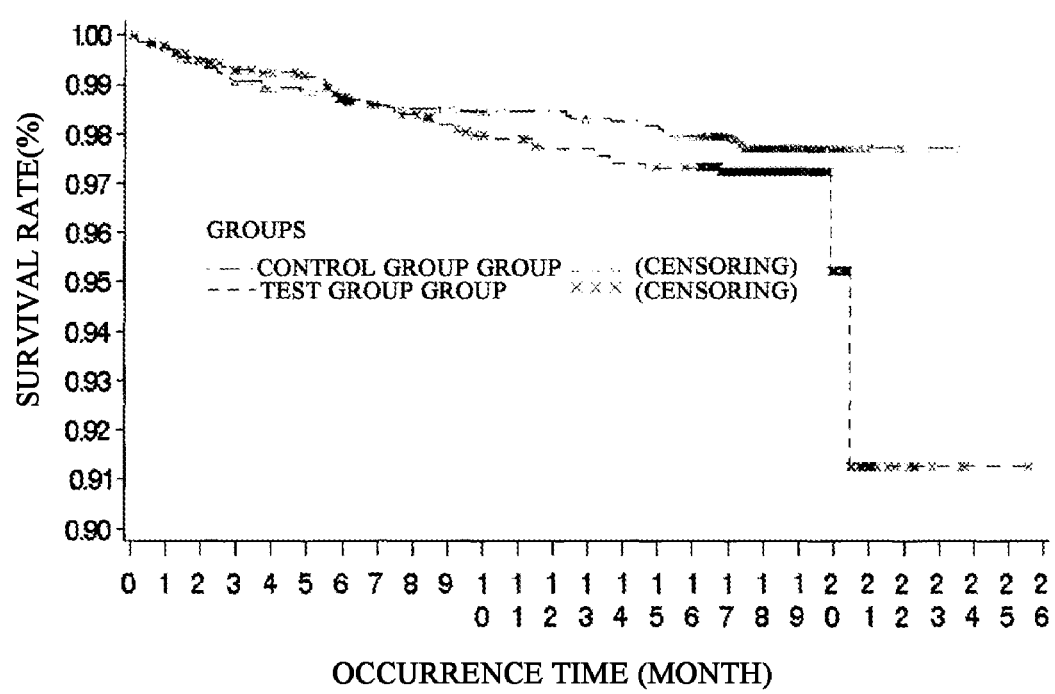

As for Kaplan-Meier time curve of death endpoint event (PP), see FIG. 7 and FIG. 8

I.6.4.2 Angina Pectoris Score

Total angina pectoris score was described on every observation period and the change of observation in comparison with the baseline. T-test or Wilcoxon rank sum test were used for inter-group comparison. Grade of total score was evaluated on every observation and Wilcoxon rank sum test was used for inter-group comparison. T-test and Pairing signed rank sum test were used for analyzing the change of total score on every observation between groups in comparison with the baseline.

Single angina pectoris score was described on every observation time-point and the change of observation in comparison with baseline. Wilcoxon rank sum test was used for inter-group comparison. Pairing signed rank sum test was used for analyzing the change of total score on every observation between groups in comparison with the baseline.

TABLE 9 change of total angina pectoris score in every observation

| | FAS | | PP | |
|---|---|---|---|---|
| Items | Control group | Trial group | Control group | Trial group |
| Baseline | | | | |
| N (Missing) | 1743 (16) | 1721 (25) | 1497 (3) | 1447 (9) |
| Mean (SD) | 7.12 (5.31) | 7.21 (5.20) | 7.20 (5.31) | 7.43 (5.25) |
| Min, Max | 0.00, 24.00 | 0.00, 24.00 | 0.00, 24.00 | 0.00, 24.00 |
| Md (Q3-Q1) | 8.00 (12.00) | 8.00 (9.00) | 8.00 (12.00) | 8.00 (7.00) |
| 1 month after treatment | | | | |
| N (Missing) | 1744 (15) | 1725 (21) | 1489 (11) | 1447 (9) |
| Mean (SD) | 5.92 (5.23) | 5.96 (5.11) | 5.95 (5.21) | 6.06 (5.17) |
| Min, Max | 0.00, 22.00 | 0.00, 24.00 | 0.00, 22.00 | 0.00, 24.00 |
| Md (Q3-Q1) | 6.00 (10.00) | 6.00 (10.00) | 6.00 (10.00) | 6.00 (10.00) |
| 1 month after treatment-baseline | | | | |
| N (Missing) | 1743 (16) | 1721 (25) | 1488 (12) | 1443 (13) |
| Mean (SD) | −1.19 (3.66) | −1.24 (3.86) | −1.22 (3.64) | −1.36 (3.82) |
| Min, Max | −20.00, 16.00 | −22.00, 16.00 | −20.00, 16.00 | −22.00, 16.00 |
| Md (Q3-Q1) | 0.00 (2.00) | 0.00 (2.00) | 0.00 (2.00) | 0.00 (2.00) |
| Pairing t test (P) | −13.59 (0.0000) | −13.33 (0.0000) | −12.92 (0.0000) | −13.57 (0.0000) |
| 3 months after treatment | | | | |
| N (Missing) | 1744 (15) | 1725 (21) | 1473 (27) | 1433 (23) |
| Mean (SD) | 5.38 (5.04) | 5.47 (4.92) | 5.32 (4.99) | 5.49 (4.91) |
| Min, Max | 0.00, 22.00 | 0.00, 24.00 | 0.00, 22.00 | 0.00, 24.00 |
| Md (Q3-Q1) | 6.00 (9.00) | 6.00 (8.00) | 6.00 (9.00) | 6.00 (9.00) |
| 3 months after treatment-baseline | | | | |
| N (Missing) | 1743 (16) | 1721 (25) | 1472 (28) | 1429 (27) |
| Mean (SD) | −1.73 (4.15) | −1.75 (4.26) | −1.85 (4.08) | −1.92 (4.15) |
| Min, Max | −22.00, 16.00 | −22.00, 15.00 | −20.00, 14.00 | −22.00, 14.00 |
| Md (Q3-Q1) | 0.00 (4.00) | 0.00 (3.00) | 0.00 (4.00) | 0.00 (4.00) |
| Pairing t test (P) | −17.43 (0.0000) | −17.04 (0.0000) | −17.38 (0.0000) | −17.50 (0.0000) |
| 6 months after treatment | | | | |
| N (Missing) | 1744 (15) | 1725 (21) | 1457 (43) | 1413 (43) |
| Mean (SD) | 4.78 (4.84) | 4.96 (4.79) | 4.54 (4.68) | 4.85 (4.66) |
| Min, Max | 0.00, 24.00 | 0.00, 22.00 | 0.00, 24.00 | 0.00, 22.00 |
| Md (Q3-Q1) | 5.00 (8.00) | 6.00 (8.00) | 5.00 (8.00) | 5.00 (8.00) |
| 6 months after treatment-baseline | | | | |
| N (Missing) | 1743 (16) | 1721 (25) | 1456 (44) | 1409 (47) |
| Mean (SD) | −2.34 (4.40) | −2.26 (4.63) | −2.58 (4.34) | −2.56 (4.45) |
| Min, Max | −24.00, 14.00 | −22.00, 18.00 | −24.00, 14.00 | −22.00, 18.00 |
| Md (Q3-Q1) | 0.00 (5.00) | 0.00 (5.00) | −1.00 (5.00) | −1.00 (5.00) |
| Pairing t test (P) | −22.15 (0.0000) | −20.29 (0.0000) | −22.67 (0.0000) | −21.57 (0.0000) |
| 9 months after treatment | | | | |
| N (Missing) | 1744 (15) | 1725 (21) | 1443 (57) | 1383 (73) |
| Mean (SD) | 4.39 (4.65) | 4.52 (4.61) | 4.10 (4.40) | 4.24 (4.36) |
| Min, Max | 0.00, 22.00 | 0.00, 22.00 | 0.00, 22.00 | 0.00, 18.00 |
| Md (Q3-Q1) | 5.00 (8.00) | 5.00 (8.00) | 5.00 (8.00) | 5.00 (8.00) |
| 9 months after treatment-baseline | | | | |
| N (Missing) | 1743 (16) | 1721 (25) | 1442 (58) | 1379 (77) |
| Mean (SD) | −2.72 (4.66) | −2.70 (4.92) | −3.02 (4.61) | −3.16 (4.69) |
| Min, Max | −24.00, 14.00 | −24.00, 18.00 | −24.00, 14.00 | −24.00, 18.00 |
| Md (Q3-Q1) | −1.00 (6.00) | −1.00 (6.00) | −2.00 (6.00) | −2.00 (6.00) |
| Pairing t test (P) | −24.42 (0.0000) | −22.76 (0.0000) | −24.86 (0.0000) | −25.04 (0.0000) |
| 12 months after treatment | | | | |
| N (Missing) | 1744 (15) | 1725 (21) | 1432 (68) | 1373 (83) |
| Mean (SD) | 3.83 (4.47) | 4.03 (4.42) | 3.38 (4.05) | 3.63 (4.04) |
| Min, Max | 0.00, 22.00 | 0.00, 22.00 | 0.00, 18.00 | 0.00, 20.00 |
| Md (Q3-Q1) | 0.00 (7.00) | 5.00 (8.00) | 0.00 (6.00) | 0.00 (7.00) |
| 12 months after treatment-baseline | | | | |
| N (Missing) | 1743 (16) | 1721 (25) | 1431 (69) | 1369 (87) |
| Mean (SD) | −3.28 (4.82) | −3.19 (5.05) | −3.71 (4.72) | −3.79 (4.71) |
| Min, Max | −24.00, 16.00 | −24.00, 18.00 | −24.00, 16.00 | −24.00, 11.00 |
| Md (Q3-Q1) | −2.00 (6.00) | −2.00 (6.00) | −3.00 (6.00) | −3.00 (6.00) |
| Pairing t test (P) | −28.43 (0.0000) | −26.17 (0.0000) | −29.75 (0.0000) | −29.75 (0.0000) |

TABLE 9-continued change of total angina pectoris score in every observation

| Items | FAS | | PP | |
|---|---|---|---|---|
| | Control group | Trial group | Control group | Trial group |
| Follow-up | | | | |
| N (Missing) | 1443 (316) | 1385 (361) | 1408 (92) | 1349 (107) |
| Mean (SD) | 3.59 (4.24) | 3.67 (4.11) | 3.60 (4.23) | 3.68 (4.10) |
| Min, Max | 0.00, 18.00 | 0.00, 18.00 | 0.00, 18.00 | 0.00, 18.00 |
| Md (Q3-Q1) | 0.00 (7.00) | 0.00 (7.00) | 0.00 (7.00) | 0.00 (7.00) |
| Follow-up-baseline | | | | |
| N (Missing) | 1443 (316) | 1381 (365) | 1408 (92) | 1345 (111) |
| Mean (SD) | −3.49 (4.97) | −3.74 (4.93) | −3.51 (4.98) | −3.73 (4.90) |
| Min, Max | −24.00, 14.00 | −24.00, 10.00 | −24.00, 14.00 | −24.00, 10.00 |
| Md (Q3-Q1) | −2.00 (6.00) | −2.00 (7.00) | −2.00 (6.00) | −2.00 (7.00) |
| Pairing t test (P) | −26.63 (0.0000) | −28.17 (0.0000) | −26.42 (0.0000) | −27.95 (0.0000) |

TABLE 10 distribution of total angina pectoris score in every observation

| Items | FAS | | PP | |
|---|---|---|---|---|
| | Control group | trial group | Control group | trial group |
| Baseline | | | | |
| Mild | 1086 (62.34%) | 1092 (63.45%) | 917 (61.26%) | 880 (60.82%) |
| Medium | 608 (34.90%) | 574 (33.35%) | 539 (36.01%) | 516 (35.66%) |
| Severe | 48 (2.76%) | 55 (3.20%) | 41 (2.74%) | 51 (3.52%) |
| Total | 1742 | 1721 | 1497 | 1447 |
| 1 month after treatment | | | | |
| Mild | 1203 (70.19%) | 1210 (71.09%) | 1030 (69.31%) | 1013 (70.06%) |
| Medium | 484 (28.24%) | 464 (27.26%) | 434 (29.21%) | 407 (28.15%) |
| Severe | 27 (1.58%) | 28 (1.65%) | 22 (1.48%) | 26 (1.80%) |
| Total | 1714 | 1702 | 1486 | 1446 |
| 3 months after treatment | | | | |
| Mild | 1241 (74.94%) | 1247 (75.81%) | 1098 (74.54%) | 1075 (75.02%) |
| Medium | 397 (23.97%) | 386 (23.47%) | 363 (24.64%) | 348 (24.28%) |
| Severe | 18 (1.09%) | 12 (0.73%) | 12 (0.81%) | 10 (0.70%) |
| Total | 1656 | 1645 | 1473 | 1433 |
| 6 months after treatment | | | | |
| Mild | 1273 (80.06%) | 1252 (79.90%) | 1172 (80.44%) | 1125 (79.62%) |
| Medium | 309 (19.43%) | 305 (19.46%) | 278 (19.08%) | 280 (19.82%) |
| Severe | 8 (0.50%) | 10 (0.64%) | 7 (0.48%) | 8 (0.57%) |
| Total | 1590 | 1567 | 1457 | 1413 |
| 9 months after treatment | | | | |
| Mild | 1280 (83.77%) | 1220 (83.05%) | 1207 (83.65%) | 1147 (82.94%) |
| Medium | 244 (15.97%) | 241 (16.41%) | 233 (16.15%) | 229 (16.56%) |
| Severe | 4 (0.26%) | 8 (0.54%) | 3 (0.21%) | 7 (0.51%) |
| Total | 1528 | 1469 | 1443 | 1383 |
| 12 months after treatment | | | | |
| Mild | 1294 (87.91%) | 1217 (86.31%) | 1259 (87.92%) | 1184 (86.23%) |
| Medium | 176 (11.96%) | 189 (13.40%) | 171 (11.94%) | 185 (13.47%) |
| Severe | 2 (0.14%) | 4 (0.28%) | 2 (0.14%) | 4 (0.29%) |
| Total | 1472 | 1410 | 1432 | 1373 |

TABLE 10-continued distribution of total angina pectoris score in every observation

| Items | FAS Control group | FAS trial group | PP Control group | PP trial group |
|---|---|---|---|---|
| Follow-up | | | | |
| Mild | 1243 (86.14%) | 1185 (85.56%) | 1215 (86.29%) | 1155 (85.62%) |
| Medium | 199 (13.79%) | 199 (14.37%) | 192 (13.64%) | 193 (14.31%) |
| Severe | 1 (0.07%) | 1 (0.07%) | 1 (0.07%) | 1 (0.07%) |
| Total | 1443 | 1385 | 1408 | 1349 |

TABLE 11 test of distribution of total angina pectoris score in every observation

| Items | Test method | FAS Statistic | FAS P value | PP statistic | PP P value |
|---|---|---|---|---|---|
| Baseline | Rank-sum test | −0.55 | 0.5813 | 0.40 | 0.6864 |
| 1 month after treatment | Rank-sum test | −0.56 | 0.5775 | −0.37 | 0.7102 |
| 3 months after treatment | Rank-sum test | −0.63 | 0.5289 | −0.31 | 0.7560 |
| 6 months after treatment | Rank-sum test | 0.13 | 0.8934 | 0.56 | 0.5765 |
| 9 months after treatment | Rank-sum test | 0.56 | 0.5743 | 0.54 | 0.5900 |
| 12 months after treatment | Rank-sum test | 1.29 | 0.1968 | 1.34 | 0.1795 |
| Follow-up | Rank-sum test | 0.44 | 0.6580 | 0.51 | 0.6109 |

TABLE 12 change of attack times in different observations

| Items | FAS Control group | FAS Trial group | PP Control group | PP Trial group |
|---|---|---|---|---|
| Baseline | | | | |
| 0 | 480 (27.54%) | 444 (25.80%) | 404 (26.99%) | 358 (24.74%) |
| 1 | 158 (9.06%) | 166 (9.65%) | 134 (8.95%) | 133 (9.19%) |
| 2 | 928 (53.24%) | 958 (55.67%) | 801 (53.51%) | 819 (56.60%) |
| 4 | 159 (9.12%) | 133 (7.73%) | 143 (9.55%) | 119 (8.22%) |
| 6 | 18 (1.03%) | 20 (1.16%) | 15 (1.00%) | 18 (1.24%) |
| Total | 1743 | 1721 | 1497 | 1447 |
| month after treatment | | | | |
| 0 | 638 (36.58%) | 606 (35.13%) | 541 (36.33%) | 501 (34.62%) |
| 1 | 187 (10.72%) | 205 (11.88%) | 165 (11.08%) | 170 (11.75%) |
| 2 | 812 (46.56%) | 835 (48.41%) | 698 (46.88%) | 704 (48.65%) |
| 4 | 105 (6.02%) | 71 (4.12%) | 83 (5.57%) | 65 (4.49%) |
| 6 | 2 (0.11%) | 8 (0.46%) | 2 (0.13%) | 7 (0.48%) |
| Total | 1744 | 1725 | 1489 | 1447 |
| 1 month after treatment-baseline | | | | |
| −6 | 2 (0.11%) | 2 (0.12%) | 1 (0.07%) | 2 (0.14%) |
| −5 | 0 (0.00%) | 1 (0.06%) | 0 (0.00%) | 1 (0.07%) |
| −4 | 18 (1.03%) | 24 (1.39%) | 16 (1.08%) | 21 (1.46%) |
| −3 | 6 (0.34%) | 6 (0.35%) | 6 (0.40%) | 4 (0.28%) |
| −2 | 209 (11.99%) | 185 (10.75%) | 188 (12.63%) | 157 (10.88%) |
| −1 | 124 (7.11%) | 150 (8.72%) | 105 (7.06%) | 128 (8.87%) |
| 0 | 1304 (74.81%) | 1277 (74.20%) | 1109 (74.53%) | 1076 (74.57%) |
| 1 | 36 (2.07%) | 31 (1.80%) | 29 (1.95%) | 25 (1.73%) |
| 2 | 41 (2.35%) | 43 (2.50%) | 31 (2.08%) | 28 (1.94%) |

TABLE 12-continued change of attack times in different observations

| | FAS | | PP | |
|---|---|---|---|---|
| Items | Control group | Trial group | Control group | Trial group |
| 3 | 2 (0.11%) | 2 (0.12%) | 2 (0.13%) | 1 (0.07%) |
| 4 | 1 (0.06%) | 0 (0.00%) | 1 (0.07%) | 0 (0.00%) |
| Total | 1743 | 1721 | 1488 | 1443 |
| Signed-rank (P) | −32430 (0.0000) | −33041 (0.0000) | −25398.5 (0.0000) | −24610.0 (0.0000) |
| 3 months after treatment | | | | |
| 0 | 698 (40.02%) | 658 (38.14%) | 596 (40.46%) | 544 (37.96%) |
| 1 | 246 (14.11%) | 247 (14.32%) | 205 (13.92%) | 199 (13.89%) |
| 2 | 723 (41.46%) | 755 (43.77%) | 617 (41.89%) | 636 (44.38%) |
| 4 | 75 (4.30%) | 60 (3.48%) | 53 (3.60%) | 50 (3.49%) |
| 6 | 2 (0.11%) | 5 (0.29%) | 2 (0.14%) | 4 (0.28%) |
| Total | 1744 | 1725 | 1473 | 1433 |
| 3 months after treatment-baseline | | | | |
| −6 | 4 (0.23%) | 2 (0.12%) | 2 (0.14%) | 2 (0.14%) |
| −5 | 2 (0.11%) | 2 (0.12%) | 2 (0.14%) | 2 (0.14%) |
| −4 | 25 (1.43%) | 26 (1.51%) | 23 (1.56%) | 20 (1.40%) |
| −3 | 8 (0.46%) | 9 (0.52%) | 8 (0.54%) | 8 (0.56%) |
| −2 | 275 (15.78%) | 245 (14.24%) | 243 (16.51%) | 210 (14.70%) |
| −1 | 191 (10.96%) | 208 (12.09%) | 165 (11.21%) | 171 (11.97%) |
| 0 | 1142 (65.52%) | 1143 (66.41%) | 959 (65.15%) | 959 (67.11%) |
| 1 | 54 (3.10%) | 41 (2.38%) | 41 (2.79%) | 28 (1.96%) |
| 2 | 39 (2.24%) | 41 (2.38%) | 27 (1.83%) | 26 (1.82%) |
| 3 | 0 (0.00%) | 1 (0.06%) | | |
| 4 | 3 (0.17%) | 3 (0.17%) | 2 (0.14%) | 3 (0.21%) |
| Total | 1743 | 1721 | 1472 | 1429 |
| Signed-rank (P) | −66367 (0.0000) | −60228 (0.0000) | −51462.5 (0.0000) | −42922.5 (0.0000) |
| 6 months after treatment | | | | |
| 0 | 777 (44.55%) | 726 (42.09%) | 670 (45.98%) | 596 (42.18%) |
| 1 | 271 (15.54%) | 314 (18.20%) | 232 (15.92%) | 267 (18.90%) |
| 2 | 642 (36.81%) | 643 (37.28%) | 527 (36.17%) | 523 (37.01%) |
| 4 | 53 (3.04%) | 40 (2.32%) | 27 (1.85%) | 27 (1.91%) |
| 6 | 1 (0.06%) | 2 (0.12%) | 1 (0.07%) | 0 (0.00%) |
| Total | 1744 | 1725 | 1457 | 1413 |
| 6 months after treatment-baseline | | | | |
| −6 | 6 (0.34%) | 4 (0.23%) | 4 (0.27%) | 3 (0.21%) |
| −5 | 0 (0.00%) | 3 (0.17%) | 0 (0.00%) | 3 (0.21%) |
| −4 | 31 (1.78%) | 33 (1.92%) | 28 (1.92%) | 26 (1.85%) |
| −3 | 16 (0.92%) | 13 (0.76%) | 16 (1.10%) | 11 (0.78%) |
| −2 | 326 (18.70%) | 293 (17.02%) | 290 (19.92%) | 250 (17.74%) |
| −1 | 265 (15.20%) | 301 (17.49%) | 234 (16.07%) | 261 (18.52%) |
| 0 | 1010 (57.95%) | 992 (57.64%) | 827 (56.80%) | 803 (56.99%) |
| 1 | 43 (2.47%) | 39 (2.27%) | 28 (1.92%) | 27 (1.91%) |
| 2 | 43 (2.47%) | 40 (2.32%) | 27 (1.85%) | 25 (1.77%) |
| 3 | 1 (0.06%) | 1 (0.06%) | | |
| 4 | 2 (0.11%) | 2 (0.12%) | 2 (0.14%) | 0 (0.00%) |
| Total | 1743 | 1721 | 1456 | 1409 |
| Signed-rank (P) | −105E3 (0.0000) | −104E3 (0.0000) | −82797.5 (0.0000) | −77409.0 (0.0000) |
| 9 months after treatment | | | | |
| 0 | 825 (47.31%) | 777 (45.04%) | 708 (49.06%) | 641 (46.35%) |
| 1 | 354 (20.30%) | 392 (22.72%) | 312 (21.62%) | 345 (24.95%) |
| 2 | 527 (30.22%) | 529 (30.67%) | 409 (28.34%) | 384 (27.77%) |
| 4 | 36 (2.06%) | 25 (1.45%) | 12 (0.83%) | 13 (0.94%) |
| 6 | 2 (0.11%) | 2 (0.12%) | 2 (0.14%) | 0 (0.00%) |
| Total | 1744 | 1725 | 1443 | 1383 |
| 9 months after treatment-baseline | | | | |
| −6 | 7 (0.40%) | 7 (0.41%) | 5 (0.35%) | 5 (0.36%) |
| −5 | 0 (0.00%) | 2 (0.12%) | 0 (0.00%) | 2 (0.15%) |
| −4 | 43 (2.47%) | 40 (2.32%) | 39 (2.70%) | 33 (2.39%) |
| −3 | 15 (0.86%) | 15 (0.87%) | 15 (1.04%) | 13 (0.94%) |
| −2 | 359 (20.60%) | 331 (19.23%) | 321 (22.26%) | 281 (20.38%) |
| −1 | 352 (20.20%) | 390 (22.66%) | 316 (21.91%) | 348 (25.24%) |
| 0 | 877 (50.32%) | 853 (49.56%) | 687 (47.64%) | 650 (47.14%) |
| 1 | 52 (2.98%) | 38 (2.21%) | 35 (2.43%) | 26 (1.89%) |

TABLE 12-continued change of attack times in different observations

| Items | FAS Control group | FAS Trial group | PP Control group | PP Trial group |
|---|---|---|---|---|
| 2 | 35 (2.01%) | 42 (2.44%) | 22 (1.53%) | 21 (1.52%) |
| 3 | 1 (0.06%) | 1 (0.06%) | | |
| 4 | 1 (0.06%) | 2 (0.12%) | 1 (0.07%) | 0 (0.00%) |
| 6 | 1 (0.06%) | 0 (0.00%) | 1 (0.07%) | 0 (0.00%) |
| Total | 1743 | 1721 | 1442 | 1379 |
| Signed-rank (P) | −154E3 (0.0000) | −152E3 (0.0000) | −123547 (0.0000) | −117132 (0.0000) |
| *12 months after treatment* | | | | |
| 0 | 909 (52.12%) | 850 (49.28%) | 788 (55.03%) | 706 (51.42%) |
| 1 | 384 (22.02%) | 425 (24.64%) | 342 (23.88%) | 378 (27.53%) |
| 2 | 417 (23.91%) | 426 (24.70%) | 294 (20.53%) | 279 (20.32%) |
| 4 | 33 (1.89%) | 22 (1.28%) | 8 (0.56%) | 10 (0.73%) |
| 6 | 1 (0.06%) | 2 (0.12%) | | |
| Total | 1744 | 1725 | 1432 | 1373 |
| *12 months after treatment-baseline* | | | | |
| −6 | 7 (0.40%) | 8 (0.46%) | 5 (0.35%) | 6 (0.44%) |
| −5 | 1 (0.06%) | 3 (0.17%) | 1 (0.07%) | 3 (0.22%) |
| −4 | 55 (3.16%) | 45 (2.61%) | 51 (3.56%) | 36 (2.63%) |
| −3 | 15 (0.86%) | 20 (1.16%) | 15 (1.05%) | 18 (1.31%) |
| −2 | 401 (23.01%) | 364 (21.15%) | 358 (25.02%) | 312 (22.79%) |
| −1 | 399 (22.89%) | 445 (25.86%) | 364 (25.44%) | 401 (29.29%) |
| 0 | 795 (45.61%) | 765 (44.45%) | 599 (41.86%) | 561 (40.98%) |
| 1 | 36 (2.07%) | 30 (1.74%) | 19 (1.33%) | 17 (1.24%) |
| 2 | 30 (1.72%) | 38 (2.21%) | 17 (1.19%) | 15 (1.10%) |
| 3 | 1 (0.06%) | 1 (0.06%) | | |
| 4 | 3 (0.17%) | 2 (0.12%) | 2 (0.14%) | 0 (0.00%) |
| Total | 1743 | 1721 | 1431 | 1369 |
| Signed-rank (P) | −194E3 (0.0000) | −193E3 (0.0000) | −158309 (0.0000) | −151127 (0.0000) |
| *Follow-up* | | | | |
| 0 | 774 (53.64%) | 716 (51.70%) | 753 (53.48%) | 693 (51.37%) |
| 1 | 329 (22.80%) | 385 (27.80%) | 322 (22.87%) | 378 (28.02%) |
| 2 | 331 (22.94%) | 281 (20.29%) | 324 (23.01%) | 275 (20.39%) |
| 4 | 9 (0.62%) | 3 (0.22%) | 9 (0.64%) | 3 (0.22%) |
| Total | 1443 | 1385 | 1408 | 1349 |
| *Follow-up baseline* | | | | |
| −6 | 6 (0.42%) | 4 (0.29%) | 6 (0.43%) | 4 (0.30%) |
| −5 | 3 (0.21%) | 5 (0.36%) | 3 (0.21%) | 5 (0.37%) |
| −4 | 52 (3.60%) | 44 (3.19%) | 52 (3.69%) | 42 (3.12%) |
| −3 | 29 (2.01%) | 30 (2.17%) | 29 (2.06%) | 29 (2.16%) |
| −2 | 328 (22.73%) | 312 (22.59%) | 322 (22.87%) | 304 (22.60%) |
| −1 | 325 (22.52%) | 372 (26.94%) | 316 (22.44%) | 365 (27.14%) |
| 0 | 645 (44.70%) | 572 (41.42%) | 626 (44.46%) | 557 (41.41%) |
| 1 | 28 (1.94%) | 25 (1.81%) | 28 (1.99%) | 23 (1.71%) |
| 2 | 25 (1.73%) | 17 (1.23%) | 24 (1.70%) | 16 (1.19%) |
| 4 | 2 (0.14%) | 0 (0.00%) | 2 (0.14%) | 0 (0.00%) |
| Total | 1443 | 1381 | 1408 | 1345 |
| Signed-rank (P) | −14E4 (0.0000) | −149E3 (0.0000) | −134334 (0.0000) | −142184 (0.0000) |

TABLE 13 test of change of attack times in different observations

| Items | test method | FAS statistic | FAS P value | PP statistic | PP P value |
|---|---|---|---|---|---|
| Baseline | Rank-sum test | 0.33 | 0.7424 | 0.73 | 0.4660 |
| 1 month after treatment | Rank-sum test | 0.03 | 0.9749 | 0.54 | 0.5918 |
| 1 month after treatment-baseline | Rank-sum test | −0.45 | 0.6511 | −0.34 | 0.7340 |
| 3 months after treatment | Rank-sum test | 0.91 | 0.3633 | 1.41 | 0.1592 |
| 3 months after treatment-baseline | Rank-sum test | 0.22 | 0.8279 | 0.53 | 0.5932 |
| 6 months after treatment | Rank-sum test | 0.61 | 0.5400 | 1.39 | 0.1638 |

TABLE 13-continued test of change of attack times in different observations

| Items | test method | FAS statistic | FAS P value | PP statistic | PP P value |
|---|---|---|---|---|---|
| 6 months after treatment-baseline | Rank-sum test | −0.08 | 0.9345 | 0.39 | 0.6981 |
| 9 months after treatment | Rank-sum test | 0.68 | 0.4935 | 0.80 | 0.4246 |
| 9 months after treatment-baseline | Rank-sum test | −0.20 | 0.8389 | −0.09 | 0.9306 |
| 12 months after treatment | Rank-sum test | 1.15 | 0.2498 | 1.45 | 0.1478 |
| 12 months after treatment-baseline | Rank-sum test | 0.14 | 0.8926 | 0.25 | 0.7996 |
| Follow-up | Rank-sum test | −0.00 | 0.9960 | 0.06 | 0.9541 |
| Follow-up-baseline | Rank-sum test | −1.39 | 0.1632 | −1.28 | 0.2008 |

TABLE 14 change of duration period in different observations

| Items | FAS Control group | FAS trial group | PP control group | PP trial group |
|---|---|---|---|---|
| Baseline | | | | |
| 0 | 480 (27.54%) | 446 (25.92%) | 404 (26.99%) | 359 (24.81%) |
| 2 | 798 (45.78%) | 834 (48.46%) | 687 (45.89%) | 681 (47.06%) |
| 4 | 382 (21.92%) | 371 (21.56%) | 343 (22.91%) | 343 (23.70%) |
| 6 | 83 (4.76%) | 70 (4.07%) | 63 (4.21%) | 64 (4.42%) |
| Total | 1743 | 1721 | 1497 | 1447 |
| 1 month after treatment | | | | |
| 0 | 638 (36.58%) | 605 (35.07%) | 541 (36.33%) | 500 (34.55%) |
| 2 | 735 (42.14%) | 779 (45.16%) | 624 (41.91%) | 639 (44.16%) |
| 4 | 339 (19.44%) | 312 (18.09%) | 297 (19.95%) | 283 (19.56%) |
| 6 | 32 (1.83%) | 29 (1.68%) | 27 (1.81%) | 25 (1.73%) |
| Total | 1744 | 1725 | 1489 | 1447 |
| 1 month after treatment-baseline | | | | |
| −6 | 19 (1.09%) | 28 (1.63%) | 13 (0.87%) | 27 (1.87%) |
| −4 | 39 (2.24%) | 44 (2.56%) | 34 (2.28%) | 42 (2.91%) |
| −2 | 269 (15.43%) | 230 (13.36%) | 227 (15.26%) | 186 (12.89%) |
| 0 | 1329 (76.25%) | 1332 (77.40%) | 1141 (76.68%) | 1124 (77.89%) |
| 2 | 75 (4.30%) | 72 (4.18%) | 64 (4.30%) | 55 (3.81%) |
| 4 | 10 (0.57%) | 13 (0.76%) | 8 (0.54%) | 8 (0.55%) |
| 6 | 2 (0.11%) | 2 (0.12%) | 1 (0.07%) | 1 (0.07%) |
| Total | 1743 | 1721 | 1488 | 1443 |
| Signed-rank (P) | −25517 (0.0000) | −21968 (0.0000) | −18004.5 (0.0000) | −16427.5 (0.0000) |
| 3 months after treatment | | | | |
| 0 | 697 (39.97%) | 657 (38.09%) | 595 (40.39%) | 543 (37.89%) |
| 2 | 729 (41.80%) | 774 (44.87%) | 606 (41.14%) | 636 (44.38%) |
| 4 | 297 (17.03%) | 274 (15.88%) | 257 (17.45%) | 243 (16.96%) |
| 6 | 21 (1.20%) | 20 (1.16%) | 15 (1.02%) | 11 (0.77%) |
| Total | 1744 | 1725 | 1473 | 1433 |
| 3 months after treatment-baseline | | | | |
| −6 | 26 (1.49%) | 31 (1.80%) | 18 (1.22%) | 28 (1.96%) |
| −4 | 53 (3.04%) | 65 (3.78%) | 43 (2.92%) | 59 (4.13%) |
| −2 | 357 (20.48%) | 303 (17.61%) | 315 (21.40%) | 254 (17.77%) |
| 0 | 1207 (69.25%) | 1223 (71.06%) | 1018 (69.16%) | 1021 (71.45%) |
| 2 | 87 (4.99%) | 84 (4.88%) | 69 (4.69%) | 62 (4.34%) |
| 4 | 11 (0.63%) | 11 (0.64%) | 8 (0.54%) | 4 (0.28%) |
| 6 | 2 (0.11%) | 4 (0.23%) | 1 (0.07%) | 1 (0.07%) |
| Total | 1743 | 1721 | 1472 | 1429 |
| Signed-rank (P) | −46314 (0.0000) | −39225 (0.0000) | −34635.0 (0.0000) | −30105.0 (0.0000) |
| 6 months after treatment | | | | |
| 0 | 777 (44.55%) | 726 (42.09%) | 670 (45.98%) | 596 (42.18%) |
| 2 | 710 (40.71%) | 741 (42.96%) | 588 (40.36%) | 609 (43.10%) |
| 4 | 245 (14.05%) | 245 (14.20%) | 193 (13.25%) | 202 (14.30%) |
| 6 | 12 (0.69%) | 13 (0.75%) | 6 (0.41%) | 6 (0.42%) |
| Total | 1744 | 1725 | 1457 | 1413 |

TABLE 14-continued change of duration period in different observations

| | FAS | | PP | |
|---|---|---|---|---|
| Items | Control group | trial group | control group | trial group |
| 6 months after treatment-baseline | | | | |
| −6 | 27 (1.55%) | 32 (1.86%) | 21 (1.44%) | 29 (2.06%) |
| −4 | 77 (4.42%) | 73 (4.24%) | 66 (4.53%) | 63 (4.47%) |
| −2 | 427 (24.50%) | 396 (23.01%) | 378 (25.96%) | 343 (24.34%) |
| 0 | 1129 (64.77%) | 1125 (65.37%) | 936 (64.29%) | 914 (64.87%) |
| 2 | 79 (4.53%) | 75 (4.36%) | 53 (3.64%) | 52 (3.69%) |
| 4 | 4 (0.23%) | 17 (0.99%) | 2 (0.14%) | 7 (0.50%) |
| 6 | 0 (0.00%) | 3 (0.17%) | 0 (0.00%) | 1 (0.07%) |
| Total | 1743 | 1721 | 1456 | 1409 |
| Signed-rank (P) | −72188 (0.0000) | −60736 (0.0000) | −55351.0 (0.0000) | −47590.0 (0.0000) |
| 9 months after treatment | | | | |
| 0 | 825 (47.31%) | 778 (45.10%) | 708 (49.06%) | 642 (46.42%) |
| 2 | 701 (40.19%) | 762 (44.17%) | 574 (39.78%) | 613 (44.32%) |
| 4 | 205 (11.75%) | 168 (9.74%) | 155 (10.74%) | 120 (8.68%) |
| 6 | 13 (0.75%) | 17 (0.99%) | 6 (0.42%) | 8 (0.58%) |
| Total | 1744 | 1725 | 1443 | 1383 |
| 9 months after treatment-baseline | | | | |
| −6 | 34 (1.95%) | 32 (1.86%) | 27 (1.87%) | 28 (2.03%) |
| −4 | 86 (4.93%) | 100 (5.81%) | 73 (5.06%) | 88 (6.38%) |
| −2 | 485 (27.83%) | 464 (26.96%) | 430 (29.82%) | 408 (29.59%) |
| 0 | 1050 (60.24%) | 1031 (59.91%) | 852 (59.08%) | 803 (58.23%) |
| 2 | 79 (4.53%) | 73 (4.24%) | 53 (3.68%) | 46 (3.34%) |
| 4 | 8 (0.46%) | 16 (0.93%) | 6 (0.42%) | 5 (0.36%) |
| 6 | 1 (0.06%) | 5 (0.29%) | 1 (0.07%) | 1 (0.07%) |
| Total | 1743 | 1721 | 1442 | 1379 |
| Signed-rank (P) | −92350 (0.0000) | −86673 (0.0000) | −70632.0 (0.0000) | −69556.0 (0.0000) |
| 12 months after treatment | | | | |
| 0 | 909 (52.12%) | 851 (49.33%) | 788 (55.03%) | 707 (51.49%) |
| 2 | 683 (39.16%) | 764 (44.29%) | 553 (38.62%) | 615 (44.79%) |
| 4 | 140 (8.03%) | 95 (5.51%) | 87 (6.08%) | 47 (3.42%) |
| 6 | 12 (0.69%) | 15 (0.87%) | 4 (0.28%) | 4 (0.29%) |
| Total | 1744 | 1725 | 1432 | 1373 |
| 12 months after treatment-baseline | | | | |
| −6 | 38 (2.18%) | 37 (2.15%) | 31 (2.17%) | 33 (2.41%) |
| −4 | 111 (6.37%) | 118 (6.86%) | 98 (6.85%) | 106 (7.74%) |
| −2 | 552 (31.67%) | 552 (32.07%) | 492 (34.38%) | 489 (35.72%) |
| 0 | 975 (55.94%) | 930 (54.04%) | 774 (54.09%) | 703 (51.35%) |
| 2 | 61 (3.50%) | 63 (3.66%) | 33 (2.31%) | 35 (2.56%) |
| 4 | 3 (0.17%) | 16 (0.93%) | 0 (0.00%) | 3 (0.22%) |
| 6 | 3 (0.17%) | 5 (0.29%) | 3 (0.21%) | 0 (0.00%) |
| Total | 1743 | 1721 | 1431 | 1369 |
| Signed-rank (P) | −125E3 (0.0000) | −122E3 (0.0000) | −97476.0 (0.0000) | −100131 (0.0000) |
| Follow-up | | | | |
| 0 | 774 (53.64%) | 716 (51.70%) | 753 (53.48%) | 693 (51.37%) |
| 2 | 522 (36.17%) | 544 (39.28%) | 512 (36.36%) | 533 (39.51%) |
| 4 | 144 (9.98%) | 122 (8.81%) | 141 (10.01%) | 120 (8.90%) |
| 6 | 3 (0.21%) | 3 (0.22%) | 2 (0.14%) | 3 (0.22%) |
| Total | 1443 | 1385 | 1408 | 1349 |
| Follow-up-baseline | | | | |
| −6 | 27 (1.87%) | 34 (2.46%) | 27 (1.92%) | 32 (2.38%) |
| −4 | 106 (7.35%) | 112 (8.11%) | 103 (7.32%) | 110 (8.18%) |
| −2 | 441 (30.56%) | 417 (30.20%) | 428 (30.40%) | 404 (30.04%) |
| 0 | 812 (56.27%) | 773 (55.97%) | 795 (56.46%) | 757 (56.28%) |
| 2 | 50 (3.47%) | 41 (2.97%) | 49 (3.48%) | 38 (2.83%) |
| 4 | 5 (0.35%) | 4 (0.29%) | 4 (0.28%) | 4 (0.30%) |
| 6 | 2 (0.14%) | 0 (0.00%) | 2 (0.14%) | 0 (0.00%) |
| Total | 1443 | 1381 | 1408 | 1345 |
| Signed-rank (P) | −83429 (0.0000) | −81093 (0.0000) | −79062.5 (0.0000) | −76168.0 (0.0000) |

TABLE 15 test of duration period in different observations

| | | FAS | | PP | |
|---|---|---|---|---|---|
| Items | test method | Statistic | P value | statistic | P value |
| Baseline | Rank-sum test | 0.16 | 0.8730 | 1.18 | 0.2390 |
| 1 month after treatment | Rank-sum test | 0.13 | 0.8998 | 0.54 | 0.5866 |
| 1 month after treatment-baseline | Rank-sum test | 0.69 | 0.4881 | −0.01 | 0.9929 |
| 3 months after treatment | Rank-sum test | 0.46 | 0.6480 | 0.79 | 0.4318 |
| 3 months after treatment-baseline | Rank-sum test | 0.89 | 0.3749 | 0.32 | 0.7476 |
| 6 months after treatment | Rank-sum test | 1.24 | 0.2148 | 1.95 | 0.0508 |
| 6 months after treatment-baseline | Rank-sum test | 1.04 | 0.2981 | 0.60 | 0.5475 |
| 9 months after treatment | Rank-sum test | 0.58 | 0.5609 | 0.72 | 0.4739 |
| 9 months after treatment-baseline | Rank-sum test | 0.07 | 0.9429 | −0.98 | 0.3254 |
| 12 months after treatment | Rank-sum test | 0.83 | 0.4050 | 1.11 | 0.2675 |
| 12 months after treatment-baseline | Rank-sum test | −0.16 | 0.8740 | −1.29 | 0.1967 |
| Follow-up | Rank-sum test | 0.62 | 0.5338 | 0.72 | 0.4703 |
| Follow-up-baseline | Rank-sum test | −0.95 | 0.3401 | −0.95 | 0.3441 |

TABLE 16 change of pain in different observations

| | FAS | | PP | |
|---|---|---|---|---|
| Items | Control group | trial group | Control group | trial group |
| | | Baseline | | |
| 0 | 480 (27.54%) | 446 (25.92%) | 404 (26.99%) | 359 (24.81%) |
| 2 | 672 (38.55%) | 693 (40.27%) | 566 (37.81%) | 561 (38.77%) |
| 4 | 561 (32.19%) | 544 (31.61%) | 501 (33.47%) | 495 (34.21%) |
| 6 | 30 (1.72%) | 38 (2.21%) | 26 (1.74%) | 32 (2.21%) |
| Total | 1743 | 1721 | 1497 | 1447 |
| | | 1 month after treatment | | |
| 0 | 637 (36.53%) | 604 (35.01%) | 540 (36.29%) | 499 (34.51%) |
| 2 | 640 (36.70%) | 652 (37.80%) | 536 (36.02%) | 533 (36.86%) |
| 4 | 451 (25.86%) | 458 (26.55%) | 400 (26.88%) | 405 (28.01%) |
| 6 | 16 (0.92%) | 11 (0.64%) | 12 (0.81%) | 9 (0.62%) |
| Total | 1744 | 1725 | 1488 | 1446 |
| | | 1 month after treatment-baseline | | |
| −6 | 7 (0.40%) | 12 (0.70%) | 6 (0.40%) | 10 (0.69%) |
| −4 | 70 (4.02%) | 63 (3.66%) | 61 (4.10%) | 56 (3.88%) |
| −2 | 231 (13.25%) | 252 (14.64%) | 198 (13.32%) | 213 (14.77%) |
| 0 | 1353 (77.62%) | 1295 (75.25%) | 1155 (77.67%) | 1092 (75.73%) |
| 2 | 67 (3.84%) | 80 (4.65%) | 55 (3.70%) | 60 (4.16%) |
| 4 | 15 (0.86%) | 19 (1.10%) | 12 (0.81%) | 11 (0.76%) |
| Total | 1743 | 1721 | 1487 | 1442 |
| Signed-rank (P) | −22991(0.0000) | −25059(0.0000) | −17174.0(0.0000) | −19115.5(0.0000) |
| | | 3 months after treatment | | |
| 0 | 697 (39.97%) | 657 (38.09%) | 595 (40.39%) | 543 (37.89%) |
| 2 | 635 (36.41%) | 665 (38.55%) | 522 (35.44%) | 548 (38.24%) |
| 4 | 402 (23.05%) | 392 (22.72%) | 349 (23.69%) | 335 (23.38%) |
| 6 | 10 (0.57%) | 11 (0.64%) | 7 (0.48%) | 7 (0.49%) |
| Total | 1744 | 1725 | 1473 | 1433 |
| | | 3 months after treatment-baseline | | |
| −6 | 8 (0.46%) | 9 (0.52%) | 7 (0.48%) | 7 (0.49%) |
| −4 | 89 (5.11%) | 102 (5.93%) | 77 (5.23%) | 89 (6.23%) |
| −2 | 333 (19.10%) | 312 (18.13%) | 287 (19.50%) | 268 (18.75%) |
| 0 | 1213 (69.59%) | 1197 (69.55%) | 1026 (69.70%) | 999 (69.91%) |
| 2 | 81 (4.65%) | 77 (4.47%) | 63 (4.28%) | 53 (3.71%) |
| 4 | 19 (1.09%) | 23 (1.34%) | 12 (0.82%) | 13 (0.91%) |
| 6 | 0 (0.00%) | 1 (0.06%) | | |
| Total | 1743 | 1721 | 1472 | 1429 |
| Signed-rank (P) | −44649 (0.0000) | −42845 (0.0000) | −34044.0 (0.0000) | −32957.0 (0.0000) |

TABLE 16-continued change of pain in different observations

| | FAS | | PP | |
|---|---|---|---|---|
| Items | Control group | trial group | Control group | trial group |
| | 6 months after treatment | | | |
| 0 | 780 (44.72%) | 726 (42.09%) | 671 (46.09%) | 596 (42.18%) |
| 2 | 616 (35.32%) | 655 (37.97%) | 506 (34.75%) | 543 (38.43%) |
| 4 | 340 (19.50%) | 333 (19.30%) | 274 (18.82%) | 269 (19.04%) |
| 6 | 8 (0.46%) | 11 (0.64%) | 5 (0.34%) | 5 (0.35%) |
| Total | 1744 | 1725 | 1456 | 1413 |
| | 6 months after treatment-baseline | | | |
| −6 | 10 (0.57%) | 14 (0.81%) | 9 (0.62%) | 11 (0.78%) |
| −4 | 120 (6.88%) | 115 (6.68%) | 107 (7.35%) | 101 (7.17%) |
| −2 | 403 (23.12%) | 405 (23.53%) | 352 (24.19%) | 348 (24.70%) |
| 0 | 1114 (63.91%) | 1081 (62.81%) | 923 (63.44%) | 887 (62.95%) |
| 2 | 83 (4.76%) | 82 (4.76%) | 58 (3.99%) | 53 (3.76%) |
| 4 | 13 (0.75%) | 23 (1.34%) | 6 (0.41%) | 8 (0.57%) |
| 6 | 0 (0.00%) | 1 (0.06%) | 0 (0.00%) | 1 (0.07%) |
| Total | 1743 | 1721 | 1455 | 1409 |
| Signed-rank (P) | −71668 (0.0000) | −69120 (0.0000) | −56168.0 (0.0000) | −53434.0 (0.0000) |
| | 9 months after treatment | | | |
| 0 | 825 (47.31%) | 777 (45.04%) | 707 (49.03%) | 640 (46.34%) |
| 2 | 617 (35.38%) | 641 (37.16%) | 501 (34.74%) | 514 (37.22%) |
| 4 | 293 (16.80%) | 293 (16.99%) | 230 (15.95%) | 223 (16.15%) |
| 6 | 9 (0.52%) | 14 (0.81%) | 4 (0.28%) | 4 (0.29%) |
| Total | 1744 | 1725 | 1442 | 1381 |
| | 9 months after treatment-baseline | | | |
| −6 | 11 (0.63%) | 15 (0.87%) | 10 (0.69%) | 12 (0.87%) |
| −4 | 143 (8.20%) | 145 (8.43%) | 127 (8.81%) | 129 (9.37%) |
| −2 | 450 (25.82%) | 430 (24.99%) | 396 (27.48%) | 365 (26.51%) |
| 0 | 1039 (59.61%) | 1026 (59.62%) | 840 (58.29%) | 815 (59.19%) |
| 2 | 85 (4.88%) | 78 (4.53%) | 59 (4.09%) | 49 (3.56%) |
| 4 | 15 (0.86%) | 23 (1.34%) | 9 (0.62%) | 6 (0.44%) |
| 6 | 0 (0.00%) | 4 (0.23%) | 0 (0.00%) | 1 (0.07%) |
| Total | 1743 | 1721 | 1441 | 1377 |
| Signed-rank (P) | −92083 (0.0000) | −84708 (0.0000) | −72287.0 (0.0000) | −65486.0 (0.0000) |
| | 12 months after treatment | | | |
| 0 | 910 (52.18%) | 850 (49.28%) | 788 (55.07%) | 706 (51.42%) |
| 2 | 589 (33.77%) | 606 (35.13%) | 469 (32.77%) | 481 (35.03%) |
| 4 | 237 (13.59%) | 254 (14.72%) | 173 (12.09%) | 183 (13.33%) |
| 6 | 8 (0.46%) | 15 (0.87%) | 1 (0.07%) | 3 (0.22%) |
| Total | 1744 | 1725 | 1431 | 1373 |
| | 12 months after treatment-baseline | | | |
| −6 | 12 (0.69%) | 16 (0.93%) | 10 (0.70%) | 13 (0.95%) |
| −4 | 182 (10.44%) | 170 (9.88%) | 165 (11.54%) | 153 (11.18%) |
| −2 | 489 (28.06%) | 471 (27.37%) | 433 (30.28%) | 403 (29.44%) |
| 0 | 976 (56.00%) | 972 (56.48%) | 774 (54.13%) | 761 (55.59%) |
| 2 | 76 (4.36%) | 68 (3.95%) | 46 (3.22%) | 37 (2.70%) |
| 4 | 8 (0.46%) | 19 (1.10%) | 2 (0.14%) | 1 (0.07%) |
| 6 | 0 (0.00%) | 5 (0.29%) | 0 (0.00%) | 1 (0.07%) |
| Total | 1743 | 1721 | 1430 | 1369 |
| Signed-rank (P) | −12E4 (0.0000) | −106E3 (0.0000) | −95582.0 (0.0000) | −83290.5 (0.0000) |
| | Follow-up | | | |
| 0 | 774 (53.64%) | 716 (51.70%) | 753 (53.48%) | 693 (51.37%) |
| 2 | 477 (33.06%) | 472 (34.08%) | 469 (33.31%) | 465 (34.47%) |
| 4 | 190 (13.17%) | 196 (14.15%) | 185 (13.14%) | 190 (14.08%) |
| 6 | 2 (0.14%) | 1 (0.07%) | 1 (0.07%) | 1 (0.07%) |
| Total | 1443 | 1385 | 1408 | 1349 |
| | Follow-up-baseline | | | |
| −6 | 12 (0.83%) | 13 (0.94%) | 12 (0.85%) | 12 (0.89%) |
| −4 | 165 (11.43%) | 162 (11.73%) | 162 (11.51%) | 158 (11.75%) |
| −2 | 418 (28.97%) | 405 (29.33%) | 409 (29.05%) | 394 (29.29%) |
| 0 | 783 (54.26%) | 748 (54.16%) | 762 (54.12%) | 732 (54.42%) |

TABLE 16-continued change of pain in different observations

| | FAS | | PP | |
| --- | --- | --- | --- | --- |
| Items | Control group | trial group | Control group | trial group |
| 2 | 53 (3.67%) | 40 (2.90%) | 53 (3.76%) | 37 (2.75%) |
| 4 | 11 (0.76%) | 13 (0.94%) | 9 (0.64%) | 12 (0.89%) |
| 6 | 1 (0.07%) | 0 (0.00%) | 1 (0.07%) | 0 (0.00%) |
| Total | 1443 | 1381 | 1408 | 1345 |
| Signed-rank (P) | −89749 (0.0000) | −84482 (0.0000) | −86649.0 (0.0000) | −79905.5 (0.0000) |

TABLE 17 test of change of pain in different observations

| | | FAS | | PP | |
| --- | --- | --- | --- | --- | --- |
| Items | test method | Statistic | P value | Statistic | P value |
| Baseline | Rank-sum test | 0.64 | 0.5250 | 1.22 | 0.2229 |
| 1 month after treatment | Rank-sum test | 0.70 | 0.4848 | 0.91 | 0.3621 |
| 1 month after treatment-baseline | Rank-sum test | −0.24 | 0.8121 | −0.68 | 0.4946 |
| 3 months after treatment | Rank-sum test | 0.71 | 0.4806 | 0.86 | 0.3910 |
| 3 months after treatment-baseline | Rank-sum test | −0.01 | 0.9895 | −0.48 | 0.6285 |
| 6 months after treatment | Rank-sum test | 1.18 | 0.2396 | 1.64 | 0.1004 |
| 6 months after treatment-baseline | Rank-sum test | 0.04 | 0.9698 | −0.23 | 0.8215 |
| 9 months after treatment | Rank-sum test | 1.20 | 0.2293 | 1.18 | 0.2368 |
| 9 months after treatment-baseline | Rank-sum test | 0.24 | 0.8095 | −0.25 | 0.7995 |
| 12 months after treatment | Rank-sum test | 1.84 | 0.0652 | 1.96 | 0.0500 |
| 12 months after treatment-baseline | Rank-sum test | 0.75 | 0.4553 | 0.27 | 0.7867 |
| Follow-up | Rank-sum test | 1.07 | 0.2840 | 1.14 | 0.2527 |
| Follow-up-baseline | Rank-sum test | −0.61 | 0.5420 | −0.52 | 0.6037 |

TABLE 18 change of dose of nitroglycerin in different observations

| | FAS | | PP | |
| --- | --- | --- | --- | --- |
| Items | Control group | Trial group | Control group | Trial group |
| | Baseline | | | |
| 0 | 927 (53.40%) | 881 (51.25%) | 792 (53.05%) | 733 (50.73%) |
| 1 | 1 (0.06%) | 1 (0.06%) | 1 (0.07%) | 1 (0.07%) |
| 2 | 562 (32.37%) | 590 (34.32%) | 482 (32.28%) | 495 (34.26%) |
| 4 | 172 (9.91%) | 175 (10.18%) | 155 (10.38%) | 153 (10.59%) |
| 6 | 74 (4.26%) | 72 (4.19%) | 63 (4.22%) | 63 (4.36%) |
| Total | 1736 | 1719 | 1493 | 1445 |
| | 1 month after treatment | | | |
| 0 | 1039 (59.78%) | 1000 (58.00%) | 884 (59.61%) | 840 (58.17%) |
| 1 | 5 (0.29%) | 2 (0.12%) | 4 (0.27%) | 1 (0.07%) |
| 2 | 503 (28.94%) | 548 (31.79%) | 436 (29.40%) | 456 (31.58%) |
| 4 | 133 (7.65%) | 122 (7.08%) | 111 (7.48%) | 103 (7.13%) |
| 6 | 58 (3.34%) | 52 (3.02%) | 48 (3.24%) | 44 (3.05%) |
| Total | 1738 | 1724 | 1483 | 1444 |
| | 1 month after treatment-baseline | | | |
| −6 | 9 (0.52%) | 17 (0.99%) | 8 (0.54%) | 16 (1.11%) |
| −4 | 37 (2.13%) | 42 (2.44%) | 34 (2.29%) | 35 (2.43%) |
| −2 | 198 (11.41%) | 198 (11.52%) | 171 (11.54%) | 164 (11.40%) |
| −3 | 1 (0.06%) | 0 (0.00%) | | |
| 0 | 1398 (80.53%) | 1361 (79.17%) | 1191 (80.36%) | 1155 (80.26%) |
| −1 | 0 (0.00%) | 1 (0.06%) | | |
| 1 | 3 (0.17%) | 0 (0.00%) | 3 (0.20%) | 0 (0.00%) |
| 2 | 68 (3.92%) | 82 (4.77%) | 56 (3.78%) | 55 (3.82%) |

TABLE 18-continued change of dose of nitroglycerin in different observations

| | FAS | | PP | |
|---|---|---|---|---|
| Items | Control group | Trial group | Control group | Trial group |
| 4 | 18 (1.04%) | 13 (0.76%) | 15 (1.01%) | 11 (0.76%) |
| 6 | 4 (0.23%) | 5 (0.29%) | 4 (0.27%) | 3 (0.21%) |
| Total | 1736 | 1719 | 1482 | 1439 |
| Signed-rank (P) | −12666 (0.0000) | −14773 (0.0000) | −9718.00 (0.0000) | −10692.5 (0.0000) |
| | | 3 months after treatment | | |
| 0 | 1079 (61.98%) | 1044 (60.52%) | 926 (62.95%) | 863 (60.43%) |
| 1 | 11 (0.63%) | 10 (0.58%) | 11 (0.75%) | 10 (0.70%) |
| 2 | 515 (29.58%) | 550 (31.88%) | 428 (29.10%) | 457 (32.00%) |
| 4 | 91 (5.23%) | 81 (4.70%) | 73 (4.96%) | 67 (4.69%) |
| 6 | 45 (2.58%) | 40 (2.32%) | 33 (2.24%) | 31 (2.17%) |
| Total | 1741 | 1725 | 1471 | 1428 |
| | | 3 months after treatment-baseline | | |
| −6 | 12 (0.69%) | 17 (0.99%) | 10 (0.68%) | 16 (1.13%) |
| −5 | 2 (0.12%) | 0 (0.00%) | 2 (0.14%) | 0 (0.00%) |
| −4 | 51 (2.94%) | 61 (3.55%) | 46 (3.14%) | 50 (3.52%) |
| −2 | 263 (15.15%) | 268 (15.59%) | 232 (15.81%) | 223 (15.68%) |
| −1 | 5 (0.29%) | 8 (0.47%) | 5 (0.34%) | 8 (0.56%) |
| 0 | 1306 (75.23%) | 1268 (73.76%) | 1101 (5.05%) | 1057 (74.33%) |
| 1 | 3 (0.17%) | 1 (0.06%) | 3 (0.20%) | 1 (0.07%) |
| 2 | 77 (4.44%) | 80 (4.65%) | 55 (3.75%) | 54 (3.80%) |
| 4 | 12 (0.69%) | 11 (0.64%) | 8 (0.55%) | 9 (0.63%) |
| 6 | 5 (0.29%) | 5 (0.29% | 5 (0.34%) | 4 (0.28%) |
| Total | 1736 | 1719 | 1467 | 1422 |
| Signed-rank (P) | −25905 (0.0000) | −29747 (0.0000) | −20832.0 (0.0000) | −21134.5 (0.0000) |
| | | 6 months after treatment | | |
| 0 | 1139 (65.38%) | 1091 (63.25%) | 976 (67.13%) | 901 (64.04%) |
| 1 | 15 (0.86%) | 32 (1.86%) | 15 (1.03%) | 32 (2.27%) |
| 2 | 492 (28.24%) | 499 (28.93%) | 405 (27.85%) | 406 (28.86%) |
| 4 | 63 (3.62%) | 60 (3.48%) | 40 (2.75%) | 37 (2.63%) |
| 6 | 33 (1.89%) | 43 (2.49%) | 18 (1.24%) | 31 (2.20%) |
| Total | 1742 | 1725 | 1454 | 1407 |
| | | 6 months after treatment-baseline | | |
| −6 | 18 (1.04%) | 22 (1.28%) | 15 (1.03%) | 20 (1.43%) |
| −5 | 3 (0.17%) | 1 (0.06%) | 3 (0.21%) | 1 (0.07%) |
| −4 | 70 (4.03%) | 77 (4.48%) | 64 (4.41%) | 66 (4.71%) |
| −3 | 0 (0.00%) | 2 (0.12%) | 0 (0.00%) | 2 (0.14%) |
| −2 | 321 (18.49%) | 311 (18.09%) | 282 (19.43%) | 260 (18.54%) |
| −1 | 4 (0.23%) | 17 (0.99%) | 4 (0.28%) | 17 (1.21%) |
| 0 | 1216 (70.05%) | 1176 (68.41%) | 1008 (69.47%) | 963 (68.69%) |
| 1 | 7 (0.40%) | 11 (0.64%) | 7 (0.48%) | 11 (0.78%) |
| 2 | 84 (4.84%) | 73 (4.25%) | 60 (4.14%) | 43 (3.07%) |
| 4 | 7 (0.40%) | 21 (1.22%) | 4 (0.28%) | 15 (1.07%) |
| 6 | 6 (0.35%) | 8 (0.47%) | 4 (0.28%) | 4 (0.29%) |
| Total | 1736 | 1719 | 1451 | 1402 |
| Signed-rank (P) | −43476 (0.0000) | −43631 (0.0000) | −34895.0 (0.0000) | −33070.5 (0.0000) |
| | | 9 months after treatment | | |
| 0 | 1169 (67.11%) | 1143 (66.26%) | 993 (68.96%) | 940 (68.31%) |
| 1 | 18 (1.03%) | 26 (1.51%) | 18 (1.25%) | 24 (1.74%) |
| 2 | 483 (27.73%) | 467 (27.07%) | 395 (27.43%) | 362 (26.31%) |
| 4 | 42 (2.41%) | 50 (2.90%) | 20 (1.39%) | 26 (1.89%) |
| 6 | 30 (1.72%) | 39 (2.26%) | 14 (0.97%) | 24 (1.74%) |
| Total | 1742 | 1725 | 1440 | 1376 |
| | | 9 months after treatment-baseline | | |
| −6 | 24 (1.38%) | 26 (1.51%) | 20 (1.39%) | 24 (1.75%) |
| −5 | 3 (0.17%) | 1 (0.06%) | 3 (0.21%) | 1 (0.07%) |
| −4 | 74 (4.26%) | 90 (5.24%) | 67 (4.67%) | 78 (5.69%) |
| −3 | 2 (0.12%) | 2 (0.12%) | 2 (0.14%) | 2 (0.15%) |
| −2 | 350 (20.16%) | 340 (19.78%) | 307 (21.38%) | 284 (20.71%) |
| −1 | 8 (0.46%) | 16 (0.93%) | 8 (0.56%) | 15 (1.09%) |
| 0 | 1171 (67.45%) | 1127 (65.56%) | 955 (66.50%) | 898 (65.50%) |
| 1 | 6 (0.35%) | 8 (0.47%) | 6 (0.42%) | 7 (0.51%) |
| 2 | 84 (4.84%) | 87 (5.06%) | 60 (4.18%) | 52 (3.79%) |

TABLE 18-continued change of dose of nitroglycerin in different observations

| | FAS | | PP | |
|---|---|---|---|---|
| Items | Control group | Trial group | Control group | Trial group |
| 4 | 8 (0.46%) | 13 (0.76%) | 4 (0.28%) | 5 (0.36%) |
| 6 | 6 (0.35%) | 9 (0.52%) | 4 (0.28%) | 5 (0.36%) |
| Total | 1736 | 1719 | 1436 | 1371 |
| Signed-rank (P) | −53222 (0.0000) | −55218 (0.0000) | −42481.5 (0.0000) | −41759.0 (0.0000) |
| 12 months after treatment | | | | |
| 0 | 1247 (71.58%) | 1200 (69.57%) | 1069 (74.81%) | 989 (72.30%) |
| 1 | 19 (1.09%) | 19 (1.10%) | 19 (1.33%) | 19 (1.39%) |
| 2 | 411 (23.59%) | 427 (24.75%) | 317 (22.18%) | 321 (23.46%) |
| 4 | 36 (2.07%) | 47 (2.72%) | 13 (0.91%) | 21 (1.54%) |
| 6 | 29 (1.66%) | 32 (1.86%) | 11 (0.77%) | 18 (1.32%) |
| Total | 1742 | 1725 | 1429 | 1368 |
| 12 months after treatment-baseline | | | | |
| −6 | 32 (1.84%) | 31 (1.80%) | 27 (1.89%) | 28 (2.05%) |
| −5 | 1 (0.06%) | 0 (0.00%) | 1 (0.07%) | 0 (0.00%) |
| −4 | 86 (4.95%) | 97 (5.64%) | 78 (5.47%) | 83 (6.09%) |
| −3 | 1 (0.06%) | 0 (0.00%) | 1 (0.07%) | 0 (0.00%) |
| −2 | 378 (21.77%) | 382 (22.22%) | 333 (23.37%) | 323 (23.70%) |
| −1 | 9 (0.52%) | 13 (0.76%) | 9 (0.63%) | 13 (0.95%) |
| 0 | 1138 (65.55%) | 1084 (63.06%) | 921 (64.63%) | 855 (62.73%) |
| 1 | 9 (0.52%) | 5 (0.29%) | 9 (0.63%) | 5 (0.37%) |
| 2 | 69 (3.97%) | 85 (4.94%) | 41 (2.88%) | 49 (3.60%) |
| 4 | 7 (0.40%) | 16 (0.93%) | 1 (0.07%) | 5 (0.37%) |
| 6 | 6 (0.35%) | 6 (0.35%) | 4 (0.28%) | 2 (0.15%) |
| Total | 1736 | 1719 | 1425 | 1363 |
| Signed-rank (P) | −65699 (0.0000) | −67124 (0.0000) | −52730.0 (0.0000) | −51415.5 (0.0000) |
| Follow-up | | | | |
| 0 | 1069 (74.24%) | 1017 (73.80%) | 1044 (74.31%) | 989 (73.70%) |
| 1 | 13 (0.90%) | 16 (1.16%) | 13 (0.93%) | 16 (1.19%) |
| 2 | 334 (23.19%) | 316 (22.93%) | 325 (23.13%) | 309 (23.03%) |
| 4 | 15 (1.04%) | 16 (1.16%) | 14 (1.00%) | 16 (1.19%) |
| 6 | 9 (0.63%) | 13 (0.94%) | 9 (0.64%) | 12 (0.89%) |
| Total | 1440 | 1378 | 1405 | 1342 |
| Follow-up-baseline | | | | |
| −6 | 27 (1.88%) | 31 (2.26%) | 26 (1.86%) | 30 (2.24%) |
| −5 | 2 (0.14%) | 3 (0.22%) | 2 (0.14%) | 3 (0.22%) |
| −4 | 92 (6.41%) | 95 (6.92%) | 90 (6.42%) | 91 (6.81%) |
| −3 | 2 (0.14%) | 1 (0.07%) | 2 (0.14%) | 1 (0.07%) |
| −2 | 313 (21.81%) | 334 (24.33%) | 309 (22.06%) | 322 (24.08%) |
| −1 | 6 (0.42%) | 6 (0.44%) | 6 (0.43%) | 6 (0.45%) |
| 0 | 924 (64.39%) | 832 (60.60%) | 899 (64.17%) | 815 (60.96%) |
| 1 | 4 (0.28%) | 5 (0.36%) | 4 (0.29%) | 5 (0.37%) |
| 2 | 58 (4.04%) | 61 (4.44%) | 56 (4.00%) | 60 (4.49%) |
| 4 | 4 (0.28%) | 3 (0.22%) | 4 (0.29%) | 2 (0.15%) |
| 6 | 3 (0.21%) | 2 (0.15%) | 3 (0.21%) | 2 (0.15%) |
| Total | 1435 | 1373 | 1401 | 1337 |
| Signed-rank (P) | −50803 (0.0000) | −58107 (0.0000) | −49134.5 (0.0000) | −54176.5 (0.0000) |

TABLE 19 test of change of nitroglycerin dose in different observations

| | | FAS | | PP | |
|---|---|---|---|---|---|
| Items | test method | Statistic | P value | Statistic | P value |
| Baseline | Rank-sum test | 1.08 | 0.2806 | 1.11 | 0.2656 |
| 1 month after treatment | Rank-sum test | 0.74 | 0.4590 | 0.60 | 0.5469 |
| 1 month after treatment-baseline | Rank-sum test | −0.39 | 0.6930 | −0.70 | 0.4825 |
| 3 months after treatment | Rank-sum test | 0.63 | 0.5274 | 1.22 | 0.2225 |
| 3 months after treatment-baseline | Rank-sum test | −0.91 | 0.3643 | −0.53 | 0.5993 |
| 6 months after treatment | Rank-sum test | 1.17 | 0.2433 | 1.63 | 0.1030 |
| 6 months after treatment-baseline | Rank-sum test | −0.30 | 0.7667 | −0.34 | 0.7302 |

TABLE 19-continued test of change of nitroglycerin dose in different observations

| Items | test method | FAS Statistic | FAS P value | PP Statistic | PP P value |
|---|---|---|---|---|---|
| 9 months after treatment | Rank-sum test | 0.63 | 0.5312 | 0.50 | 0.6178 |
| 9 months after treatment-baseline | Rank-sum test | −0.30 | 0.7663 | −0.72 | 0.4731 |
| 12 months after treatment | Rank-sum test | 1.40 | 0.1613 | 1.65 | 0.0988 |
| 12 months after treatment-baseline | Rank-sum test | −0.14 | 0.8891 | −0.44 | 0.6567 |
| Follow-up | Rank-sum test | 0.29 | 0.7728 | 0.39 | 0.6974 |
| Follow-up-baseline | Rank-sum test | −1.62 | 0.1059 | −1.31 | 0.1917 |

1.6.4.3 TCM symptom score

Analysis method was referred to the section of anginal pectoris.

TABLE 20 change of total score of TCM symptom in different observations

| Items | FAS Control group | FAS Trial group | PP Control group | PP Trial group |
|---|---|---|---|---|
| Baseline | | | | |
| N (Missing) | 1710 (49) | 1689 (57) | 1471 (29) | 1419 (37) |
| Mean (SD) | 13.83 (7.27) | 13.98 (7.06) | 13.96 (7.25) | 14.36 (7.08) |
| Min, Max | 0.00, 37.00 | 0.00, 36.00 | 0.00, 37.00 | 0.00, 36.00 |
| Md (Q3-Q1) | 13.00 (10.00) | 13.00 (10.00) | 13.00 (11.00) | 14.00 (9.00) |
| 1 month after treatment | | | | |
| N (Missing) | 1717 (42) | 1699 (47) | 1467 (33) | 1423 (33) |
| Mean (SD) | 11.84 (7.16) | 11.96 (7.05) | 11.93 (7.18) | 12.20 (7.15) |
| Min, Max | 0.00, 34.00 | 0.00, 37.00 | 0.00, 34.00 | 0.00, 37.00 |
| Md (Q3-Q1) | 11.00 (9.00) | 11.00 (9.00) | 11.00 (10.00) | 12.00 (10.00) |
| 1 month after treatment-baseline | | | | |
| N (Missing) | 1710 (49) | 1689 (57) | 1462 (38) | 1414 (42) |
| Mean (SD) | −1.96 (4.63) | −1.99 (4.58) | −2.00 (4.58) | −2.14 (4.52) |
| Min, Max | −33.00, 24.00 | −25.00, 20.00 | −28.00, 24.00 | −25.00, 19.00 |
| Md (Q3-Q1) | 0.00 (3.00) | 0.00 (3.00) | −1.00 (3.00) | 0.00 (4.00) |
| Pairing t-test (P) | −17.50 (0.0000) | −17.85 (0.0000) | −16.65 (0.0000) | −17.82 (0.0000) |
| 3 months after treatment | | | | |
| N (Missing) | 1717 (42) | 1700 (46) | 1447 (53) | 1408 (48) |
| Mean (SD) | 10.90 (6.88) | 11.05 (6.84) | 10.88 (6.85) | 11.17 (6.84) |
| Min, Max | 0.00, 33.00 | 0.00, 36.00 | 0.00, 33.00 | 0.00, 34.00 |
| Md (Q3-Q1) | 10.00 (9.00) | 11.00 (9.00) | 10.00 (9.00) | 11.00 (9.00) |
| 3 month after treatment-baseline | | | | |
| N (Missing) | 1710 (49) | 1689 (57) | 1444 (56) | 1400 (56) |
| Mean (SD) | −2.91 (5.22) | −2.91 (5.16) | −3.05 (5.19) | −3.18 (5.03) |
| Min, Max | −33.00, 19.00 | −27.00, 19.00 | −28.00, 19.00 | −27.00, 17.00 |
| Md (Q3-Q1) | −2.00 (5.00) | −2.00 (5.00) | −2.00 (5.00) | −2.00 (6.00) |
| Pairing t-test (P) | −23.05 (0.0000) | −23.16 (0.0000) | −22.32 (0.0000) | −23.65 (0.0000) |
| 6 months after treatment | | | | |
| N (Missing) | 1718 (41) | 1700 (46) | 1430 (70) | 1388 (68) |
| Mean (SD) | 10.04 (6.65) | 10.15 (6.49) | 9.79 (6.47) | 10.10 (6.33) |
| Min, Max | 0.00, 34.00 | 0.00, 36.00 | 0.00, 34.00 | 0.00, 36.00 |
| Md (Q3-Q1) | 9.00 (9.00) | 10.00 (7.00) | 9.00 (8.00) | 10.00 (7.00) |
| 6 months after treatment-baseline | | | | |
| N (Missing) | 1710 (49) | 1689 (57) | 1427 (73) | 1381 (75) |
| Mean (SD) | −3.76 (5.57) | −3.81 (5.69) | −4.11 (5.49) | −4.26 (5.48) |
| Min, Max | −33.00, 19.00 | −26.00, 27.00 | −28.00, 19.00 | −26.00, 27.00 |
| Md (Q3-Q1) | −3.00 (6.00) | −3.00 (6.00) | −3.00 (6.00) | −3.00 (6.00) |
| Pairing t-test (P) | −27.95 (0.0000) | −27.52 (0.0000) | −28.25 (0.0000) | −28.88 (0.0000) |
| 9 months after treatment | | | | |
| N (Missing) | 1718 (41) | 1700 (46) | 1416 (84) | 1360 (96) |
| Mean (SD) | 9.29 (6.35) | 9.31 (6.27) | 8.88 (6.04) | 8.98 (5.93) |

TABLE 20-continued change of total score of TCM symptom in different observations

| | FAS | | PP | |
|---|---|---|---|---|
| Items | Control group | Trial group | Control group | Trial group |
| Min, Max | 0.00, 37.00 | 0.00, 36.00 | 0.00, 37.00 | 0.00, 36.00 |
| Md (Q3-Q1) | 8.00 (8.00) | 9.00 (8.00) | 8.00 (7.00) | 9.00 (7.00) |
| | 9 months after treatment-baseline | | | |
| N (Missing) | 1710 (49) | 1689 (57) | 1412 (88) | 1354 (102) |
| Mean (SD) | −4.52 (5.90) | −4.65 (6.15) | −5.04 (5.80) | −5.36 (5.70) |
| Min, Max | −33.00, 15.00 | −28.00, 27.00 | 2−8.00, 15.00 | −28.00, 26.00 |
| Md (Q3-Q1) | −4.00 (8.00) | −4.00 (7.00) | −4.00 (7.00) | −5.00 (7.00) |
| Pairing t-test (P) | −31.68 (0.0000) | −31.09 (0.0000) | −32.62 (0.0000) | −34.56 (0.0000) |
| | 12 months after treatment | | | |
| N (Missing) | 1718 (41) | 1700 (46) | 1403 (97) | 1350 (106) |
| Mean (SD) | 8.41 (6.11) | 8.42 (5.97) | 7.81 (5.56) | 7.84 (5.34) |
| Min, Max | 0.00, 37.00 | 0.00, 36.00 | 0.00, 28.00 | 0.00, 28.00 |
| Md (Q3-Q1) | 8.00 (8.00) | 8.00 (8.00) | 7.00 (7.00) | 8.00 (8.00) |
| | 12 months after treatment-baseline | | | |
| N (Missing) | 1710 (49) | 1689 (57) | 1399 (101) | 1344 (112) |
| Mean (SD) | −5.39 (6.23) | −5.54 (6.49) | −6.09 (6.07) | −6.54 (5.84) |
| Min, Max | −33.00, 18.00 | −28.00, 27.00 | −28.00, 18.00 | −28.00, 15.00 |
| Md (Q3-Q1) | −5.00 (8.00) | −5.00 (8.00) | −5.00 (8.00) | −6.00 (8.00) |
| Pairing t-test (P) | −35.76 (0.0000) | −35.06 (0.0000) | −37.53 (0.0000) | −41.04 (0.0000) |
| | Follow-up | | | |
| N (Missing) | 1429 (330) | 1379 (367) | 1395 (105) | 1343 (113) |
| Mean (SD) | 7.71 (6.03) | 7.85 (5.94) | 7.73 (6.04) | 7.88 (5.92) |
| Min, Max | 0.00, 32.00 | 0.00, 33.00 | 0.00, 32.00 | 0.00, 33.00 |
| Md (Q3-Q1) | 7.00 (7.00) | 7.00 (8.00) | 7.00 (7.00) | 7.00 (8.00) |
| | Follow-up-baseline | | | |
| N (Missing) | 1425 (334) | 1373 (373) | 1391 (109) | 1337 (119) |
| Mean (SD) | −6.18 (6.52) | −6.48 (6.17) | −6.16 (6.52) | −6.45 (6.15) |
| Min, Max | −29.00, 27.00 | −28.00, 24.00 | −29.00, 27.00 | −28.00, 24.00 |
| Md (Q3-Q1) | −5.00 (8.00) | −6.00 (8.00) | −5.00 (8.00) | −6.00 (8.00) |
| Pairing t-test (P) | −35.76 (0.0000) | −38.90 (0.0000) | −35.23 (0.0000) | −38.34 (0.0000) |

TABLE 21

Distribution of total score of TCM symptom in different observations

| | FAS | | PP | |
|---|---|---|---|---|
| Items | Control group | Trial group | Control group | Trial group |
| | Baseline | | | |
| Mild | 828 (48.48%) | 772 (45.82%) | 701 (47.69%) | 617 (43.57%) |
| Medium | 817 (47.83%) | 855 (50.74%) | 717 (48.78%) | 750 (52.97%) |
| Severe | 63 (3.69%) | 58 (3.44%) | 52 (3.54%) | 49 (3.46%) |
| Total | 1708 | 1685 | 1470 | 1416 |
| | 1 month after treatment | | | |
| Mild | 989 (58.76%) | 975 (58.24%) | 847 (57.93%) | 814 (57.24%) |
| Medium | 675 (40.11%) | 673 (40.20%) | 600 (41.04%) | 586 (41.21%) |
| Severe | 19 (1.13%) | 26 (1.55%) | 15 (1.03%) | 22 (1.55%) |
| Total | 1683 | 1674 | 1462 | 1422 |
| | 3 months after treatment | | | |
| Mild | 1066 (65.56%) | 1064 (65.80%) | 946 (65.38%) | 911 (64.84%) |
| Medium | 546 (33.58%) | 538 (33.27%) | 489 (33.79%) | 481 (34.23%) |
| Severe | 14 (0.86%) | 15 (0.93%) | 12 (0.83%) | 13 (0.93%) |
| Total | 1626 | 1617 | 1447 | 1405 |

TABLE 21-continued

Distribution of total score of TCM symptom in different observations

| | FAS | | PP | |
|---|---|---|---|---|
| Items | Control group | Trial group | Control group | Trial group |
| | 6 months after treatment | | | |
| Mild | 1133 (72.63%) | 1110 (72.08%) | 1044 (73.11%) | 996 (71.76%) |
| Medium | 418 (26.79%) | 420 (27.27%) | 377 (26.40%) | 384 (27.67%) |
| Severe | 9 (0.58%) | 10 (0.65%) | 7 (0.49%) | 8 (0.58%) |
| Total | 1560 | 1540 | 1428 | 1388 |
| | 9 months after treatment | | | |
| Mild | 1149 (76.70%) | 1113 (77.24%) | 1088 (76.94%) | 1045 (77.06%) |
| Medium | 345 (23.03%) | 323 (22.41%) | 323 (22.84%) | 307 (22.64%) |
| Severe | 4 (0.27%) | 5 (0.35%) | 3 (0.21%) | 4 (0.29%) |
| Total | 1498 | 1441 | 1414 | 1356 |
| | 12 months after treatment | | | |
| Mild | 1205 (83.62%) | 1141 (82.38%) | 1172 (83.59%) | 1108 (82.20%) |
| Medium | 235 (16.31%) | 241 (17.40%) | 229 (16.33%) | 237 (17.58%) |
| Severe | 1 (0.07%) | 3 (0.22%) | 1 (0.07%) | 3 (0.22%) |
| Total | 1441 | 1385 | 1402 | 1348 |
| | Follow-up | | | |
| Mild | 1205 (84.50%) | 1148 (83.37%) | 1177 (84.55%) | 1116 (83.22%) |
| Medium | 218 (15.29%) | 226 (16.41%) | 212 (15.23%) | 222 (16.55%) |
| Severe | 3 (0.21%) | 3 (0.22%) | 3 (0.22%) | 3 (0.22%) |
| Total | 1426 | 1377 | 1392 | 1341 |

TABLE 22

Test of distribution of total score of TCM symptom in different observations

| | | FAS | | PP | |
|---|---|---|---|---|---|
| Items | Test method | Statistic | P value | Statistic | P value |
| Baseline | Rank-sum test | 1.40 | 0.1628 | 2.08 | 0.0378 |
| 1 month after treatment | Rank-sum test | 0.40 | 0.6866 | 0.49 | 0.6253 |
| 3 months after treatment | Rank-sum test | −0.13 | 0.8971 | 0.32 | 0.7520 |
| 6 months after treatment | Rank-sum test | 0.35 | 0.7245 | 0.81 | 0.4172 |
| 9 months after treatment | Rank-sum test | −0.33 | 0.7401 | −0.06 | 0.9498 |
| 12 months after treatment | Rank-sum test | 0.89 | 0.3716 | 0.99 | 0.3219 |
| Follow-up | Rank-sum test | 0.82 | 0.4149 | 0.95 | 0.3439 |

TABLE 23 change of chest pain in different observations

| | FAS | | PP | |
|---|---|---|---|---|
| | Control group | Trial group | Control group | Trial group |
| | Baseline | | | |
| 0 | 473 (27.68%) | 443 (26.26%) | 398 (27.07%) | 352 (24.82%) |
| 3 | 641 (37.51%) | 679 (40.25%) | 546 (37.14%) | 562 (39.63%) |
| 6 | 568 (33.24%) | 534 (31.65%) | 505 (34.35%) | 476 (33.57%) |
| 9 | 27 (1.58%) | 31 (1.84%) | 21 (1.43%) | 28 (1.97%) |
| Total | 1709 | 1687 | 1470 | 1418 |
| | 1 month after treatment | | | |
| 0 | 608 (35.41%) | 579 (34.08%) | 515 (35.13%) | 471 (33.15%) |
| 3 | 635 (36.98%) | 663 (39.02%) | 537 (36.63%) | 551 (38.78%) |
| 6 | 461 (26.85%) | 445 (26.19%) | 406 (27.69%) | 390 (27.45%) |
| 9 | 13 (0.76%) | 12 (0.71%) | 8 (0.55%) | 9 (0.63%) |
| Total | 1717 | 1699 | 1466 | 1421 |

TABLE 23-continued change of chest pain in different observations

| | FAS | | PP | |
|---|---|---|---|---|
| | Control group | Trial group | Control group | Trial group |
| | 1 month after treatment-baseline | | | |
| −9 | 0 (0.00%) | 1 (0.06%) | 0 (0.00%) | 1 (0.07%) |
| −6 | 16 (0.94%) | 19 (1.13%) | 12 (0.82%) | 11 (0.78%) |
| −3 | 59 (3.45%) | 64 (3.79%) | 50 (3.42%) | 46 (3.26%) |
| 0 | 1344 (78.64%) | 1302 (77.18%) | 1146 (78.49%) | 1097 (77.75%) |
| 3 | 226 (13.22%) | 243 (14.40%) | 197 (13.49%) | 204 (14.46%) |
| 6 | 60 (3.51%) | 54 (3.20%) | 52 (3.56%) | 48 (3.40%) |
| 9 | 4 (0.23%) | 4 (0.24%) | 3 (0.21%) | 4 (0.28%) |
| Total | 1709 | 1687 | 1460 | 1411 |
| Signed-rank (P) | 19785 (0.0000) | 20378 (0.0000) | 15173.50 (0.0000) | 15562.50 (0.0000) |
| | 3 months after treatment | | | |
| 0 | 656 (38.21%) | 627 (36.88%) | 550 (38.01%) | 502 (35.68%) |
| 3 | 643 (37.45%) | 669 (39.35%) | 535 (36.97%) | 562 (39.94%) |
| 6 | 410 (23.88%) | 391 (23.00%) | 356 (24.60%) | 337 (23.95%) |
| 9 | 8 (0.47%) | 13 (0.76%) | 6 (0.41%) | 6 (0.43%) |
| Total | 1717 | 1700 | 1447 | 1407 |
| | 3 months after treatment-baseline | | | |
| −6 | 20 (1.17%) | 22 (1.30%) | 14 (0.97%) | 12 (0.86%) |
| −9 | 0 (0.00%) | 1 (0.06%) | | |
| −3 | 79 (4.62%) | 75 (4.45%) | 64 (4.44%) | 52 (3.72%) |
| 0 | 1203 (70.39%) | 1186 (70.30%) | 1019 (70.62%) | 993 (71.03%) |
| 3 | 325 (19.02%) | 329 (19.50%) | 279 (19.33%) | 278 (19.89%) |
| 6 | 76 (4.45%) | 71 (4.21%) | 63 (4.37%) | 61 (4.36%) |
| 9 | 6 (0.35%) | 3 (0.18%) | 4 (0.28%) | 2 (0.14%) |
| Total | 1709 | 1687 | 1443 | 1398 |
| Signed-rank (P) | 39088 (0.0000) | 37267 (0.0000) | 28694.00 (0.0000) | 28097.50 (0.0000) |
| | 6 months after treatment | | | |
| 0 | 729 (42.43%) | 692 (40.71%) | 613 (42.93%) | 549 (39.61%) |
| 3 | 638 (37.14%) | 664 (39.06%) | 539 (37.75%) | 561 (40.48%) |
| 6 | 345 (20.08%) | 334 (19.65%) | 272 (19.05%) | 272 (19.62%) |
| 9 | 6 (0.35%) | 10 (0.59%) | 4 (0.28%) | 4 (0.29%) |
| Total | 1718 | 1700 | 1428 | 1386 |
| | 6 months after treatment-baseline | | | |
| −9 | 0 (0.00%) | 1 (0.06%) | 0 (0.00%) | 1 (0.07%) |
| −6 | 13 (0.76%) | 22 (1.30%) | 5 (0.35%) | 9 (0.65%) |
| −3 | 80 (4.68%) | 87 (5.16%) | 57 (4.00%) | 61 (4.43%) |
| 0 | 1104 (64.60%) | 1060 (62.83%) | 919 (64.54%) | 869 (63.06%) |
| 3 | 405 (23.70%) | 420 (24.90%) | 352 (24.72%) | 355 (25.76%) |
| 6 | 101 (5.91%) | 92 (5.45%) | 86 (6.04%) | 79 (5.73%) |
| 9 | 6 (0.35%) | 5 (0.30%) | 5 (0.35%) | 4 (0.29%) |
| Total | 1709 | 1687 | 1424 | 1378 |
| Signed-rank (P) | 65165 (0.0000) | 63298 (0.0000) | 49922.50 (0.0000) | 47527.50 (0.0000) |
| | 9 months after treatment | | | |
| 0 | 791 (46.04%) | 741 (43.59%) | 661 (46.71%) | 594 (43.68%) |
| 3 | 618 (35.97%) | 653 (38.41%) | 519 (36.68%) | 536 (39.41%) |
| 6 | 305 (17.75%) | 291 (17.12%) | 233 (16.47%) | 225 (16.54%) |
| 9 | 4 (0.23%) | 15 (0.88%) | 2 (0.14%) | 5 (0.37%) |
| Total | 1718 | 1700 | 1415 | 1360 |
| | 9 months after treatment-baseline | | | |
| −9 | 0 (0.00%) | 6 (0.36%) | 0 (0.00%) | 3 (0.22%) |
| −6 | 13 (0.76%) | 22 (1.30%) | 7 (0.50%) | 6 (0.44%) |
| −3 | 81 (4.74%) | 73 (4.33%) | 58 (4.11%) | 49 (3.62%) |
| 0 | 1022 (59.80%) | 1005 (59.57%) | 826 (58.58%) | 803 (59.35%) |
| 3 | 463 (27.09%) | 465 (27.56%) | 409 (29.01%) | 392 (28.97%) |
| 6 | 124 (7.26%) | 111 (6.58%) | 106 (7.52%) | 96 (7.10%) |
| 9 | 6 (0.35%) | 5 (0.30%) | 4 (0.28%) | 4 (0.30%) |
| Total | 1709 | 1687 | 1410 | 1353 |
| Signed-rank (P) | 88123 (0.0000) | 79406 (0.0000) | 68170.00 (0.0000) | 60337.50 (0.0000) |

TABLE 23-continued change of chest pain in different observations

| | FAS | | PP | |
|---|---|---|---|---|
| | Control group | Trial group | Control group | Trial group |
| | 12 months after treatment | | | |
| 0 | 858 (49.94%) | 820 (48.24%) | 725 (51.67%) | 666 (49.33%) |
| 3 | 607 (35.33%) | 613 (36.06%) | 501 (35.71%) | 496 (36.74%) |
| 6 | 248 (14.44%) | 252 (14.82%) | 176 (12.54%) | 186 (13.78%) |
| 9 | 5 (0.29%) | 15 (0.88%) | 1 (0.07%) | 2 (0.15%) |
| Total | 1718 | 1700 | 1403 | 1350 |
| | 12 months after treatment-baseline | | | |
| −6 | 9 (0.53%) | 20 (1.19%) | 2 (0.14%) | 4 (0.30%) |
| −9 | 0 (0.00%) | 6 (0.36%) | | |
| −3 | 70 (4.10%) | 64 (3.79%) | 45 (3.22%) | 36 (2.68%) |
| 0 | 962 (56.29%) | 948 (56.19%) | 760 (54.36%) | 750 (55.85%) |
| 3 | 511 (29.90%) | 501 (29.70%) | 455 (32.55%) | 422 (31.42%) |
| 6 | 150 (8.78%) | 141 (8.36%) | 131 (9.37%) | 125 (9.31%) |
| 9 | 7 (0.41%) | 7 (0.41%) | 5 (0.36%) | 6 (0.45%) |
| Total | 1709 | 1687 | 1398 | 1343 |
| Signed-rank (P) | 113370 (0.000) | 101285 (0.0000) | 89514.00 (0.0000) | 77706.50 (0.0000) |
| | Follow-up | | | |
| 0 | 754 (52.84%) | 698 (50.73%) | 733 (52.62%) | 675 (50.37%) |
| 2 | 1 (0.07%) | 0 (0.00%) | 1 (0.07%) | 0 (0.00%) |
| 3 | 479 (33.57%) | 488 (35.47%) | 472 (33.88%) | 479 (35.75%) |
| 6 | 192 (13.45%) | 188 (13.66%) | 186 (13.35%) | 184 (13.73%) |
| 9 | 1 (0.07%) | 2 (0.15%) | 1 (0.07%) | 2 (0.15%) |
| Total | 1427 | 1376 | 1393 | 1340 |
| | Follow-up-baseline | | | |
| −9 | 1 (0.07%) | 1 (0.07%) | 1 (0.07%) | 1 (0.08%) |
| −6 | 11 (0.77%) | 11 (0.80%) | 9 (0.65%) | 10 (0.75%) |
| −3 | 47 (3.31%) | 44 (3.21%) | 47 (3.39%) | 41 (3.08%) |
| −2 | 1 (0.07%) | 0 (0.00%) | 1 (0.07%) | 0 (0.00%) |
| 0 | 769 (54.08%) | 737 (53.83%) | 750 (54.03%) | 723 (54.24%) |
| 3 | 426 (29.96%) | 424 (30.97%) | 417 (30.04%) | 411 (30.83%) |
| 6 | 158 (11.11%) | 142 (10.37%) | 155 (11.17%) | 137 (10.28%) |
| 9 | 9 (0.63%) | 10 (0.73%) | 8 (0.58%) | 10 (0.75%) |
| Total | 1422 | 1369 | 1388 | 1333 |
| Signed-rank (P) | 88781 (0.0000) | 83074 (0.0000) | 85383.50 (0.0000) | 78026.00 (0.0000) |

TABLE 24 test of change of chest pain in different observations

| Items | Test method | FAS Statistic | FAS P value | PP Statistic | PP P value |
|---|---|---|---|---|---|
| Baseline | Rank-sum test | 0.04 | 0.9672 | 0.73 | 0.4677 |
| 1 month after treatment | Rank-sum test | 0.27 | 0.7887 | 0.66 | 0.5063 |
| 1 month after treatment-baseline | Rank-sum test | 0.18 | 0.8592 | 0.59 | 0.5581 |
| 3 months after treatment | Rank-sum test | 0.39 | 0.6979 | 0.67 | 0.5031 |
| 3 months after treatment-baseline | Rank-sum test | −0.04 | 0.9683 | 0.56 | 0.5785 |
| 6 months after treatment | Rank-sum test | 0.71 | 0.4754 | 1.49 | 0.1367 |
| 6 months after treatment-baseline | Rank-sum test | −0.19 | 0.8458 | −0.04 | 0.9667 |
| 9 months after treatment | Rank-sum test | 1.17 | 0.2416 | 1.35 | 0.1761 |
| 9 months after treatment-baseline | Rank-sum test | −0.49 | 0.6257 | −0.18 | 0.8581 |
| 12 months after treatment | Rank-sum test | 1.13 | 0.2603 | 1.35 | 0.1779 |
| 12 months after treatment-baseline | Rank-sum test | −0.66 | 0.5079 | −0.36 | 0.7154 |
| Follow-up | Rank-sum test | 1.01 | 0.3120 | 1.10 | 0.2717 |
| Follow-up-baseline | Rank-sum test | 0.07 | 0.9467 | −0.03 | 0.9763 |

TABLE 25 change of chest tightness in different observations

| | FAS | | PP | |
|---|---|---|---|---|
| Items | Control group | Trial group | Control group | Trial group |
| Baseline | | | | |
| 0 | 473 (27.68%) | 443 (26.26%) | 398 (27.07%) | 352 (24.82%) |
| 3 | 641 (37.51%) | 679 (40.25%) | 546 (37.14%) | 562 (39.63%) |
| 6 | 568 (33.24%) | 534 (31.65%) | 505 (34.35%) | 476 (33.57%) |
| 9 | 27 (1.58%) | 31 (1.84%) | 21 (1.43%) | 28 (1.97%) |
| Total | 1709 | 1687 | 1470 | 1418 |
| 1 month after treatment | | | | |
| 0 | 608 (35.41%) | 579 (34.08%) | 515 (35.13%) | 471 (33.15%) |
| 3 | 635 (36.98%) | 663 (39.02%) | 537 (36.63%) | 551 (38.78%) |
| 6 | 461 (26.85%) | 445 (26.19%) | 406 (27.69%) | 390 (27.45%) |
| 9 | 13 (0.76%) | 12 (0.71%) | 8 (0.55%) | 9 (0.63%) |
| Total | 1717 | 1699 | 1466 | 1421 |
| 1 month after treatment-baseline | | | | |
| −6 | 7 (0.41%) | 6 (0.36%) | 6 (0.41%) | 3 (0.21%) |
| −3 | 76 (4.45%) | 79 (4.69%) | 62 (4.25%) | 58 (4.11%) |
| 0 | 1302 (76.18%) | 1273 (75.50%) | 1110 (76.03%) | 1067 (75.57%) |
| 3 | 298 (17.44%) | 298 (17.67%) | 259 (17.74%) | 259 (18.34%) |
| 6 | 21 (1.23%) | 26 (1.54%) | 19 (1.30%) | 21 (1.49%) |
| 9 | 5 (0.29%) | 4 (0.24%) | 4 (0.27%) | 4 (0.28%) |
| Total | 1709 | 1686 | 1460 | 1412 |
| Signed-rank (P) | 24545 (0.0000) | 25454 (0.0000) | 18726.50 (0.0000) | 19632.00 (0.0000) |
| 3 months after treatment | | | | |
| 0 | 656 (38.21%) | 627 (36.88%) | 550 (38.01%) | 502 (35.68%) |
| 3 | 643 (37.45%) | 669 (39.35%) | 535 (36.97%) | 562 (39.94%) |
| 6 | 410 (23.88%) | 391 (23.00%) | 356 (24.60%) | 337 (23.95%) |
| 9 | 8 (0.47%) | 13 (0.76%) | 6 (0.41%) | 6 (0.43%) |
| Total | 1717 | 1700 | 1447 | 1407 |
| 3 months after treatment-baseline | | | | |
| −9 | 1 (0.06%) | 0 (0.00%) | 1 (0.07%) | 0 (0.00%) |
| −6 | 8 (0.47%) | 8 (0.47%) | 6 (0.42%) | 4 (0.29%) |
| −3 | 85 (4.97%) | 92 (5.46%) | 70 (4.85%) | 62 (4.43%) |
| 0 | 1190 (69.63%) | 1141 (67.67%) | 994 (68.88%) | 944 (67.53%) |
| 3 | 383 (22.41%) | 407 (24.14%) | 334 (23.15%) | 356 (25.46%) |
| 6 | 37 (2.17%) | 34 (2.02%) | 34 (2.36%) | 28 (2.00%) |
| 9 | 5 (0.29%) | 4 (0.24%) | 4 (0.28%) | 4 (0.29%) |
| Total | 1709 | 1686 | 1443 | 1398 |
| Signed-rank (P) | 43093 (0.0000) | 47229 (0.0000) | 33343.50 (0.0000) | 36915.50 (0.0000) |
| 6 months after treatment | | | | |
| 0 | 729 (42.43%) | 692 (40.71%) | 613 (42.93%) | 549 (39.61%) |
| 3 | 638 (37.14%) | 664 (39.06%) | 539 (37.75%) | 561 (40.48%) |
| 6 | 345 (20.08%) | 334 (19.65%) | 272 (19.05%) | 272 (19.62%) |
| 9 | 6 (0.35%) | 10 (0.59%) | 4 (0.28%) | 4 (0.29%) |
| Total | 1718 | 1700 | 1428 | 1386 |
| 6 months after treatment-baseline | | | | |
| −9 | 1 (0.06%) | 1 (0.06%) | 1 (0.07%) | 0 (0.00%) |
| −6 | 3 (0.18%) | 14 (0.83%) | 3 (0.21%) | 7 (0.51%) |
| −3 | 88 (5.15%) | 88 (5.22%) | 64 (4.49%) | 56 (4.06%) |
| 0 | 1105 (64.66%) | 1046 (62.04%) | 904 (63.44%) | 846 (61.30%) |
| 1 | 1 (0.06%) | 0 (0.00%) | 1 (0.07%) | 0 (0.00%) |
| 3 | 459 (26.86%) | 482 (28.59%) | 407 (28.56%) | 427 (30.94%) |
| 6 | 48 (2.81%) | 51 (3.02%) | 42 (2.95%) | 41 (2.97%) |
| 9 | 4 (0.23%) | 4 (0.24%) | 3 (0.21%) | 3 (0.22%) |
| Total | 1709 | 1686 | 1425 | 1380 |
| Signed-rank (P) | 64831 (0.0000) | 68356 (0.0000) | 50818.00 (0.0000) | 54318.00 (0.0000) |
| 9 months after treatment | | | | |
| 0 | 791 (46.04%) | 741 (43.59%) | 661 (46.71%) | 594 (43.68%) |
| 3 | 618 (35.97%) | 653 (38.41%) | 519 (36.68%) | 536 (39.41%) |

TABLE 25-continued change of chest tightness in different observations

| | FAS | | PP | |
|---|---|---|---|---|
| Items | Control group | Trial group | Control group | Trial group |
| 6 | 305 (17.75%) | 291 (17.12%) | 233 (16.47%) | 225 (16.54%) |
| 9 | 4 (0.23%) | 15 (0.88%) | 2 (0.14%) | 5 (0.37%) |
| Total | 1718 | 1700 | 1415 | 1360 |
| 9 months after treatment-baseline | | | | |
| −9 | 0 (0.00%) | 4 (0.24%) | 0 (0.00%) | 1 (0.07%) |
| −6 | 3 (0.18%) | 14 (0.83%) | 3 (0.21%) | 3 (0.22%) |
| −3 | 93 (5.44%) | 80 (4.74%) | 65 (4.61%) | 49 (3.62%) |
| 0 | 1007 (58.92%) | 946 (56.11%) | 801 (56.81%) | 735 (54.32%) |
| 3 | 534 (31.25%) | 566 (33.57%) | 476 (33.76%) | 502 (37.10%) |
| 6 | 68 (3.98%) | 71 (4.21%) | 62 (4.40%) | 59 (4.36%) |
| 9 | 4 (0.23%) | 5 (0.30%) | 3 (0.21%) | 4 (0.30%) |
| Total | 1709 | 1686 | 1410 | 1353 |
| Signed-rank (P) | 92186 (0.0000) | 98615 (0.0000) | 73535.50 (0.0000) | 79748.00 (0.0000) |
| 12 months after treatment | | | | |
| 0 | 858 (49.94%) | 820 (48.24%) | 725 (51.67%) | 666 (49.33%) |
| 3 | 607 (35.33%) | 613 (36.06%) | 501 (35.71%) | 496 (36.74%) |
| 6 | 248 (14.44%) | 252 (14.82%) | 176 (12.54%) | 186 (13.78%) |
| 9 | 5 (0.29%) | 15 (0.88%) | 1 (0.07%) | 2 (0.15%) |
| Total | 1718 | 1700 | 1403 | 1350 |
| 12 months after treatment-baseline | | | | |
| −9 | 0 (0.00%) | 5 (0.30%) | 0 (0.00%) | 1 (0.07%) |
| −6 | 3 (0.18%) | 12 (0.71%) | 2 (0.14%) | 0 (0.00%) |
| −3 | 83 (4.86%) | 63 (3.74%) | 54 (3.86%) | 29 (2.16%) |
| 0 | 933 (54.59%) | 837 (49.64%) | 721 (51.54%) | 623 (46.39%) |
| 3 | 598 (34.99%) | 673 (39.92%) | 539 (38.53%) | 605 (45.05%) |
| 6 | 87 (5.09%) | 89 (5.28%) | 79 (5.65%) | 79 (5.88%) |
| 9 | 5 (0.29%) | 7 (0.42%) | 4 (0.29%) | 6 (0.45%) |
| Total | 1709 | 1686 | 1399 | 1343 |
| Signed-rank (P) | 120256 (0.0000) | 143536 (0.0000) | 97784.50 (0.0000) | 119855.5 (0.0000) |
| Follow-up | | | | |
| 0 | 754 (52.84%) | 698 (50.73%) | 733 (52.62%) | 675 (50.37%) |
| 2 | 1 (0.07%) | 0 (0.00%) | 1 (0.07%) | 0 (0.00%) |
| 3 | 479 (33.57%) | 488 (35.47%) | 472 (33.88%) | 479 (35.75%) |
| 6 | 192 (13.45%) | 188 (13.66%) | 186 (13.35%) | 184 (13.73%) |
| 9 | 1 (0.07%) | 2 (0.15%) | 1 (0.07%) | 2 (0.15%) |
| Total | 1427 | 1376 | 1393 | 1340 |
| Follow-up-baseline | | | | |
| −9 | 1 (0.07%) | 0 (0.00%) | 1 (0.07%) | 0 (0.00%) |
| −6 | 4 (0.28%) | 4 (0.29%) | 4 (0.29%) | 4 (0.30%) |
| −3 | 55 (3.86%) | 37 (2.70%) | 54 (3.88%) | 35 (2.62%) |
| 0 | 728 (51.09%) | 698 (50.91%) | 712 (51.19%) | 684 (51.20%) |
| 1 | 1 (0.07%) | 0 (0.00%) | 1 (0.07%) | 0 (0.00%) |
| 3 | 544 (38.18%) | 535 (39.02%) | 528 (37.96%) | 520 (38.92%) |
| 6 | 87 (6.11%) | 91 (6.64%) | 86 (6.18%) | 88 (6.59%) |
| 9 | 5 (0.35%) | 6 (0.44%) | 5 (0.36%) | 5 (0.37%) |
| Total | 1425 | 1371 | 1391 | 1336 |
| Signed-rank (P) | 101793 (0.0000) | 100320 (0.0000) | 96444.50 (0.0000) | 94303.00 (0.0000) |

TABLE 26 test of change of chest tightness in different observations

| | | FAS | | PP | |
|---|---|---|---|---|---|
| Items | Test method | Statistic | P value | Statistic | P value |
| Baseline | Rank-sum test | 0.04 | 0.9672 | 0.73 | 0.4677 |
| 1 month after treatment | Rank-sum test | 0.27 | 0.7887 | 0.66 | 0.5063 |
| 1 month after treatment-baseline | Rank-sum test | 0.25 | 0.8053 | 0.66 | 0.5082 |
| 3 months after treatment | Rank-sum test | 0.39 | 0.6979 | 0.67 | 0.5031 |

TABLE 26-continued test of change of chest tightness in different observations

| Items | Test method | FAS Statistic | FAS P value | PP Statistic | PP P value |
|---|---|---|---|---|---|
| 3 months after treatment-baseline | Rank-sum test | 0.64 | 0.5218 | 1.24 | 0.2156 |
| 6 months after treatment | Rank-sum test | 0.71 | 0.4754 | 1.49 | 0.1367 |
| 6 months after treatment-baseline | Rank-sum test | 0.75 | 0.4506 | 1.24 | 0.2140 |
| 9 months after treatment | Rank-sum test | 1.17 | 0.2416 | 1.35 | 0.1761 |
| 9 months after treatment-baseline | Rank-sum test | 1.31 | 0.1892 | 1.87 | 0.0611 |
| 12 months after treatment | Rank-sum test | 1.13 | 0.2603 | 1.35 | 0.1779 |
| 12 months after treatment-baseline | Rank-sum test | 2.78 | 0.0054 | 3.73 | 0.0002 |
| Follow-up | Rank-sum test | 1.01 | 0.3120 | 1.10 | 0.2717 |
| Follow-up-baseline | Rank-sum test | 1.13 | 0.2571 | 1.06 | 0.2878 |

TABLE 27 change of short breath in different observations

| Items | FAS Control group | FAS Trial group | PP Control group | PP Trial group |
|---|---|---|---|---|
| Baseline | | | | |
| 0 | 257 (15.04%) | 217 (12.87%) | 213 (14.48%) | 162 (11.42%) |
| 3 | 886 (51.84%) | 917 (54.39%) | 752 (51.12%) | 761 (53.67%) |
| 6 | 533 (31.19%) | 519 (30.78%) | 479 (32.56%) | 467 (32.93%) |
| 9 | 33 (1.93%) | 33 (1.96%) | 27 (1.84%) | 28 (1.97%) |
| Total | 1709 | 1686 | 1471 | 1418 |
| 1 month after treatment | | | | |
| 0 | 363 (21.14%) | 318 (18.72%) | 303 (20.68%) | 258 (18.14%) |
| 3 | 931 (54.22%) | 982 (57.80%) | 787 (53.72%) | 807 (56.75%) |
| 6 | 410 (23.88%) | 386 (22.72%) | 365 (24.91%) | 346 (24.33%) |
| 9 | 13 (0.76%) | 13 (0.77%) | 10 (0.68%) | 11 (0.77%) |
| Total | 1717 | 1699 | 1465 | 1422 |
| 1 month after treatment-baseline | | | | |
| −6 | 0 (0.00%) | 1 (0.06%) | 0 (0.00%) | 1 (0.07%) |
| −4 | 8 (0.47%) | 6 (0.36%) | 7 (0.48%) | 3 (0.21%) |
| −2 | 90 (5.26%) | 85 (5.03%) | 77 (5.27%) | 69 (4.88%) |
| 0 | 1323 (77.37%) | 1310 (77.56%) | 1132 (77.53%) | 1099 (77.72%) |
| 2 | 252 (14.74%) | 255 (15.10%) | 213 (14.59%) | 214 (15.13%) |
| 4 | 30 (1.75%) | 25 (1.48%) | 25 (1.71%) | 21 (1.49%) |
| 6 | 7 (0.41%) | 7 (0.41%) | 6 (0.41%) | 7 (0.50%) |
| Total | 1710 | 1689 | 1460 | 1414 |
| Signed-rank (P) | 19212 (0.0000) | 19001 (0.0000) | 13629.00 (0.0000) | 13889.00 (0.0000) |
| 3 months after treatment | | | | |
| 0 | 374 (21.78%) | 354 (20.82%) | 310 (21.44%) | 288 (20.47%) |
| 3 | 1012 (58.94%) | 1018 (59.88%) | 855 (59.13%) | 834 (59.28%) |
| 6 | 318 (18.52%) | 318 (18.71%) | 271 (18.74%) | 279 (19.83%) |
| 9 | 13 (0.76%) | 10 (0.59%) | 10 (0.69%) | 6 (0.43%) |
| Total | 1717 | 1700 | 1446 | 1407 |
| 3 months after treatment-baseline | | | | |
| −6 | 0 (0.00%) | 1 (0.06%) | 0 (0.00%) | 1 (0.07%) |
| −4 | 2 (0.12%) | 5 (0.30%) | 2 (0.14%) | 4 (0.29%) |
| −2 | 93 (5.44%) | 108 (6.39%) | 76 (5.27%) | 84 (6.00%) |
| 0 | 1219 (71.29%) | 1181 (69.92%) | 1014 (70.27%) | 975 (69.69%) |
| 2 | 350 (20.47%) | 342 (20.25%) | 309 (21.41%) | 288 (20.59%) |
| 4 | 37 (2.16%) | 45 (2.66%) | 34 (2.36%) | 40 (2.86%) |
| 6 | 9 (0.53%) | 7 (0.41%) | 8 (0.55%) | 7 (0.50%) |
| Total | 1710 | 1689 | 1443 | 1399 |
| Signed-rank (P) | 38821 (0.0000) | 37407 (0.0000) | 30642.50 (0.0000) | 27385.50 (0.0000) |
| 6 months after treatment | | | | |
| 0 | 430 (25.03%) | 400 (23.53%) | 360 (25.21%) | 320 (23.05%) |
| 2 | 1 (0.06%) | 0 (0.00%) | 1 (0.07%) | 0 (0.00%) |
| 3 | 998 (58.09%) | 1024 (60.24%) | 838 (58.68%) | 849 (61.17%) |

TABLE 27-continued change of short breath in different observations

| | FAS | | PP | |
|---|---|---|---|---|
| Items | Control group | Trial group | Control group | Trial group |
| 6 | 280 (16.30%) | 266 (15.65%) | 222 (15.55%) | 215 (15.49%) |
| 9 | 9 (0.52%) | 10 (0.59%) | 7 (0.49%) | 4 (0.29%) |
| Total | 1718 | 1700 | 1428 | 1388 |
| 6 months after treatment-baseline | | | | |
| −6 | 2 (0.12%) | 0 (0.00%) | 2 (0.14%) | 0 (0.00%) |
| −4 | 2 (0.12%) | 7 (0.41%) | 2 (0.14%) | 4 (0.29%) |
| −2 | 102 (5.96%) | 112 (6.63%) | 76 (5.33%) | 85 (6.15%) |
| 0 | 1109 (64.85%) | 1077 (63.77%) | 906 (63.53%) | 859 (62.20%) |
| 2 | 435 (25.44%) | 426 (25.22%) | 387 (27.14%) | 374 (27.08%) |
| 4 | 51 (2.98%) | 57 (3.37%) | 45 (3.16%) | 50 (3.62%) |
| 6 | 9 (0.53%) | 10 (0.59%) | 8 (0.56%) | 9 (0.65%) |
| Total | 1710 | 1689 | 1426 | 1381 |
| Signed-rank (P) | 60693 (0.0000) | 59612 (0.0000) | 48093.00 (0.0000) | 46755.50 (0.0000) |
| 9 months after treatment | | | | |
| 0 | 489 (28.46%) | 473 (27.82%) | 416 (29.42%) | 387 (28.46%) |
| 3 | 994 (57.86%) | 1007 (59.24%) | 824 (58.27%) | 820 (60.29%) |
| 6 | 227 (13.21%) | 207 (12.18%) | 169 (11.95%) | 150 (11.03%) |
| 9 | 8 (0.47%) | 13 (0.76%) | 5 (0.35%) | 3 (0.22%) |
| Total | 1718 | 1700 | 1414 | 1360 |
| 9 months after treatment-baseline | | | | |
| −6 | 1 (0.06%) | 0 (0.00%) | 1 (0.07%) | 0 (0.00%) |
| −4 | 4 (0.23%) | 8 (0.47%) | 2 (0.14%) | 4 (0.30%) |
| −2 | 107 (6.26%) | 109 (6.45%) | 78 (5.53%) | 76 (5.61%) |
| 0 | 1010 (59.06%) | 976 (57.79%) | 798 (56.60%) | 746 (55.10%) |
| 2 | 519 (30.35%) | 519 (30.73%) | 470 (33.33%) | 464 (34.27%) |
| 4 | 61 (3.57%) | 69 (4.09%) | 54 (3.83%) | 57 (4.21%) |
| 6 | 8 (0.47%) | 8 (0.47%) | 7 (0.50%) | 7 (0.52%) |
| Total | 1710 | 1689 | 1410 | 1354 |
| Signed-rank (P) | 85799 (0.0000) | 87654 (0.0000) | 70616.50 (0.0000) | 69726.00 (0.0000) |
| 12 months after treatment | | | | |
| 0 | 545 (31.72%) | 549 (32.29%) | 468 (33.36%) | 462 (34.22%) |
| 3 | 995 (57.92%) | 1024 (60.24%) | 820 (58.45%) | 831 (61.56%) |
| 6 | 173 (10.07%) | 114 (6.71%) | 115 (8.20%) | 56 (4.15%) |
| 9 | 5 (0.29%) | 13 (0.76%) | 0 (0.00%) | 1 (0.07%) |
| Total | 1718 | 1700 | 1403 | 1350 |
| 12 months after treatment-treatment | | | | |
| −4 | 2 (0.12%) | 6 (0.36%) | 1 (0.07%) | 1 (0.07%) |
| −2 | 108 (6.32%) | 101 (5.98%) | 75 (5.36%) | 67 (4.99%) |
| 0 | 955 (55.85%) | 932 (55.18%) | 743 (53.11%) | 699 (52.01%) |
| 2 | 563 (32.92%) | 551 (32.62%) | 506 (36.17%) | 491 (36.53%) |
| 4 | 70 (4.09%) | 87 (5.15%) | 63 (4.50%) | 75 (5.58%) |
| 6 | 12 (0.70%) | 12 (0.71%) | 11 (0.79%) | 11 (0.82%) |
| Total | 1710 | 1689 | 1399 | 1344 |
| Signed-rank (P) | 104992 (0.0000) | 106281 (0.0000) | 85309.50 (0.0000) | 84844.50 (0.0000) |
| Follow-up | | | | |
| 0 | 509 (35.62%) | 470 (34.08%) | 493 (35.34%) | 455 (33.88%) |
| 2 | 1 (0.07%) | 0 (0.00%) | 1 (0.07%) | 0 (0.00%) |
| 3 | 779 (54.51%) | 781 (56.64%) | 763 (54.70%) | 763 (56.81%) |
| 6 | 137 (9.59%) | 124 (8.99%) | 135 (9.68%) | 122 (9.08%) |
| 9 | 3 (0.21%) | 4 (0.29%) | 3 (0.22%) | 3 (0.22%) |
| Total | 1429 | 1379 | 1395 | 1343 |
| Follow-up-baseline | | | | |
| −6 | 2 (0.14%) | 0 (0.00%) | 2 (0.14%) | 0 (0.00%) |
| −4 | 0 (0.00%) | 2 (0.15%) | 0 (0.00%) | 2 (0.15%) |
| −2 | 71 (4.98%) | 62 (4.52%) | 71 (5.10%) | 60 (4.49%) |
| 0 | 744 (52.21%) | 708 (51.60%) | 725 (52.12%) | 692 (51.80%) |
| 2 | 519 (36.42%) | 504 (36.73%) | 507 (36.45%) | 492 (36.83%) |

TABLE 27-continued change of short breath in different observations

| | FAS | | PP | |
|---|---|---|---|---|
| Items | Control group | Trial group | Control group | Trial group |
| 4 | 78 (5.47%) | 82 (5.98%) | 76 (5.46%) | 77 (5.76%) |
| 6 | 11 (0.77%) | 14 (1.02%) | 10 (0.72%) | 13 (0.97%) |
| Total | 1425 | 1372 | 1391 | 1336 |
| Signed-rank (P) | 93780 (0.0000) | 91596 (0.0000) | 89180.00 (0.0000) | 86071.00 (0.0000) |

TABLE 28 test of change of short breath in different observations

| | | FAS | | PP | |
|---|---|---|---|---|---|
| Items | Test method | Statistic | P value | Statistic | P value |
| Baseline | Rank-sum test | 0.64 | 0.5233 | 1.27 | 0.2025 |
| 1 month after treatment | Rank-sum test | 0.52 | 0.5997 | 0.79 | 0.4302 |
| 1 month after treatment-baseline | Rank-sum test | 0.19 | 0.8476 | 0.54 | 0.5878 |
| 3 months after treatment | Rank-sum test | 0.43 | 0.6645 | 0.72 | 0.4720 |
| 3 months after treatment-baseline | Rank-sum test | −0.43 | 0.6636 | −0.56 | 0.5756 |
| 6 months after treatment | Rank-sum test | 0.49 | 0.6222 | 0.85 | 0.3931 |
| 6 months after treatment-baseline | Rank-sum test | −0.15 | 0.8770 | 0.03 | 0.9791 |
| 9 months after treatment | Rank-sum test | 0.04 | 0.9684 | 0.05 | 0.9635 |
| 9 months after treatment-baseline | Rank-sum test | 0.42 | 0.6767 | 0.64 | 0.5230 |
| 12 months after treatment | Rank-sum test | −1.41 | 0.1587 | −1.81 | 0.0706 |
| 12 months after treatment-baseline | Rank-sum test | 0.63 | 0.5258 | 1.00 | 0.3160 |
| Follow-up | Rank-sum test | 0.57 | 0.5680 | 0.50 | 0.6158 |
| Follow-up-baseline | Rank-sum test | 0.78 | 0.4347 | 0.71 | 0.4756 |

TABLE 29 change of fatigue in different observations

| | FAS | | PP | |
|---|---|---|---|---|
| Items | Control group | Trial group | Control group | Trial group |
| Baseline | | | | |
| 0 | 315 (18.42%) | 323 (19.12%) | 268 (18.22%) | 254 (17.90%) |
| 2 | 1042 (60.94%) | 1010 (59.80%) | 890 (60.50%) | 848 (59.76%) |
| 4 | 289 (16.90%) | 296 (17.53%) | 261 (17.74%) | 265 (18.68%) |
| 6 | 64 (3.74%) | 60 (3.55%) | 52 (3.54%) | 52 (3.66%) |
| Total | 1710 | 1689 | 1471 | 1419 |
| 1 month after treatment | | | | |
| 0 | 413 (24.05%) | 426 (25.07%) | 346 (23.62%) | 343 (24.10%) |
| 2 | 1043 (60.75%) | 1011 (59.51%) | 890 (60.75%) | 847 (59.52%) |
| 4 | 238 (13.86%) | 234 (13.77%) | 211 (14.40%) | 210 (14.76%) |
| 6 | 23 (1.34%) | 28 (1.65%) | 18 (1.23%) | 23 (1.62%) |
| Total | 1717 | 1699 | 1465 | 1423 |
| 1 month after treatment-baseline | | | | |
| −6 | 1 (0.06%) | 2 (0.12%) | 1 (0.07%) | 2 (0.14%) |
| −4 | 11 (0.64%) | 16 (0.95%) | 9 (0.62%) | 8 (0.57%) |
| −2 | 98 (5.73%) | 107 (6.34%) | 87 (5.96%) | 89 (6.30%) |
| 0 | 1238 (72.40%) | 1162 (68.88%) | 1054 (72.24%) | 972 (68.84%) |
| 1 | 1 (0.06%) | 0 (0.00%) | 1 (0.07%) | 0 (0.00%) |
| 2 | 303 (17.72%) | 320 (18.97%) | 260 (17.82%) | 274 (19.41%) |
| 4 | 45 (2.63%) | 70 (4.15%) | 35 (2.40%) | 59 (4.18%) |
| 6 | 13 (0.76%) | 10 (0.59%) | 12 (0.82%) | 8 (0.57%) |
| Total | 1710 | 1687 | 1459 | 1412 |
| Signed-rank (P) | 30817 (0.0000) | 37573 (0.0000) | 22149.00 (0.0000) | 28265.00 (0.0000) |
| 3 months after treatment | | | | |
| 0 | 480 (27.96%) | 471 (27.71%) | 409 (28.28%) | 378 (26.87%) |
| 2 | 1026 (59.76%) | 1018 (59.88%) | 864 (59.75%) | 849 (60.34%) |

TABLE 29-continued change of fatigue in different observations

| | FAS | | PP | |
|---|---|---|---|---|
| Items | Control group | Trial group | Control group | Trial group |
| 4 | 197 (11.47%) | 195 (11.47%) | 165 (11.41%) | 168 (11.94%) |
| 6 | 14 (0.82%) | 16 (0.94%) | 8 (0.55%) | 12 (0.85%) |
| Total | 1717 | 1700 | 1446 | 1407 |
| 3 months after treatment-baseline | | | | |
| −6 | 2 (0.12%) | 2 (0.12%) | 2 (0.14%) | 1 (0.07%) |
| −4 | 9 (0.53%) | 14 (0.83%) | 6 (0.42%) | 8 (0.57%) |
| −2 | 86 (5.03%) | 105 (6.22%) | 70 (4.85%) | 86 (6.16%) |
| 0 | 1107 (64.74%) | 1054 (62.48%) | 923 (63.96%) | 864 (61.85%) |
| 2 | 420 (24.56%) | 408 (24.18%) | 368 (25.50%) | 349 (24.98%) |
| 4 | 70 (4.09%) | 92 (5.45%) | 60 (4.16%) | 80 (5.73%) |
| 6 | 16 (0.94%) | 12 (0.71%) | 14 (0.97%) | 9 (0.64%) |
| Total | 1710 | 1687 | 1443 | 1397 |
| Signed-rank (P) | 63149 (0.0000) | 64162 (0.0000) | 48511.00 (0.0000) | 48043.00 (0.0000) |
| 6 months after treatment | | | | |
| 0 | 520 (30.27%) | 508 (29.88%) | 443 (31.00%) | 410 (29.54%) |
| 2 | 1048 (61.00%) | 1053 (61.94%) | 881 (61.65%) | 874 (62.97%) |
| 4 | 135 (7.86%) | 126 (7.41%) | 97 (6.79%) | 95 (6.84%) |
| 6 | 15 (0.87%) | 13 (0.76%) | 8 (0.56%) | 9 (0.65%) |
| Total | 1718 | 1700 | 1429 | 1388 |
| 6 months after treatment-baseline | | | | |
| −6 | 0 (0.00%) | 4 (0.24%) | 0 (0.00%) | 3 (0.22%) |
| −4 | 12 (0.70%) | 9 (0.53%) | 8 (0.56%) | 3 (0.22%) |
| −2 | 108 (6.32%) | 108 (6.40%) | 86 (6.03%) | 84 (6.09%) |
| 0 | 974 (56.96%) | 929 (55.07%) | 791 (55.47%) | 738 (53.52%) |
| 2 | 488 (28.54%) | 499 (29.58%) | 428 (30.01%) | 430 (31.18%) |
| 4 | 110 (6.43%) | 123 (7.29%) | 97 (6.80%) | 108 (7.83%) |
| 6 | 18 (1.05%) | 15 (0.89%) | 16 (1.12%) | 13 (0.94%) |
| Total | 1710 | 1687 | 1426 | 1379 |
| Signed-rank (P) | 95480 (0.0000) | 101941 (0.0000) | 74284.00 (0.0000) | 77640.00 (0.0000) |
| 9 months after treatment | | | | |
| 0 | 576 (33.53%) | 581 (34.18%) | 498 (35.22%) | 473 (34.78%) |
| 2 | 1035 (60.24%) | 1017 (59.82%) | 857 (60.61%) | 828 (60.88%) |
| 4 | 88 (5.12%) | 92 (5.41%) | 49 (3.47%) | 53 (3.90%) |
| 6 | 19 (1.11%) | 10 (0.59%) | 10 (0.71%) | 6 (0.44%) |
| Total | 1718 | 1700 | 1414 | 1360 |
| 9 months after treatment-baseline | | | | |
| −6 | 1 (0.06%) | 3 (0.18%) | 0 (0.00%) | 2 (0.15%) |
| −4 | 13 (0.76%) | 8 (0.47%) | 7 (0.50%) | 3 (0.22%) |
| −2 | 115 (6.73%) | 104 (6.16%) | 92 (6.52%) | 76 (5.63%) |
| 0 | 864 (50.53%) | 828 (49.08%) | 679 (48.12%) | 623 (46.11%) |
| 2 | 572 (33.45%) | 577 (34.20%) | 503 (35.65%) | 505 (37.38%) |
| 4 | 125 (7.31%) | 142 (8.42%) | 112 (7.94%) | 121 (8.96%) |
| 6 | 20 (1.17%) | 25 (1.48%) | 18 (1.28%) | 21 (1.55%) |
| Total | 1710 | 1687 | 1411 | 1351 |
| Signed-rank (P) | 128910 (0.0000) | 140633 (0.0000) | 102138.0 (0.0000) | 107197.5 (0.0000) |
| 12 months after treatment | | | | |
| 0 | 630 (36.67%) | 650 (38.24%) | 548 (39.06%) | 537 (39.78%) |
| 2 | 1000 (58.21%) | 968 (56.94%) | 816 (58.16%) | 775 (57.41%) |
| 4 | 76 (4.42%) | 76 (4.47%) | 37 (2.64%) | 36 (2.67%) |
| 6 | 12 (0.70%) | 6 (0.35%) | 2 (0.14%) | 2 (0.15%) |
| Total | 1718 | 1700 | 1403 | 1350 |
| 12 months after treatment-baseline | | | | |
| −4 | 11 (0.64%) | 12 (0.71%) | 4 (0.29%) | 5 (0.37%) |
| −6 | 0 (0.00%) | 1 (0.06%) | | |
| −2 | 100 (5.85%) | 101 (5.99%) | 76 (5.43%) | 70 (5.22%) |
| 0 | 805 (47.08%) | 747 (44.28%) | 617 (44.10%) | 540 (40.24%) |
| 2 | 605 (35.38%) | 630 (37.34%) | 532 (38.03%) | 558 (41.58%) |

TABLE 29-continued change of fatigue in different observations

| | FAS | | PP | |
|---|---|---|---|---|
| Items | Control group | Trial group | Control group | Trial group |
| 4 | 164 (9.59%) | 168 (9.96%) | 147 (10.51%) | 144 (10.73%) |
| 6 | 25 (1.46%) | 28 (1.66%) | 23 (1.64%) | 25 (1.86%) |
| Total | 1710 | 1687 | 1399 | 1342 |
| Signed-rank (P) | 160960 (0.0000) | 173385 (0.0000) | 127198.5 (0.0000) | 135471.5 (0.0000) |
| Follow-up | | | | |
| 0 | 611 (42.76%) | 590 (42.82%) | 597 (42.80%) | 570 (42.47%) |
| 2 | 759 (53.11%) | 733 (53.19%) | 739 (52.97%) | 721 (53.73%) |
| 4 | 56 (3.92%) | 53 (3.85%) | 56 (4.01%) | 50 (3.73%) |
| 6 | 3 (0.21%) | 2 (0.15%) | 3 (0.22%) | 1 (0.07%) |
| Total | 1429 | 1378 | 1395 | 1342 |
| Follow-up-baseline | | | | |
| −4 | 5 (0.35%) | 6 (0.44%) | 3 (0.22%) | 4 (0.30%) |
| −2 | 87 (6.11%) | 72 (5.25%) | 86 (6.18%) | 71 (5.32%) |
| 0 | 608 (42.67%) | 533 (38.88%) | 598 (42.99%) | 525 (39.33%) |
| 2 | 537 (37.68%) | 558 (40.70%) | 523 (37.60%) | 542 (40.60%) |
| 4 | 158 (11.09%) | 175 (12.76%) | 153 (11.00%) | 168 (12.58%) |
| 6 | 30 (2.11%) | 27 (1.97%) | 28 (2.01%) | 25 (1.87%) |
| Total | 1425 | 1371 | 1391 | 1335 |
| Signed-rank (P) | 136359 (0.0000) | 148729 (0.0000) | 129118.0 (0.0000) | 139632.5 (0.0000) |

TABLE 30 test of change of fatigue in different observations

| | | FAS | | PP | |
|---|---|---|---|---|---|
| Items | Test method | Statistic | P value | Statistic | P value |
| Baseline | Rank-sum test | −0.15 | 0.8815 | 0.59 | 0.5564 |
| 1 month after treatment | Rank-sum test | −0.38 | 0.7052 | 0.11 | 0.9118 |
| 1 month after treatment-baseline | Rank-sum test | 1.13 | 0.2603 | 1.60 | 0.1090 |
| 3 months after treatment | Rank-sum test | 0.19 | 0.8519 | 0.99 | 0.3202 |
| 3 months after treatment-baseline | Rank-sum test | −0.04 | 0.9663 | 0.02 | 0.9855 |
| 6 months after treatment | Rank-sum test | −0.02 | 0.9814 | 0.79 | 0.4323 |
| 6 months after treatment-baseline | Rank-sum test | 0.91 | 0.3633 | 1.06 | 0.2910 |
| 9 months after treatment | Rank-sum test | −0.46 | 0.6430 | 0.28 | 0.7833 |
| 9 months after treatment-baseline | Rank-sum test | 1.58 | 0.1150 | 1.83 | 0.0676 |
| 12 months after treatment | Rank-sum test | −0.98 | 0.3255 | −0.36 | 0.7217 |
| 12 months after treatment-baseline | Rank-sum test | 1.21 | 0.2273 | 1.75 | 0.0802 |
| Follow-up | Rank-sum test | −0.07 | 0.9429 | 0.03 | 0.9763 |
| Follow-up-baseline | Rank-sum test | 2.34 | 0.0194 | 2.25 | 0.0243 |

TABLE 31 change of palpitation in different observations

| | FAS | | PP | |
|---|---|---|---|---|
| Items | Control group | Trial group | Control group | Trial group |
| Baseline | | | | |
| 0 | 315 (18.42%) | 281 (16.66%) | 263 (17.88%) | 224 (15.81%) |
| 2 | 803 (46.96%) | 780 (46.24%) | 690 (46.91%) | 644 (45.45%) |
| 4 | 470 (27.49%) | 508 (30.11%) | 416 (28.28%) | 445 (31.40%) |
| 6 | 122 (7.13%) | 118 (6.99%) | 102 (6.93%) | 104 (7.34%) |
| Total | 1710 | 1687 | 1471 | 1417 |
| 1 month after treatment | | | | |
| 0 | 427 (24.87%) | 393 (23.13%) | 353 (24.11%) | 319 (22.42%) |
| 1 | 1 (0.06%) | 0 (0.00%) | 1 (0.07%) | 0 (0.00%) |
| 2 | 834 (48.57%) | 859 (50.56%) | 713 (48.70%) | 714 (50.18%) |

TABLE 31-continued change of palpitation in different observations

| | FAS | | PP | |
|---|---|---|---|---|
| Items | Control group | Trial group | Control group | Trial group |
| 4 | 398 (23.18%) | 386 (22.72%) | 351 (23.98%) | 338 (23.75%) |
| 6 | 57 (3.32%) | 61 (3.59%) | 46 (3.14%) | 52 (3.65%) |
| Total | 1717 | 1699 | 1464 | 1423 |
| 1 month after treatment-baseline | | | | |
| −3 | 0 (0.00%) | 2 (0.12%) | 0 (0.00%) | 1 (0.07%) |
| −2 | 1 (0.06%) | 2 (0.12%) | 1 (0.07%) | 1 (0.07%) |
| −1 | 103 (6.02%) | 98 (5.80%) | 87 (5.96%) | 75 (5.30%) |
| 0 | 1242 (72.63%) | 1278 (75.67%) | 1051 (71.99%) | 1075 (76.03%) |
| 1 | 334 (19.53%) | 277 (16.40%) | 295 (20.21%) | 234 (16.55%) |
| 2 | 25 (1.46%) | 29 (1.72%) | 22 (1.51%) | 26 (1.84%) |
| 3 | 5 (0.29%) | 3 (0.18%) | 4 (0.27%) | 2 (0.14%) |
| Total | 1710 | 1689 | 1460 | 1414 |
| Signed-rank (P) | 31866 (0.0000) | 22309 (0.0000) | 24868.00 (0.0000) | 16529.00 (0.0000) |
| 3 months after treatment | | | | |
| 0 | 480 (27.96%) | 438 (25.76%) | 403 (27.87%) | 350 (24.88%) |
| 2 | 894 (52.07%) | 898 (52.82%) | 759 (52.49%) | 748 (53.16%) |
| 4 | 310 (18.05%) | 320 (18.82%) | 261 (18.05%) | 275 (19.55%) |
| 6 | 33 (1.92%) | 44 (2.59%) | 23 (1.59%) | 34 (2.42%) |
| Total | 1717 | 1700 | 1446 | 1407 |
| 3 months after treatment-baseline | | | | |
| −3 | 0 (0.00%) | 3 (0.18%) | 0 (0.00%) | 1 (0.07%) |
| −2 | 2 (0.12%) | 4 (0.24%) | 1 (0.07%) | 2 (0.14%) |
| −1 | 119 (6.96%) | 94 (5.57%) | 99 (6.86%) | 72 (5.15%) |
| 0 | 1125 (65.79%) | 1125 (66.61%) | 943 (65.35%) | 923 (65.98%) |
| 1 | 415 (24.27%) | 412 (24.39%) | 356 (24.67%) | 358 (25.59%) |
| 2 | 43 (2.51%) | 45 (2.66%) | 39 (2.70%) | 38 (2.72%) |
| 3 | 6 (0.35%) | 6 (0.36%) | 5 (0.35%) | 5 (0.36%) |
| Total | 1710 | 1689 | 1443 | 1399 |
| Signed-rank (P) | 52756 (0.0000) | 52032 (0.0000) | 39577.50 (0.0000) | 39872.50 (0.0000) |
| 6 months after treatment | | | | |
| 0 | 538 (31.32%) | 492 (28.94%) | 456 (31.91%) | 396 (28.53%) |
| 2 | 906 (52.74%) | 945 (55.59%) | 764 (53.46%) | 786 (56.63%) |
| 4 | 246 (14.32%) | 229 (13.47%) | 192 (13.44%) | 185 (13.33%) |
| 6 | 28 (1.63%) | 34 (2.00%) | 17 (1.19%) | 21 (1.51%) |
| Total | 1718 | 1700 | 1429 | 1388 |
| 6 months after treatment-baseline | | | | |
| −2 | 5 (0.29%) | 8 (0.47%) | 4 (0.28%) | 3 (0.22%) |
| −3 | 0 (0.00%) | 2 (0.12%) | | |
| −1 | 116 (6.78%) | 102 (6.04%) | 88 (6.18%) | 74 (5.36%) |
| 0 | 1034 (60.47%) | 1022 (60.51%) | 842 (59.09%) | 827 (59.88%) |
| 1 | 490 (28.65%) | 495 (29.31%) | 431 (30.25%) | 425 (30.77%) |
| 2 | 56 (3.27%) | 52 (3.08%) | 53 (3.72%) | 45 (3.26%) |
| 3 | 9 (0.53%) | 8 (0.47%) | 7 (0.49%) | 7 (0.51%) |
| Total | 1710 | 1689 | 1425 | 1381 |
| Signed-rank (P) | 76022 (0.0000) | 74546 (0.0000) | 60046.00 (0.0000) | 56797.00 (0.0000) |
| 9 months after treatment | | | | |
| 0 | 581 (33.82%) | 570 (33.53%) | 496 (35.05%) | 464 (34.14%) |
| 2 | 929 (54.07%) | 939 (55.24%) | 782 (55.27%) | 768 (56.51%) |
| 4 | 179 (10.42%) | 164 (9.65%) | 122 (8.62%) | 113 (8.31%) |
| 6 | 29 (1.69%) | 27 (1.59%) | 15 (1.06%) | 14 (1.03%) |
| Total | 1718 | 1700 | 1415 | 1359 |
| 9 months after treatment-baseline | | | | |
| −2 | 5 (0.29%) | 12 (0.71%) | 4 (0.28%) | 4 (0.30%) |
| −3 | 0 (0.00%) | 2 (0.12%) | | |
| −1 | 117 (6.84%) | 105 (6.22%) | 87 (6.17%) | 74 (5.47%) |
| 0 | 948 (55.44%) | 906 (53.64%) | 749 (53.12%) | 699 (51.62%) |
| 1 | 557 (32.57%) | 601 (35.58%) | 493 (34.96%) | 524 (38.70%) |

TABLE 31-continued change of palpitation in different observations

| | FAS | | PP | |
|---|---|---|---|---|
| Items | Control group | Trial group | Control group | Trial group |
| 2 | 76 (4.44%) | 53 (3.14%) | 71 (5.04%) | 46 (3.40%) |
| 3 | 7 (0.41%) | 10 (0.59%) | 6 (0.43%) | 7 (0.52%) |
| Total | 1710 | 1689 | 1410 | 1354 |
| Signed-rank (P) | 102289 (0.0000) | 105928 (0.0000) | 81650.00 (0.0000) | 82763.00 (0.0000) |
| 12 months after treatment | | | | |
| 0 | 669 (38.94%) | 638 (37.53%) | 576 (41.05%) | 529 (39.19%) |
| 2 | 892 (51.92%) | 911 (53.59%) | 745 (53.10%) | 738 (54.67%) |
| 4 | 138 (8.03%) | 131 (7.71%) | 78 (5.56%) | 76 (5.63%) |
| 6 | 19 (1.11%) | 20 (1.18%) | 4 (0.29%) | 7 (0.52%) |
| 合计 | 1718 | 1700 | 1403 | 1350 |
| 12 months after treatment-baseline | | | | |
| −2 | 4 (0.23%) | 10 (0.59%) | 3 (0.21%) | 1 (0.07%) |
| −3 | 0 (0.00%) | 2 (0.12%) | | |
| −1 | 112 (6.55%) | 106 (6.28%) | 78 (5.58%) | 74 (5.51%) |
| 0 | 882 (51.58%) | 861 (50.98%) | 679 (48.53%) | 655 (48.81%) |
| 1 | 602 (35.20%) | 620 (36.71%) | 536 (38.31%) | 533 (39.72%) |
| 2 | 102 (5.96%) | 84 (4.97%) | 97 (6.93%) | 75 (5.59%) |
| 3 | 8 (0.47%) | 6 (0.36%) | 6 (0.43%) | 4 (0.30%) |
| Total | 1710 | 1689 | 1399 | 1342 |
| Signed-rank (P) | 128493 (0.0000) | 123688 (0.0000) | 103801.5 (0.0000) | 95022.50 (0.0000) |
| Follow-up | | | | |
| 0 | 631 (44.16%) | 591 (42.86%) | 613 (43.94%) | 570 (42.44%) |
| 2 | 697 (48.78%) | 704 (51.05%) | 683 (48.96%) | 692 (51.53%) |
| 4 | 95 (6.65%) | 76 (5.51%) | 94 (6.74%) | 74 (5.51%) |
| 6 | 6 (0.42%) | 8 (0.58%) | 5 (0.36%) | 7 (0.52%) |
| Total | 1429 | 1379 | 1395 | 1343 |
| Follow-up-baseline | | | | |
| −3 | 1 (0.07%) | 0 (0.00%) | 1 (0.07%) | 0 (0.00%) |
| −2 | 3 (0.21%) | 1 (0.07%) | 3 (0.22%) | 1 (0.07%) |
| −1 | 90 (6.32%) | 96 (7.00%) | 86 (6.19%) | 93 (6.96%) |
| 0 | 690 (48.46%) | 651 (47.45%) | 677 (48.71%) | 634 (47.46%) |
| 1 | 528 (37.08%) | 539 (39.29%) | 516 (37.12%) | 523 (39.15%) |
| 2 | 97 (6.81%) | 73 (5.32%) | 93 (6.69%) | 73 (5.46%) |
| 3 | 15 (1.05%) | 12 (0.87%) | 14 (1.01%) | 12 (0.90%) |
| Total | 1424 | 1372 | 1390 | 1336 |
| Sign-rank (P) | 104286 (0.0000) | 98940 (0.0000) | 98684.00 (0.0000) | 94032.50 (0.0000) |

TABLE 32 test of change of palpitation in different observations

| | | FAS | | PP | |
|---|---|---|---|---|---|
| Items | test method | Statistic | P value | Statistic | P value |
| Baseline | Rank-sum test | 1.60 | 0.1095 | 2.06 | 0.0390 |
| 1 month after treatment | Rank-sum test | 0.68 | 0.4960 | 0.82 | 0.4149 |
| 1 month after treatment-baseline | Rank-sum test | −1.78 | 0.0743 | −1.63 | 0.1028 |
| 3 months after treatment | Rank-sum test | 1.61 | 0.1080 | 2.14 | 0.0325 |
| 3 months after treatment-baseline | Rank-sum test | 0.65 | 0.5179 | 1.09 | 0.2752 |
| 6 months after treatment | Rank-sum test | 0.97 | 0.3297 | 1.58 | 0.1146 |
| 6 months after treatment-baseline | Rank-sum test | 0.32 | 0.7466 | 0.26 | 0.7913 |
| 9 months after treatment | Rank-sum test | −0.18 | 0.8559 | 0.31 | 0.7557 |
| 9 months after treatment-baseline | Rank-sum test | 0.72 | 0.4730 | 0.87 | 0.3820 |
| 12 months after treatment | Rank-sum test | 0.64 | 0.5198 | 1.00 | 0.3150 |
| 12 months after treatment-baseline | Rank-sum test | −0.15 | 0.8821 | −0.31 | 0.7560 |
| Follow-up | Rank-sum test | 0.35 | 0.7270 | 0.41 | 0.6795 |
| Follow-up-baseline | Rank-sum test | −0.27 | 0.7903 | −0.15 | 0.8833 |

TABLE 33 change of spontaneous perspiration in different observations

| | FAS | | PP | |
|---|---|---|---|---|
| Items | Control group | Trial group | Control group | Trial group |
| Baseline | | | | |
| 0 | 430 (25.15%) | 409 (24.22%) | 367 (24.95%) | 333 (23.47%) |
| 1 | 941 (55.03%) | 962 (56.96%) | 803 (54.59%) | 808 (56.94%) |
| 2 | 298 (17.43%) | 284 (16.81%) | 265 (18.01%) | 246 (17.34%) |
| 3 | 41 (2.40%) | 34 (2.01%) | 36 (2.45%) | 32 (2.26%) |
| Total | 1710 | 1689 | 1471 | 1419 |
| 1 month after treatment | | | | |
| 0 | 603 (35.12%) | 541 (31.84%) | 518 (35.36%) | 449 (31.55%) |
| 1 | 879 (51.19%) | 933 (54.91%) | 738 (50.38%) | 777 (54.60%) |
| 2 | 215 (12.52%) | 206 (12.12%) | 195 (13.31%) | 182 (12.79%) |
| 3 | 20 (1.16%) | 19 (1.12%) | 14 (0.96%) | 15 (1.05%) |
| Total | 1717 | 1699 | 1465 | 1423 |
| 1 month after treatment-baseline | | | | |
| −3 | 3 (0.18%) | 5 (0.30%) | 3 (0.21%) | 5 (0.35%) |
| −2 | 17 (0.99%) | 8 (0.47%) | 14 (0.96%) | 7 (0.50%) |
| −1 | 94 (5.50%) | 108 (6.39%) | 77 (5.27%) | 82 (5.80%) |
| 0 | 1249 (73.08%) | 1227 (72.65%) | 1068 (73.15%) | 1041 (73.62%) |
| 1 | 279 (16.33%) | 276 (16.34%) | 238 (16.30%) | 228 (16.12%) |
| 2 | 51 (2.98%) | 59 (3.49%) | 48 (3.29%) | 47 (3.32%) |
| 3 | 16 (0.94%) | 6 (0.36%) | 12 (0.82%) | 4 (0.28%) |
| Total | 1709 | 1689 | 1460 | 1414 |
| Signed-rank (P) | 27157 (0.0000) | 27058 (0.0000) | 20342.00 (0.0000) | 17917.00 (0.0000) |
| 3 months after treatment | | | | |
| 0 | 667 (38.85%) | 664 (39.06%) | 563 (38.93%) | 550 (39.09%) |
| 1 | 846 (49.27%) | 853 (50.18%) | 709 (49.03%) | 710 (50.46%) |
| 2 | 190 (11.07%) | 172 (10.12%) | 167 (11.55%) | 140 (9.95%) |
| 3 | 14 (0.82%) | 11 (0.65%) | 7 (0.48%) | 7 (0.50%) |
| Total | 1717 | 1700 | 1446 | 1407 |
| 3 months after treatment-baseline | | | | |
| −3 | 2 (0.12%) | 2 (0.12%) | 2 (0.14%) | 2 (0.14%) |
| −2 | 15 (0.88%) | 9 (0.53%) | 13 (0.90%) | 6 (0.43%) |
| −1 | 121 (7.08%) | 124 (7.34%) | 101 (7.00%) | 100 (7.15%) |
| 0 | 1083 (63.37%) | 1068 (63.23%) | 898 (62.23%) | 877 (62.73%) |
| 1 | 392 (22.94%) | 393 (23.27%) | 342 (23.70%) | 334 (23.89%) |
| 2 | 76 (4.45%) | 86 (5.09%) | 71 (4.92%) | 74 (5.29%) |
| 3 | 20 (1.17%) | 7 (0.41%) | 16 (1.11%) | 5 (0.36%) |
| Total | 1709 | 1689 | 1443 | 1398 |
| Signed-rank (P) | 57413 (0.0000) | 58131 (0.0000) | 44586.00 (0.0000) | 42357.50 (0.0000) |
| 6 months after treatment | | | | |
| 0 | 728 (42.37%) | 714 (42.00%) | 628 (43.98%) | 593 (42.72%) |
| 1 | 833 (48.49%) | 842 (49.53%) | 676 (47.34%) | 688 (49.57%) |
| 2 | 144 (8.38%) | 136 (8.00%) | 117 (8.19%) | 103 (7.42%) |
| 3 | 13 (0.76%) | 8 (0.47%) | 7 (0.49%) | 4 (0.29%) |
| Total | 1718 | 1700 | 1428 | 1388 |
| 6 months after treatment-baseline | | | | |
| −3 | 0 (0.00%) | 3 (0.18%) | 0 (0.00%) | 3 (0.22%) |
| −2 | 23 (1.35%) | 14 (0.83%) | 20 (1.40%) | 9 (0.65%) |
| −1 | 137 (8.02%) | 120 (7.10%) | 105 (7.37%) | 89 (6.45%) |
| 0 | 959 (56.11%) | 973 (57.61%) | 774 (54.32%) | 785 (56.88%) |
| 1 | 468 (27.38%) | 455 (26.94%) | 414 (29.05%) | 387 (28.04%) |
| 2 | 93 (5.44%) | 112 (6.63%) | 88 (6.18%) | 96 (6.96%) |
| 3 | 29 (1.70%) | 12 (0.71%) | 24 (1.68%) | 11 (0.80%) |
| Total | 1709 | 1689 | 1425 | 1380 |
| Signed-rank (P) | 84041 (0.0000) | 82717 (0.0000) | 67343.00 (0.0000) | 60902.00 (0.0000) |
| 9 months after treatment | | | | |
| 0 | 788 (45.87%) | 776 (45.65%) | 678 (47.95%) | 647 (47.57%) |
| 1 | 813 (47.32%) | 818 (48.12%) | 652 (46.11%) | 650 (47.79%) |

TABLE 33-continued change of spontaneous perspiration in different observations

| | FAS | | PP | |
|---|---|---|---|---|
| Items | Control group | Trial group | Control group | Trial group |
| 2 | 105 (6.11%) | 100 (5.88%) | 79 (5.59%) | 61 (4.49%) |
| 3 | 12 (0.70%) | 6 (0.35%) | 5 (0.35%) | 2 (0.15%) |
| Total | 1718 | 1700 | 1414 | 1360 |
| 9 months after treatment-baseline | | | | |
| −3 | 0 (0.00%) | 3 (0.18%) | 0 (0.00%) | 3 (0.22%) |
| −2 | 10 (0.59%) | 15 (0.89%) | 6 (0.43%) | 8 (0.59%) |
| −1 | 154 (9.01%) | 110 (6.51%) | 122 (8.65%) | 80 (5.92%) |
| 0 | 910 (53.25%) | 910 (53.88%) | 717 (50.85%) | 711 (52.63%) |
| 1 | 491 (28.73%) | 508 (30.08%) | 434 (30.78%) | 426 (31.53%) |
| 2 | 113 (6.61%) | 130 (7.70%) | 105 (7.45%) | 112 (8.29%) |
| 3 | 31 (1.81%) | 13 (0.77%) | 26 (1.84%) | 11 (0.81%) |
| Total | 1709 | 1689 | 1410 | 1351 |
| Signed-rank (P) | 102988 (0.0000) | 105181 (0.0000) | 82586.50 (0.0000) | 75847.50 (0.0000) |
| 12 months after treatment | | | | |
| 0 | 845 (49.19%) | 814 (47.88%) | 730 (52.03%) | 673 (49.93%) |
| 1 | 804 (46.80%) | 813 (47.82%) | 640 (45.62%) | 646 (47.92%) |
| 2 | 58 (3.38%) | 68 (4.00%) | 31 (2.21%) | 28 (2.08%) |
| 3 | 11 (0.64%) | 5 (0.29%) | 2 (0.14%) | 1 (0.07%) |
| Total | 1718 | 1700 | 1403 | 1348 |
| 12 months after treatment-baseline | | | | |
| −2 | 12 (0.70%) | 9 (0.53%) | 8 (0.57%) | 2 (0.15%) |
| −3 | 0 (0.00%) | 2 (0.12%) | | |
| −1 | 137 (8.02%) | 116 (6.87%) | 103 (7.37%) | 81 (6.03%) |
| 0 | 837 (48.98%) | 844 (49.97%) | 647 (46.28%) | 646 (48.10%) |
| 1 | 550 (32.18%) | 546 (32.33%) | 483 (34.55%) | 463 (34.48%) |
| 2 | 139 (8.13%) | 153 (9.06%) | 128 (9.16%) | 136 (10.13%) |
| 3 | 34 (1.99%) | 19 (1.12%) | 29 (2.07%) | 15 (1.12%) |
| Total | 1709 | 1689 | 1398 | 1343 |
| Signed-rank (P) | 134030 (0.0000) | 131902 (0.0000) | 105721.5 (0.0000) | 98327.00 (0.0000) |
| Follow-up | | | | |
| 0 | 767 (53.71%) | 719 (52.18%) | 750 (53.80%) | 699 (52.09%) |
| 1 | 595 (41.67%) | 601 (43.61%) | 578 (41.46%) | 587 (43.74%) |
| 2 | 62 (4.34%) | 58 (4.21%) | 62 (4.45%) | 56 (4.17%) |
| 3 | 4 (0.28%) | 0 (0.00%) | 4 (0.29%) | 0 (0.00%) |
| Total | 1428 | 1378 | 1394 | 1342 |
| Follow-up-baseline | | | | |
| −3 | 2 (0.14%) | 1 (0.07%) | 2 (0.14%) | 1 (0.07%) |
| −2 | 8 (0.56%) | 5 (0.36%) | 8 (0.58%) | 5 (0.37%) |
| −1 | 119 (8.36%) | 92 (6.71%) | 116 (8.35%) | 91 (6.81%) |
| 0 | 656 (46.07%) | 649 (47.30%) | 644 (46.33%) | 631 (47.23%) |
| 1 | 466 (32.72%) | 464 (33.82%) | 451 (32.45%) | 452 (33.83%) |
| 2 | 141 (9.90%) | 143 (10.42%) | 138 (9.93%) | 140 (10.48%) |
| 3 | 32 (2.25%) | 18 (1.31%) | 31 (2.23%) | 16 (1.20%) |
| Total | 1424 | 1372 | 1390 | 1336 |
| Signed-rank (P) | 105998 (0.0000) | 101375 (0.0000) | 99787.50 (0.0000) | 95903.50 (0.0000) |

TABLE 34 test of change of spontaneous perspiration in different observations

| | | FAS | | PP | |
|---|---|---|---|---|---|
| Items | Test method | Statistic | P value | Statistic | P value |
| Baseline | Rank-sum test | −0.03 | 0.9765 | 0.26 | 0.7929 |
| 1 month after treatment | Rank-sum test | 1.43 | 0.1536 | 1.55 | 0.1213 |
| 1 month after treatment-baseline | Rank-sum test | −0.29 | 0.7709 | −0.52 | 0.6002 |
| 3 months after treatment | Rank-sum test | −0.49 | 0.6219 | −0.56 | 0.5750 |
| 3 months after treatment-baseline | Rank-sum test | 0.12 | 0.9053 | −0.03 | 0.9741 |
| 6 months after treatment | Rank-sum test | −0.04 | 0.9706 | 0.30 | 0.7638 |

TABLE 34-continued test of change of spontaneous perspiration in different observations

| Items | Test method | FAS Statistic | FAS P value | PP Statistic | PP P value |
|---|---|---|---|---|---|
| 6 months after treatment-baseline | Rank-sum test | 0.35 | 0.7234 | −0.05 | 0.9606 |
| 9 months after treatment | Rank-sum test | −0.07 | 0.9432 | −0.17 | 0.8632 |
| 9 months after treatment-baseline | Rank-sum test | 1.27 | 0.2053 | 0.82 | 0.4096 |
| 12 months after treatment | Rank-sum test | 0.79 | 0.4302 | 1.02 | 0.3094 |
| 12 months after treatment-baseline | Rank-sum test | 0.43 | 0.6642 | 0.41 | 0.6850 |
| Follow-up | Rank-sum test | 0.66 | 0.5111 | 0.70 | 0.4831 |
| Follow-up-baseline | Rank-sum test | 0.65 | 0.5170 | 0.68 | 0.4968 |

TABLE 35 change of pale complexion in different observations

| Items | FAS Control group | FAS Trial group | PP Control group | PP Trial group |
|---|---|---|---|---|
| Baseline | | | | |
| 0 | 572 (33.47%) | 552 (32.68%) | 494 (33.61%) | 450 (31.71%) |
| 1 | 741 (43.36%) | 731 (43.28%) | 626 (42.59%) | 623 (43.90%) |
| 2 | 325 (19.02%) | 345 (20.43%) | 293 (19.93%) | 300 (21.14%) |
| 3 | 71 (4.15%) | 61 (3.61%) | 57 (3.88%) | 46 (3.24%) |
| Total | 1709 | 1689 | 1470 | 1419 |
| 1 month after treatment | | | | |
| 0 | 713 (41.53%) | 695 (40.91%) | 613 (41.81%) | 569 (39.99%) |
| 1 | 726 (42.28%) | 705 (41.49%) | 615 (41.95%) | 597 (41.95%) |
| 2 | 245 (14.27%) | 269 (15.83%) | 211 (14.39%) | 231 (16.23%) |
| 3 | 33 (1.92%) | 30 (1.77%) | 27 (1.84%) | 26 (1.83%) |
| Total | 1717 | 1699 | 1466 | 1423 |
| 1 month after treatment-baseline | | | | |
| −1 | 65 (3.81%) | 50 (2.97%) | 52 (3.57%) | 43 (3.05%) |
| 0 | 1477 (86.48%) | 1444 (85.70%) | 1275 (87.45%) | 1199 (85.16%) |
| 1 | 166 (9.72%) | 191 (11.34%) | 131 (8.98%) | 166 (11.79%) |
| Total | 1708 | 1685 | 1458 | 1408 |
| Signed-rank (P) | 5858.0 (0.0000) | 8530.5 (0.0000) | 3634.00 (0.0000) | 6457.50 (0.0000) |
| 3 months after treatment | | | | |
| 0 | 809 (47.12%) | 776 (45.65%) | 693 (47.89%) | 637 (45.31%) |
| 1 | 677 (39.43%) | 697 (41.00%) | 566 (39.12%) | 586 (41.68%) |
| 2 | 210 (12.23%) | 206 (12.12%) | 172 (11.89%) | 168 (11.95%) |
| 3 | 21 (1.22%) | 21 (1.24%) | 16 (1.11%) | 15 (1.07%) |
| Total | 1717 | 1700 | 1447 | 1406 |
| 3 months after treatment-baseline | | | | |
| −1 | 62 (3.63%) | 60 (3.56%) | 47 (3.26%) | 46 (3.30%) |
| 0 | 1387 (81.21%) | 1340 (79.53%) | 1177 (81.68%) | 1099 (78.84%) |
| 1 | 259 (15.16%) | 285 (16.91%) | 217 (15.06%) | 249 (17.86%) |
| Total | 1708 | 1685 | 1441 | 1394 |
| Signed-rank (P) | 15859 (0.0000) | 19463 (0.0000) | 11262.50 (0.0000) | 15022.00 (0.0000) |
| 6 months after treatment 1 month after treatment | | | | |
| 0 | 871 (50.70%) | 863 (50.76%) | 750 (52.48%) | 708 (51.05%) |
| 1 | 657 (38.24%) | 645 (37.94%) | 540 (37.79%) | 536 (38.64%) |
| 2 | 179 (10.42%) | 170 (10.00%) | 133 (9.31%) | 130 (9.37%) |
| 3 | 11 (0.64%) | 22 (1.29%) | 6 (0.42%) | 13 (0.94%) |
| Total | 1718 | 1700 | 1429 | 1387 |
| 6 months after treatment-baseline | | | | |
| −1 | 67 (3.92%) | 57 (3.38%) | 49 (3.44%) | 37 (2.69%) |
| 0 | 1322 (77.40%) | 1268 (75.25%) | 1104 (77.47%) | 1024 (74.42%) |
| 1 | 319 (18.68%) | 360 (21.36%) | 272 (19.09%) | 315 (22.89%) |
| Total | 1708 | 1685 | 1425 | 1376 |
| Signed-rank (P) | 24381 (0.0000) | 31664 (0.0000) | 17951.50 (0.0000) | 24533.50 (0.0000) |

TABLE 35-continued change of pale complexion in different observations

| | FAS | | PP | |
|---|---|---|---|---|
| Items | Control group | Trial group | Control group | Trial group |
| 9 months after treatment | | | | |
| 0 | 912 (53.08%) | 913 (53.71%) | 788 (55.69%) | 743 (54.75%) |
| 1 | 653 (38.01%) | 639 (37.59%) | 520 (36.75%) | 515 (37.95%) |
| 2 | 142 (8.27%) | 133 (7.82%) | 101 (7.14%) | 93 (6.85%) |
| 3 | 11 (0.64%) | 15 (0.88%) | 6 (0.42%) | 6 (0.44%) |
| Total | 1718 | 1700 | 1415 | 1357 |
| 9 months after treatment-baseline | | | | |
| −1 | 59 (3.45%) | 54 (3.20%) | 40 (2.85%) | 29 (2.15%) |
| 0 | 1284 (75.18%) | 1210 (71.81%) | 1049 (74.66%) | 949 (70.35%) |
| 1 | 365 (21.37%) | 421 (24.99%) | 316 (22.49%) | 371 (27.50%) |
| Total | 1708 | 1685 | 1405 | 1349 |
| Signed-rank (P) | 32513 (0.0000) | 43673 (0.0000) | 24633.00 (0.0000) | 34285.50 (0.0000) |
| 12 months after treatment | | | | |
| 0 | 1011 (58.85%) | 978 (57.53%) | 870 (62.01%) | 806 (59.75%) |
| 1 | 590 (34.34%) | 617 (36.29%) | 463 (33.00%) | 489 (36.25%) |
| 2 | 104 (6.05%) | 94 (5.53%) | 63 (4.49%) | 53 (3.93%) |
| 3 | 13 (0.76%) | 11 (0.65%) | 7 (0.50%) | 1 (0.07%) |
| Total | 1718 | 1700 | 1403 | 1349 |
| 12 months after treatment-baseline | | | | |
| −1 | 56 (3.28%) | 55 (3.26%) | 37 (2.65%) | 27 (2.02%) |
| 0 | 1202 (70.37%) | 1155 (68.55%) | 967 (69.22%) | 891 (66.54%) |
| 1 | 450 (26.35%) | 475 (28.19%) | 393 (28.13%) | 421 (31.44%) |
| Total | 1708 | 1685 | 1397 | 1339 |
| Signed-rank (P) | 49940 (0.0000) | 55755 (0.0000) | 38359.00 (0.0000) | 44226.50 (0.0000) |
| Follow-up | | | | |
| 0 | 882 (61.72%) | 826 (59.94%) | 862 (61.79%) | 802 (59.76%) |
| 1 | 465 (32.54%) | 487 (35.34%) | 452 (32.40%) | 475 (35.39%) |
| 2 | 76 (5.32%) | 61 (4.43%) | 75 (5.38%) | 61 (4.55%) |
| 3 | 6 (0.42%) | 4 (0.29%) | 6 (0.43%) | 4 (0.30%) |
| Total | 1429 | 1378 | 1395 | 1342 |
| Follow-up-baseline | | | | |
| −1 | 39 (2.75%) | 30 (2.19%) | 39 (2.82%) | 30 (2.25%) |
| 0 | 950 (66.95%) | 914 (66.76%) | 932 (67.29%) | 892 (66.92%) |
| 1 | 430 (30.30%) | 425 (31.04%) | 414 (29.89%) | 411 (30.83%) |
| Total | 1419 | 1369 | 1385 | 1333 |
| Signed-rank (P) | 45943 (0.0000) | 45030 (0.0000) | 42562.50 (0.0000) | 42100.50 (0.0000) |

TABLE 36 test of change of pale complexion in different observations

| | | FAS | | PP | |
|---|---|---|---|---|---|
| Items | Test method | Statistic | P value | Statistic | P value |
| Baseline | Rank-sum test | 0.55 | 0.5821 | 0.82 | 0.4120 |
| 1 month after treatment | Rank-sum test | 0.71 | 0.4797 | 1.29 | 0.1977 |
| 1 month after treatment-baseline | Rank-sum test | 1.94 | 0.0522 | 2.46 | 0.0137 |
| 3 months after treatment | Rank-sum test | 0.68 | 0.4981 | 1.14 | 0.2523 |
| 3 months after treatment-baseline | Rank-sum test | 1.27 | 0.2024 | 1.79 | 0.0741 |
| 6 months after treatment | Rank-sum test | 0.07 | 0.9429 | 0.83 | 0.4056 |
| 6 months after treatment-baseline | Rank-sum test | 2.06 | 0.0394 | 2.64 | 0.0083 |
| 9 months after treatment | Rank-sum test | −0.36 | 0.7175 | 0.39 | 0.6987 |
| 9 months after treatment-baseline | Rank-sum test | 2.42 | 0.0155 | 3.17 | 0.0015 |
| 12 months after treatment | Rank-sum test | 0.56 | 0.5750 | 0.93 | 0.3509 |
| 12 months after treatment-baseline | Rank-sum test | 1.13 | 0.2598 | 2.05 | 0.0405 |
| Follow-up | Rank-sum test | 0.69 | 0.4925 | 0.81 | 0.4160 |
| Follow-up-baseline | Rank-sum test | 0.62 | 0.5363 | 0.72 | 0.4698 |

I.6.4.4 Seattle Angina Questionnaire (SAQ)

The evaluation results in the SAQ were depicted in different observations, and inter-group comparison was tested by Wilcoxon Rank-sum test.

TABLE 37 different observations (Question 1-1)

| | FAS | | PP | |
|---|---|---|---|---|
| Items | Control group | Trial group | Control group | Trial group |
| Baseline | | | | |
| Severely limited | 1 (0.06%) | 3 (0.17%) | 1 (0.07%) | 3 (0.21%) |
| Moderately limited | 16 (0.92%) | 18 (1.05%) | 13 (0.87%) | 14 (0.97%) |
| Mildly limited | 34 (1.95%) | 41 (2.39%) | 30 (2.01%) | 32 (2.21%) |
| Slightly limited | 102 (5.86%) | 104 (6.05%) | 87 (5.82%) | 88 (6.09%) |
| Not limited | 1582 (90.92%) | 1547 (90.05%) | 1359 (90.96%) | 1305 (90.31%) |
| Other reasons | 5 (0.29%) | 5 (0.29%) | 4 (0.27%) | 3 (0.21%) |
| Total | 1740 | 1718 | 1494 | 1445 |
| 1 month after treatment | | | | |
| Severely limited | 2 (0.11%) | 0 (0.00%) | 1 (0.07%) | 0 (0.00%) |
| Moderately limited | 11 (0.63%) | 11 (0.64%) | 9 (0.60%) | 8 (0.55%) |
| Mildly limited | 24 (1.38%) | 36 (2.09%) | 21 (1.41%) | 26 (1.80%) |
| Slightly limited | 95 (5.45%) | 89 (5.16%) | 80 (5.38%) | 73 (5.06%) |
| Not limited | 1607 (92.20%) | 1584 (91.83%) | 1375 (92.41%) | 1333 (92.31%) |
| Other reasons | 4 (0.23%) | 5 (0.29%) | 2 (0.13%) | 4 (0.28%) |
| Total | 1743 | 1725 | 1488 | 1444 |
| 3 months after treatment | | | | |
| Severely limited | 1 (0.06%) | 0 (0.00%) | 0 (0.00%) | 0 (0.00%) |
| Moderately limited | 7 (0.40%) | 8 (0.46%) | 6 (0.41%) | 4 (0.28%) |
| Mildly limited | 26 (1.49%) | 36 (2.09%) | 22 (1.50%) | 26 (1.82%) |
| Slightly limited | 72 (4.13%) | 70 (4.06%) | 58 (3.95%) | 56 (3.92%) |
| Not limited | 1634 (93.69%) | 1609 (93.28%) | 1381 (93.95%) | 1343 (93.92%) |
| Other reasons | 4 (0.23%) | 2 (0.12%) | 3 (0.20%) | 1 (0.07%) |
| Total | 1744 | 1725 | 1470 | 1430 |
| 6 months after treatment | | | | |
| Severely limited | 1 (0.06%) | 0 (0.00%) | 0 (0.00%) | 0 (0.00%) |
| Moderately limited | 4 (0.23%) | 7 (0.41%) | 4 (0.28%) | 3 (0.21%) |
| Mildly limited | 29 (1.66%) | 23 (1.33%) | 22 (1.52%) | 14 (1.00%) |
| Slightly limited | 69 (3.96%) | 77 (4.46%) | 53 (3.66%) | 58 (4.13%) |
| Not limited | 1638 (93.92%) | 1613 (93.51%) | 1368 (94.34%) | 1325 (94.37%) |
| Other reasons | 3 (0.17%) | 5 (0.29%) | 3 (0.21%) | 4 (0.28%) |
| Total | 1744 | 1725 | 1450 | 1404 |
| 9 months after treatment | | | | |
| Severely limited | 1 (0.06%) | 0 (0.00%) | 0 (0.00%) | 0 (0.00%) |
| Moderately limited | 5 (0.29%) | 9 (0.52%) | 3 (0.21%) | 5 (0.36%) |
| Mildly limited | 25 (1.43%) | 21 (1.22%) | 18 (1.25%) | 11 (0.80%) |
| Slightly limited | 67 (3.84%) | 71 (4.12%) | 47 (3.27%) | 49 (3.55%) |
| Not limited | 1643 (94.21%) | 1618 (93.80%) | 1366 (95.06%) | 1309 (94.92%) |
| Other reasons | 3 (0.17%) | 6 (0.35%) | 3 (0.21%) | 5 (0.36%) |
| Total | 1744 | 1725 | 1437 | 1379 |
| 12 months after treatment | | | | |
| Severely limited | 1 (0.06%) | 0 (0.00%) | 0 (0.00%) | 0 (0.00%) |
| Moderately limited | 4 (0.23%) | 7 (0.41%) | 1 (0.07%) | 1 (0.07%) |
| Mildly limited | 15 (0.86%) | 16 (0.93%) | 7 (0.49%) | 6 (0.44%) |
| Slightly limited | 61 (3.50%) | 68 (3.94%) | 41 (2.88%) | 44 (3.22%) |
| Not limited | 1659 (95.13%) | 1630 (94.49%) | 1371 (96.28%) | 1312 (96.12%) |
| Other reasons | 4 (0.23%) | 4 (0.23%) | 4 (0.28%) | 2 (0.15%) |
| Total | 1744 | 1725 | 1424 | 1365 |
| Follow-up | | | | |
| Severely limited | 1 (0.07%) | 3 (0.22%) | 1 (0.07%) | 3 (0.22%) |
| Moderately limited | 1 (0.07%) | 2 (0.14%) | 1 (0.07%) | 2 (0.15%) |
| Mildly limited | 6 (0.42%) | 6 (0.43%) | 6 (0.43%) | 6 (0.44%) |
| Slightly limited | 45 (3.12%) | 45 (3.23%) | 44 (3.12%) | 45 (3.32%) |

TABLE 37-continued different observations (Question 1-1)

| | FAS | | PP | |
|---|---|---|---|---|
| Items | Control group | Trial group | Control group | Trial group |
| Not limited | 1386 (95.98%) | 1334 (95.83%) | 1352 (95.95%) | 1298 (95.72%) |
| Other reasons | 5 (0.35%) | 2 (0.14%) | 5 (0.35%) | 2 (0.15%) |
| Total | 1444 | 1392 | 1409 | 1356 |

TABLE 38 test of different observations (Question 1-1)

| | | FAS | | PP | |
|---|---|---|---|---|---|
| Items | Test method | Statistic | P value | Statistic | P value |
| Baseline | Rank-sum test | −0.90 | 0.3683 | −0.73 | 0.4642 |
| 1 month after treatment | Rank-sum test | −0.31 | 0.7564 | 0.17 | 0.8666 |
| 3 months after treatment | Rank-sum test | −0.79 | 0.4318 | −0.33 | 0.7400 |
| 6 months after treatment | Rank-sum test | −0.21 | 0.8367 | 0.24 | 0.8087 |
| 9 months after treatment | Rank-sum test | −0.08 | 0.9347 | 0.21 | 0.8305 |
| 12 months after treatment | Rank-sum test | −0.83 | 0.4038 | −0.58 | 0.5613 |
| Follow-up | Rank-sum test | −0.74 | 0.4565 | −0.85 | 0.3960 |

TABLE 39 different observations (Question 1-2)

| | FAS | | PP | |
|---|---|---|---|---|
| Items | Control group | Trial group | Control group | Trial group |
| Baseline | | | | |
| Severely limited | 2 (0.11%) | 3 (0.17%) | 2 (0.13%) | 3 (0.21%) |
| Moderately limited | 18 (1.03%) | 17 (0.99%) | 13 (0.87%) | 14 (0.97%) |
| Mildly limited | 46 (2.64%) | 54 (3.14%) | 42 (2.81%) | 41 (2.84%) |
| Slightly limited | 129 (7.41%) | 136 (7.92%) | 113 (7.56%) | 114 (7.89%) |
| Not limited | 1539 (88.45%) | 1505 (87.60%) | 1319 (88.29%) | 1271 (87.96%) |
| Other reasons | 6 (0.34%) | 3 (0.17%) | 5 (0.33%) | 2 (0.14%) |
| Total | 1740 | 1718 | 1494 | 1445 |
| 1 month after treatment | | | | |
| Severely limited | 0 (0.00%) | 0 (0.00%) | 0 (0.00%) | 0 (0.00%) |
| Moderately limited | 14 (0.80%) | 11 (0.64%) | 10 (0.67%) | 9 (0.62%) |
| Mildly limited | 32 (1.84%) | 42 (2.44%) | 30 (2.02%) | 31 (2.15%) |
| Slightly limited | 116 (6.66%) | 124 (7.19%) | 99 (6.65%) | 103 (7.13%) |
| Not limited | 1575 (90.36%) | 1544 (89.56%) | 1345 (90.39%) | 1299 (89.96%) |
| Other reasons | 6 (0.34%) | 3 (0.17%) | 4 (0.27%) | 2 (0.14%) |
| Total | 1743 | 1724 | 1488 | 1444 |
| 3 months after treatment | | | | |
| Severely limited | 0 (0.00%) | 0 (0.00%) | 0 (0.00%) | 0 (0.00%) |
| Moderately limited | 10 (0.57%) | 8 (0.46%) | 8 (0.54%) | 4 (0.28%) |
| Mildly limited | 23 (1.32%) | 43 (2.49%) | 19 (1.29%) | 31 (2.17%) |
| Slightly limited | 101 (5.79%) | 95 (5.51%) | 84 (5.71%) | 78 (5.45%) |
| Not limited | 1603 (91.92%) | 1575 (91.30%) | 1353 (92.04%) | 1315 (91.96%) |
| Other reasons | 7 (0.40%) | 4 (0.23%) | 6 (0.41%) | 2 (0.14%) |
| Total | 1744 | 1725 | 1470 | 1430 |
| 6 months after treatment | | | | |
| Severely limited | 1 (0.06%) | 0 (0.00%) | 1 (0.07%) | 0 (0.00%) |
| Moderately limited | 8 (0.46%) | 8 (0.46%) | 6 (0.41%) | 4 (0.28%) |
| Mildly limited | 27 (1.55%) | 32 (1.86%) | 19 (1.31%) | 19 (1.35%) |
| Slightly limited | 87 (4.99%) | 93 (5.39%) | 66 (4.55%) | 73 (5.20%) |
| Not limited | 1615 (92.60%) | 1586 (91.94%) | 1352 (93.24%) | 1304 (92.88%) |
| Other reasons | 6 (0.34%) | 6 (0.35%) | 6 (0.41%) | 4 (0.28%) |
| Total | 1744 | 1725 | 1450 | 1404 |

TABLE 39-continued different observations (Question 1-2)

| | FAS | | PP | |
|---|---|---|---|---|
| Items | Control group | Trial group | Control group | Trial group |
| 9 months after treatment | | | | |
| Severely limited | 0 (0.00%) | 0 (0.00%) | 0 (0.00%) | 0 (0.00%) |
| Moderately limited | 7 (0.40%) | 10 (0.58%) | 4 (0.28%) | 5 (0.36%) |
| Mildly limited | 29 (1.66%) | 27 (1.57%) | 20 (1.39%) | 13 (0.94%) |
| Slightly limited | 72 (4.13%) | 79 (4.58%) | 50 (3.48%) | 54 (3.92%) |
| Not limited | 1631 (93.52%) | 1602 (92.87%) | 1358 (94.50%) | 1301 (94.34%) |
| Other reasons | 5 (0.29%) | 7 (0.41%) | 5 (0.35%) | 6 (0.44%) |
| Total | 1744 | 1725 | 1437 | 1379 |
| 12 months after treatment | | | | |
| Severely limited | 0 (0.00%) | 0 (0.00%) | 0 (0.00%) | 0 (0.00%) |
| Moderately limited | 6 (0.34%) | 8 (0.46%) | 1 (0.07%) | 1 (0.07%) |
| Mildly limited | 18 (1.03%) | 23 (1.33%) | 8 (0.56%) | 9 (0.66%) |
| Slightly limited | 67 (3.84%) | 79 (4.58%) | 45 (3.16%) | 52 (3.81%) |
| Not limited | 1647 (94.44%) | 1610 (93.33%) | 1365 (95.79%) | 1300 (95.24%) |
| Other reasons | 6 (0.34%) | 5 (0.29%) | 6 (0.42%) | 3 (0.22%) |
| Total | 1744 | 1725 | 1425 | 1365 |
| Follow-up | | | | |
| Severely limited | 2 (0.14%) | 3 (0.22%) | 2 (0.14%) | 3 (0.22%) |
| Moderately limited | 0 (0.00%) | 3 (0.22%) | 0 (0.00%) | 3 (0.22%) |
| Mildly limited | 8 (0.55%) | 4 (0.29%) | 8 (0.57%) | 4 (0.29%) |
| Slightly limited | 57 (3.95%) | 52 (3.74%) | 56 (3.97%) | 51 (3.76%) |
| Not limited | 1370 (94.88%) | 1326 (95.26%) | 1336 (94.82%) | 1291 (95.21%) |
| Not limited | 7 (0.48%) | 4 (0.29%) | 7 (0.50%) | 4 (0.29%) |
| Total | 1444 | 1392 | 1409 | 1356 |

TABLE 40 test of different observations (Question 1-2)

| | | FAS | | PP | |
|---|---|---|---|---|---|
| Items | Test method | Statistic | P value | Statistic | P value |
| Baseline | Rank-sum test | −1.07 | 0.2868 | −0.59 | 0.5561 |
| 1 month after treatment | Rank-sum test | −1.11 | 0.2687 | −0.61 | 0.5434 |
| 3 months after treatment | Rank-sum test | −1.05 | 0.2923 | −0.62 | 0.5328 |
| 6 months after treatment | Rank-sum test | −0.72 | 0.4716 | −0.62 | 0.5356 |
| 9 months after treatment | Rank-sum test | −0.49 | 0.6268 | 0.03 | 0.9734 |
| 12 months after treatment | Rank-sum test | −1.49 | 0.1363 | −1.20 | 0.2294 |
| Follow-up | Rank-sum test | −0.01 | 0.9927 | −0.01 | 0.9885 |

TABLE 41 different observations (Question 1-3)

| | FAS | | PP | |
|---|---|---|---|---|
| Items | Control group | Trial group | Control group | Trial group |
| Baseline | | | | |
| Severely limited | 15 (0.86%) | 13 (0.76%) | 12 (0.80%) | 11 (0.76%) |
| Moderately limited | 53 (3.05%) | 45 (2.63%) | 44 (2.95%) | 36 (2.49%) |
| Mildly limited | 149 (8.57%) | 163 (9.52%) | 135 (9.04%) | 144 (9.98%) |
| Slightly limited | 340 (19.56%) | 348 (20.32%) | 307 (20.56%) | 305 (21.14%) |
| Not limited | 1170 (67.32%) | 1135 (66.26%) | 985 (65.97%) | 941 (65.21%) |
| Other reasons | 11 (0.63%) | 9 (0.53%) | 10 (0.67%) | 6 (0.42%) |
| Total | 1738 | 1713 | 1493 | 1443 |
| 1 month after treatment | | | | |
| Severely limited | 5 (0.29%) | 5 (0.29%) | 5 (0.34%) | 4 (0.28%) |
| Moderately limited | 34 (1.95%) | 34 (1.97%) | 25 (1.68%) | 27 (1.87%) |
| Mildly limited | 126 (7.23%) | 139 (8.06%) | 114 (7.67%) | 123 (8.52%) |

TABLE 41-continued different observations (Question 1-3)

| | FAS | | PP | |
|---|---|---|---|---|
| Items | Control group | Trial group | Control group | Trial group |
| Slightly limited | 307 (17.62%) | 306 (17.75%) | 271 (18.24%) | 265 (18.36%) |
| Not limited | 1261 (72.39%) | 1233 (71.52%) | 1064 (71.60%) | 1018 (70.55%) |
| Other reasons | 9 (0.52%) | 7 (0.41%) | 7 (0.47%) | 6 (0.42%) |
| Total | 1742 | 1724 | 1486 | 1443 |
| 3 months after treatment | | | | |
| Severely limited | 5 (0.29%) | 4 (0.23%) | 5 (0.34%) | 2 (0.14%) |
| Moderately limited | 23 (1.32%) | 28 (1.62%) | 16 (1.09%) | 19 (1.33%) |
| Mildly limited | 93 (5.33%) | 111 (6.44%) | 81 (5.51%) | 91 (6.36%) |
| Slightly limited | 296 (16.97%) | 305 (17.69%) | 257 (17.48%) | 265 (18.53%) |
| Not limited | 1318 (75.57%) | 1268 (73.55%) | 1103 (75.03%) | 1048 (73.29%) |
| Other reason | 9 (0.52%) | 8 (0.46%) | 8 (0.54%) | 5 (0.35%) |
| Total | 1744 | 1724 | 1470 | 1430 |
| 6 months after treatment | | | | |
| Severely limited | 4 (0.23%) | 3 (0.17%) | 4 (0.28%) | 2 (0.14%) |
| Moderately limited | 20 (1.15%) | 25 (1.45%) | 14 (0.97%) | 12 (0.85%) |
| Mildly limited | 86 (4.93%) | 92 (5.34%) | 65 (4.48%) | 75 (5.34%) |
| Slightly limited | 265 (15.19%) | 289 (16.76%) | 227 (15.66%) | 242 (17.24%) |
| Not limited | 1358 (77.87%) | 1307 (75.81%) | 1131 (78.00%) | 1067 (76.00%) |
| Other reasons | 11 (0.63%) | 8 (0.46%) | 9 (0.62%) | 6 (0.43%) |
| Total | 1744 | 1724 | 1450 | 1404 |
| 9 months after treatment | | | | |
| Severely limited | 2 (0.11%) | 2 (0.12%) | 1 (0.07%) | 1 (0.07%) |
| Moderately limited | 17 (0.97%) | 21 (1.22%) | 10 (0.70%) | 8 (0.58%) |
| Mildly limited | 58 (3.33%) | 70 (4.06%) | 37 (2.57%) | 51 (3.70%) |
| Slightly limited | 238 (13.65%) | 272 (15.78%) | 196 (13.64%) | 218 (15.83%) |
| Not limited | 1421 (81.48%) | 1350 (78.31%) | 1187 (82.60%) | 1092 (79.30%) |
| Other reasons | 8 (0.46%) | 9 (0.52%) | 6 (0.42%) | 7 (0.51%) |
| Total | 1744 | 1724 | 1437 | 1377 |
| 12 months after treatment | | | | |
| Severely limited | 2 (0.11%) | 1 (0.06%) | 1 (0.07%) | 0 (0.00%) |
| Moderately limited | 11 (0.63%) | 20 (1.16%) | 3 (0.21%) | 5 (0.37%) |
| Mildly limited | 54 (3.10%) | 46 (2.67%) | 30 (2.11%) | 26 (1.90%) |
| Slightly limited | 196 (11.24%) | 222 (12.88%) | 157 (11.03%) | 169 (12.38%) |
| Not limited | 1471 (84.35%) | 1428 (82.83%) | 1225 (86.03%) | 1161 (85.05%) |
| Other reasons | 10 (0.57%) | 7 (0.41%) | 8 (0.56%) | 4 (0.29%) |
| Total | 1744 | 1724 | 1424 | 1365 |
| Follow-up | | | | |
| Severely limited | 2 (0.14%) | 3 (0.22%) | 2 (0.14%) | 3 (0.22%) |
| Moderately limited | 6 (0.42%) | 6 (0.43%) | 6 (0.43%) | 6 (0.44%) |
| Mildly limited | 30 (2.08%) | 16 (1.15%) | 30 (2.13%) | 16 (1.18%) |
| Slightly limited | 190 (13.17%) | 205 (14.73%) | 182 (12.93%) | 198 (14.60%) |
| Not limited | 1206 (83.58%) | 1157 (83.12%) | 1179 (83.74%) | 1128 (83.19%) |
| Other reasons | 9 (0.62%) | 5 (0.36%) | 9 (0.64%) | 5 (0.37%) |
| Total | 1443 | 1392 | 1408 | 1356 |

TABLE 42 test of different observations (Question 1-3)

| | | FAS | | PP | |
|---|---|---|---|---|---|
| Items | Test method | Statistic | P value | Statistic | P value |
| Baseline | Rank-sum test | −0.70 | 0.4863 | −0.62 | 0.5323 |
| 1 month after treatment | Rank-sum test | −0.76 | 0.4470 | −0.77 | 0.4437 |
| 3 months after treatment | Rank-sum test | −1.53 | 0.1271 | −1.31 | 0.1906 |
| 6 months after treatment | Rank-sum test | −1.62 | 0.1045 | −1.46 | 0.1441 |
| 9 months after treatment | Rank-sum test | −2.25 | 0.0242 | −2.14 | 0.0327 |
| 12 months after treatment | Rank-sum test | −1.41 | 0.1597 | −1.07 | 0.2868 |
| Follow-up | Rank-sum test | −0.57 | 0.5701 | −0.63 | 0.5275 |

TABLE 43

| | different observations (Question 1-4) | | | |
|---|---|---|---|---|
| | FAS | | PP | |
| Items | Control group | Trial group | Control group | Trial group |
| Baseline | | | | |
| Severely limited | 59 (3.41%) | 64 (3.73%) | 51 (3.43%) | 56 (3.88%) |
| Moderately limited | 208 (12.01%) | 206 (12.02%) | 185 (12.42%) | 180 (12.48%) |
| Mildly limited | 402 (23.21%) | 384 (22.40%) | 347 (23.30%) | 338 (23.44%) |
| Slightly limited | 554 (31.99%) | 559 (32.61%) | 478 (32.10%) | 470 (32.59%) |
| Not limited | 495 (28.58%) | 485 (28.30%) | 414 (27.80%) | 384 (26.63%) |
| Other reasons | 14 (0.81%) | 16 (0.93%) | 14 (0.94%) | 14 (0.97%) |
| Total | 1732 | 1714 | 1489 | 1442 |
| 1 month after treatment | | | | |
| Severely limited | 35 (2.01%) | 34 (1.97%) | 27 (1.82%) | 30 (2.08%) |
| Moderately limited | 159 (9.13%) | 150 (8.71%) | 138 (9.31%) | 129 (8.95%) |
| Mildly limited | 349 (20.05%) | 332 (19.27%) | 303 (20.43%) | 281 (19.50%) |
| Slightly limited | 568 (32.62%) | 608 (35.29%) | 483 (32.57%) | 514 (35.67%) |
| Not limited | 618 (35.50%) | 587 (34.07%) | 521 (35.13%) | 476 (33.03%) |
| Other reasons | 12 (0.69%) | 12 (0.70%) | 11 (0.74%) | 11 (0.76%) |
| Total | 1741 | 1723 | 1483 | 1441 |
| 3 months after treatment | | | | |
| Severely limited | 29 (1.66%) | 29 (1.68%) | 22 (1.50%) | 23 (1.61%) |
| Moderately limited | 120 (6.88%) | 120 (6.96%) | 105 (7.16%) | 97 (6.79%) |
| Mildly limited | 325 (18.65%) | 309 (17.91%) | 278 (18.95%) | 264 (18.47%) |
| Slightly limited | 589 (33.79%) | 604 (35.01%) | 492 (33.54%) | 513 (35.90%) |
| Not limited | 668 (38.32%) | 652 (37.80%) | 559 (38.10%) | 523 (36.60%) |
| Other limited | 12 (0.69%) | 11 (0.64%) | 11 (0.75%) | 9 (0.63%) |
| Total | 1743 | 1725 | 1467 | 1429 |
| 6 months after treatment | | | | |
| Severely limited | 29 (1.66%) | 26 (1.51%) | 20 (1.38%) | 18 (1.28%) |
| Moderately limited | 97 (5.56%) | 104 (6.03%) | 74 (5.11%) | 75 (5.34%) |
| Mildly limited | 314 (18.00%) | 278 (16.12%) | 266 (18.37%) | 223 (15.88%) |
| Slightly limited | 560 (32.11%) | 598 (34.67%) | 463 (31.98%) | 513 (36.54%) |
| Not limited | 731 (41.92%) | 713 (41.33%) | 613 (42.33%) | 570 (40.60%) |
| Other reasons | 13 (0.75%) | 6 (0.35%) | 12 (0.83%) | 5 (0.36%) |
| Total | 1744 | 1725 | 1448 | 1404 |
| 9 months after treatment | | | | |
| Severely limited | 19 (1.09%) | 22 (1.28%) | 9 (0.63%) | 12 (0.87%) |
| Moderately limited | 85 (4.87%) | 80 (4.64%) | 63 (4.39%) | 50 (3.63%) |
| Mildly limited | 264 (15.14%) | 255 (14.78%) | 208 (14.49%) | 194 (14.08%) |
| Slightly limited | 569 (32.63%) | 581 (33.68%) | 472 (32.89%) | 489 (35.49%) |
| Not limited | 797 (45.70%) | 774 (44.87%) | 673 (46.90%) | 622 (45.14%) |
| Other reasons | 10 (0.57%) | 13 (0.75%) | 10 (0.70%) | 11 (0.80%) |
| Total | 1744 | 1725 | 1435 | 1378 |
| 12 months after treatment | | | | |
| Severely limited | 13 (0.75%) | 17 (0.99%) | 2 (0.14%) | 7 (0.51%) |
| Moderately limited | 66 (3.78%) | 73 (4.23%) | 41 (2.88%) | 41 (3.01%) |
| Mildly limited | 236 (13.53%) | 224 (12.99%) | 177 (12.43%) | 164 (12.02%) |
| Slightly limited | 565 (32.40%) | 570 (33.04%) | 469 (32.94%) | 476 (34.90%) |
| Not limited | 853 (48.91%) | 831 (48.17%) | 724 (50.84%) | 669 (49.05%) |
| Other reasons | 11 (0.63%) | 10 (0.58%) | 11 (0.77%) | 7 (0.51%) |
| Total | 1744 | 1725 | 1424 | 1364 |
| Follow-up | | | | |
| Severely limited | 5 (0.35%) | 6 (0.43%) | 5 (0.36%) | 6 (0.44%) |
| Moderately limited | 38 (2.64%) | 30 (2.16%) | 37 (2.63%) | 30 (2.22%) |
| Mildly limited | 177 (12.28%) | 176 (12.67%) | 172 (12.23%) | 173 (12.79%) |
| Slightly limited | 436 (30.26%) | 448 (32.25%) | 428 (30.44%) | 439 (32.45%) |
| Not limited | 775 (53.78%) | 720 (51.84%) | 754 (53.63%) | 696 (51.44%) |
| Other reasons | 10 (0.69%) | 9 (0.65%) | 10 (0.71%) | 9 (0.67%) |
| Total | 1441 | 1389 | 1406 | 1353 |

TABLE 44 test of different observations (Question 1-4)

| Items | Test method | FAS Statistic | FAS P value | PP Statistic | PP P value |
|---|---|---|---|---|---|
| Baseline | Rank-sum test | 0.02 | 0.9870 | −0.63 | 0.5294 |
| 1 month after treatment | Rank-sum test | −0.09 | 0.9267 | −0.42 | 0.6741 |
| 3 months after treatment | Rank-sum test | −0.07 | 0.9470 | −0.38 | 0.7062 |
| 6 months after treatment | Rank-sum test | −0.09 | 0.9282 | −0.34 | 0.7364 |
| 9 months after treatment | Rank-sum test | −0.13 | 0.8985 | −0.37 | 0.7113 |
| 12 months after treatment | Rank-sum test | −0.48 | 0.6338 | −0.99 | 0.3205 |
| Follow-up | Rank-sum test | −0.83 | 0.4039 | −0.98 | 0.3274 |

TABLE 45 different observations (Question 1-5)

| Items | FAS Control group | FAS Trial group | PP Control group | PP Trial group |
|---|---|---|---|---|
| Baseline | | | | |
| Severely limited | 53 (3.05%) | 54 (3.16%) | 46 (3.09%) | 46 (3.19%) |
| Moderately limited | 238 (13.72%) | 238 (13.91%) | 210 (14.08%) | 213 (14.78%) |
| Mildly limited | 357 (20.58%) | 369 (21.57%) | 309 (20.72%) | 315 (21.86%) |
| Slightly limited | 507 (29.22%) | 489 (28.58%) | 441 (29.58%) | 421 (29.22%) |
| Not limited | 567 (32.68%) | 543 (31.74%) | 473 (31.72%) | 431 (29.91%) |
| Other reasons | 13 (0.75%) | 18 (1.05%) | 12 (0.80%) | 15 (1.04%) |
| Total | 1735 | 1711 | 1491 | 1441 |
| 1 month after treatment | | | | |
| Severely limited | 32 (1.84%) | 30 (1.74%) | 24 (1.62%) | 26 (1.80%) |
| Moderately limited | 196 (11.26%) | 182 (10.57%) | 166 (11.20%) | 161 (11.17%) |
| Mildly limited | 315 (18.09%) | 324 (18.82%) | 278 (18.76%) | 273 (18.93%) |
| Slightly limited | 540 (31.02%) | 530 (30.78%) | 459 (30.97%) | 449 (31.14%) |
| Not limited | 648 (37.22%) | 644 (37.40%) | 546 (36.84%) | 524 (36.34%) |
| Other reasons | 10 (0.57%) | 12 (0.70%) | 9 (0.61%) | 9 (0.62%) |
| Total | 1741 | 1722 | 1482 | 1442 |
| 3 months after treatment | | | | |
| Severely limited | 21 (1.20%) | 27 (1.57%) | 16 (1.09%) | 19 (1.33%) |
| Moderately limited | 162 (9.29%) | 159 (9.22%) | 137 (9.34%) | 136 (9.52%) |
| Mildly limited | 311 (17.84%) | 288 (16.71%) | 268 (18.27%) | 241 (16.86%) |
| Slightly limited | 528 (30.29%) | 556 (32.25%) | 441 (30.06%) | 473 (33.10%) |
| Not limited | 709 (40.68%) | 683 (39.62%) | 594 (40.49%) | 553 (38.70%) |
| Other reasons | 12 (0.69%) | 11 (0.64%) | 11 (0.75%) | 7 (0.49%) |
| Total | 1743 | 1724 | 1467 | 1429 |
| 6 months after treatment | | | | |
| Severely limited | 20 (1.15%) | 21 (1.22%) | 12 (0.83%) | 11 (0.78%) |
| Moderately limited | 137 (7.86%) | 131 (7.59%) | 109 (7.53%) | 104 (7.42%) |
| Mildly limited | 292 (16.75%) | 286 (16.58%) | 244 (16.86%) | 231 (16.48%) |
| Slightly limited | 526 (30.18%) | 539 (31.25%) | 433 (29.92%) | 453 (32.31%) |
| Not limited | 755 (43.32%) | 740 (42.90%) | 637 (44.02%) | 598 (42.65%) |
| Other reasons | 13 (0.75%) | 8 (0.46%) | 12 (0.83%) | 5 (0.36%) |
| Total | 1743 | 1725 | 1447 | 1402 |
| 9 months after treatment | | | | |
| Severely limited | 17 (0.98%) | 17 (0.99%) | 9 (0.63%) | 6 (0.44%) |
| Moderately limited | 103 (5.91%) | 105 (6.09%) | 77 (5.37%) | 73 (5.30%) |
| Mildly limited | 284 (16.29%) | 293 (16.99%) | 226 (15.75%) | 235 (17.05%) |
| Slightly limited | 503 (28.86%) | 493 (28.58%) | 408 (28.43%) | 400 (29.03%) |
| Not limited | 825 (47.33%) | 805 (46.67%) | 705 (49.13%) | 656 (47.61%) |
| Other reasons | 11 (0.63%) | 12 (0.70%) | 10 (0.70%) | 8 (0.58%) |
| Total | 1743 | 1725 | 1435 | 1378 |
| 12 months after treatment | | | | |
| Severely limited | 13 (0.75%) | 17 (0.99%) | 3 (0.21%) | 6 (0.44%) |
| Moderately limited | 79 (4.53%) | 82 (4.75%) | 52 (3.66%) | 49 (3.60%) |
| Mildly limited | 260 (14.92%) | 260 (15.07%) | 198 (13.93%) | 205 (15.04%) |
| Slightly limited | 517 (29.66%) | 511 (29.62%) | 422 (29.70%) | 411 (30.15%) |

TABLE 45-continued different observations (Question 1-5)

| | FAS | | PP | |
|---|---|---|---|---|
| Items | Control group | Trial group | Control group | Trial group |
| Not limited | 863 (49.51%) | 843 (48.87%) | 736 (51.79%) | 685 (50.26%) |
| Other reasons | 11 (0.63%) | 12 (0.70%) | 10 (0.70%) | 7 (0.51%) |
| Total | 1743 | 1725 | 1421 | 1363 |
| Follow-up | | | | |
| Severely limited | 9 (0.62%) | 6 (0.43%) | 9 (0.64%) | 6 (0.44%) |
| Moderately limited | 57 (3.96%) | 62 (4.47%) | 57 (4.05%) | 61 (4.51%) |
| Mildly limited | 189 (13.12%) | 199 (14.34%) | 181 (12.87%) | 195 (14.42%) |
| Slightly limited | 395 (27.41%) | 397 (28.60%) | 386 (27.45%) | 389 (28.77%) |
| Not limited | 783 (54.34%) | 717 (51.66%) | 765 (54.41%) | 694 (51.33%) |
| Other reasons | 8 (0.56%) | 7 (0.50%) | 8 (0.57%) | 7 (0.52%) |
| Total | 1441 | 1388 | 1406 | 1352 |

TABLE 46 test of different observations (Question 1-5)

| | | FAS | | PP | |
|---|---|---|---|---|---|
| Items | Test method | Statistic | P value | Statistic | P value |
| Baseline | Rank-sum test | −0.55 | 0.5790 | −1.05 | 0.2935 |
| 1 month after treatment | Rank-sum test | 0.28 | 0.7792 | −0.27 | 0.7871 |
| 3 months after treatment | Rank-sum test | −0.28 | 0.7809 | −0.60 | 0.5495 |
| 6 months after treatment | Rank-sum test | −0.23 | 0.8186 | −0.63 | 0.5305 |
| 9 months after treatment | Rank-sum test | −0.47 | 0.6353 | −0.85 | 0.3927 |
| 12 months after treatment | Rank-sum test | −0.44 | 0.6574 | −1.05 | 0.2944 |
| Follow-up | Rank-sum test | −1.48 | 0.1377 | −1.68 | 0.0935 |

TABLE 47 different observations (Question 1-6)

| | FAS | | PP | |
|---|---|---|---|---|
| Items | Control group | Trial group | Control group | Trial group |
| Baseline | | | | |
| Severely limited | 117 (6.75%) | 105 (6.14%) | 104 (6.99%) | 95 (6.61%) |
| Moderately limited | 311 (17.95%) | 334 (19.53%) | 274 (18.43%) | 298 (20.72%) |
| Mildly limited | 362 (20.89%) | 347 (20.29%) | 306 (20.58%) | 284 (19.75%) |
| Slightly limited | 479 (27.64%) | 493 (28.83%) | 416 (27.98%) | 424 (29.49%) |
| Not limited | 448 (25.85%) | 414 (24.21%) | 372 (25.02%) | 323 (22.46%) |
| Other reasons | 16 (0.92%) | 17 (0.99%) | 15 (1.01%) | 14 (0.97%) |
| Total | 1733 | 1710 | 1487 | 1438 |
| 1 month after treatment | | | | |
| Severely limited | 90 (5.18%) | 82 (4.77%) | 70 (4.75%) | 73 (5.08%) |
| Moderately limited | 258 (14.85%) | 257 (14.94%) | 229 (15.53%) | 228 (15.87%) |
| Mildly limited | 322 (18.54%) | 335 (19.48%) | 269 (18.24%) | 269 (18.72%) |
| Slightly limited | 539 (31.03%) | 550 (31.98%) | 465 (31.53%) | 473 (32.92%) |
| Not limited | 514 (29.59%) | 481 (27.97%) | 429 (29.08%) | 383 (26.65%) |
| Other reasons | 14 (0.81%) | 15 (0.87%) | 13 (0.88%) | 11 (0.77%) |
| Total | 1737 | 1720 | 1475 | 1437 |
| 3 months after treatment | | | | |
| Severely limited | 72 (4.14%) | 61 (3.54%) | 56 (3.83%) | 50 (3.52%) |
| Moderately limited | 227 (13.05%) | 249 (14.47%) | 203 (13.89%) | 220 (15.48%) |
| Mildly limited | 317 (18.23%) | 298 (17.32%) | 262 (17.92%) | 229 (16.12%) |
| Slightly limited | 560 (32.20%) | 593 (34.46%) | 475 (32.49%) | 506 (35.61%) |
| Not limited | 547 (31.45%) | 504 (29.29%) | 452 (30.92%) | 405 (28.50%) |
| Other reasons | 16 (0.92%) | 16 (0.93%) | 14 (0.96%) | 11 (0.77%) |
| Total | 1739 | 1721 | 1462 | 1421 |

TABLE 47-continued different observations (Question 1-6)

| | FAS | | PP | |
|---|---|---|---|---|
| Items | Control group | Trial group | Control group | Trial group |
| 6 months after treatment | | | | |
| Severely limited | 67 (3.85%) | 56 (3.25%) | 46 (3.19%) | 43 (3.08%) |
| Moderately limited | 205 (11.78%) | 213 (12.36%) | 174 (12.07%) | 175 (12.52%) |
| Mildly limited | 287 (16.49%) | 293 (17.01%) | 234 (16.24%) | 224 (16.02%) |
| Slightly limited | 569 (32.70%) | 584 (33.89%) | 476 (33.03%) | 492 (35.19%) |
| Not limited | 595 (34.20%) | 566 (32.85%) | 495 (34.35%) | 457 (32.69%) |
| Other reasons | 17 (0.98%) | 11 (0.64%) | 16 (1.11%) | 7 (0.50%) |
| Total | 1740 | 1723 | 1441 | 1398 |
| 9 months after treatment | | | | |
| Severely limited | 51 (2.93%) | 49 (2.84%) | 33 (2.30%) | 34 (2.47%) |
| Moderately limited | 193 (11.08%) | 184 (10.67%) | 162 (11.31%) | 143 (10.41%) |
| Mildly limited | 275 (15.79%) | 289 (16.76%) | 209 (14.59%) | 218 (15.87%) |
| Slightly limited | 558 (32.03%) | 559 (32.42%) | 464 (32.40%) | 457 (33.26%) |
| Not limited | 650 (37.31%) | 631 (36.60%) | 551 (38.48%) | 515 (37.48%) |
| Other reasons | 15 (0.86%) | 12 (0.70%) | 13 (0.91%) | 7 (0.51%) |
| Total | 1742 | 1724 | 1432 | 1374 |
| 12 months after treatment | | | | |
| Severely limited | 45 (2.58%) | 38 (2.20%) | 25 (1.76%) | 21 (1.55%) |
| Moderately limited | 169 (9.70%) | 147 (8.53%) | 136 (9.58%) | 105 (7.73%) |
| Mildly limited | 260 (14.93%) | 306 (17.75%) | 191 (13.45%) | 236 (17.37%) |
| Slightly limited | 548 (31.46%) | 532 (30.86%) | 453 (31.90%) | 423 (31.13%) |
| Not limited | 705 (40.47%) | 689 (39.97%) | 602 (42.39%) | 568 (41.80%) |
| Other reasons | 15 (0.86%) | 12 (0.70%) | 13 (0.92%) | 6 (0.44%) |
| Total | 1742 | 1724 | 1420 | 1359 |
| Follow-up | | | | |
| Severely limited | 32 (2.22%) | 21 (1.52%) | 32 (2.28%) | 21 (1.55%) |
| Moderately limited | 133 (9.24%) | 129 (9.31%) | 129 (9.19%) | 127 (9.40%) |
| Mildly limited | 165 (11.47%) | 186 (13.42%) | 159 (11.32%) | 179 (13.25%) |
| Slightly limited | 491 (34.12%) | 455 (32.83%) | 483 (34.40%) | 450 (33.31%) |
| Not limited | 606 (42.11%) | 588 (42.42%) | 589 (41.95%) | 567 (41.97%) |
| Other reasons | 12 (0.83%) | 7 (0.51%) | 12 (0.85%) | 7 (0.52%) |
| Total | 1439 | 1386 | 1404 | 1351 |

TABLE 48 test of different observations (Question 1-6)

| | | FAS | | PP | |
|---|---|---|---|---|---|
| Items | Test method | Statistic | P value | Statistic | P value |
| Baseline | Rank-sum test | −0.64 | 0.5197 | −1.23 | 0.2193 |
| 1 month after treatment | Rank-sum test | −0.55 | 0.5845 | −1.18 | 0.2363 |
| 3 months after treatment | Rank-sum test | −0.78 | 0.4342 | −0.87 | 0.3852 |
| 6 months after treatment | Rank-sum test | −0.74 | 0.4607 | −0.90 | 0.3661 |
| 9 months after treatment | Rank-sum test | −0.41 | 0.6850 | −0.59 | 0.5534 |
| 12 months after treatment | Rank-sum test | −0.38 | 0.7026 | −0.65 | 0.5167 |
| Follow-up | Rank-sum test | −0.26 | 0.7928 | −0.41 | 0.6830 |

TABLE 49 different observations (Question 1-7)

| | FAS | | PP | |
|---|---|---|---|---|
| Items | Control group | Trial group | Control group | Trial group |
| Baseline | | | | |
| Severely limited | 358 (20.94%) | 340 (20.02%) | 315 (21.49%) | 298 (20.84%) |
| Moderately limited | 332 (19.42%) | 355 (20.91%) | 285 (19.44%) | 315 (22.03%) |
| Mildly limited | 423 (24.74%) | 416 (24.50%) | 367 (25.03%) | 343 (23.99%) |

TABLE 49-continued

| | different observations (Question 1-7) | | | |
|---|---|---|---|---|
| | FAS | | PP | |
| Items | Control group | Trial group | Control group | Trial group |
| Slightly limited | 367 (21.46%) | 381 (22.44%) | 312 (21.28%) | 319 (22.31%) |
| Not limited | 182 (10.64%) | 158 (9.31%) | 141 (9.62%) | 114 (7.97%) |
| Other reasons | 48 (2.81%) | 48 (2.83%) | 46 (3.14%) | 41 (2.87%) |
| Total | 1710 | 1698 | 1466 | 1430 |
| 1 month after treatment | | | | |
| Severely limited | 304 (17.68%) | 303 (17.74%) | 259 (17.75%) | 268 (18.75%) |
| Moderately limited | 300 (17.45%) | 285 (16.69%) | 256 (17.55%) | 241 (16.86%) |
| Mildly limited | 408 (23.73%) | 425 (24.88%) | 348 (23.85%) | 348 (24.35%) |
| Slightly limited | 437 (25.42%) | 447 (26.17%) | 371 (25.43%) | 374 (26.17%) |
| Not limited | 221 (12.86%) | 198 (11.59%) | 180 (12.34%) | 155 (10.85%) |
| Other reasons | 49 (2.85%) | 50 (2.93%) | 45 (3.08%) | 43 (3.01%) |
| Total | 1719 | 1708 | 1459 | 1429 |
| 3 months after treatment | | | | |
| Severely limited | 274 (15.88%) | 281 (16.42%) | 232 (16.01%) | 245 (17.31%) |
| Moserately limited | 260 (15.07%) | 244 (14.26%) | 216 (14.91%) | 195 (13.78%) |
| Mildly limited | 410 (23.77%) | 435 (25.42%) | 345 (23.81%) | 359 (25.37%) |
| Slightly limited | 489 (28.35%) | 484 (28.29%) | 416 (28.71%) | 406 (28.69%) |
| Not limited | 240 (13.91%) | 217 (12.68%) | 195 (13.46%) | 172 (12.16%) |
| Other reasons | 52 (3.01%) | 50 (2.92%) | 45 (3.11%) | 38 (2.69%) |
| Total | 1725 | 1711 | 1449 | 1415 |
| 6 months after treatment | | | | |
| Severely limited | 265 (15.33%) | 258 (15.08%) | 213 (14.88%) | 210 (15.20%) |
| Moderately limited | 233 (13.48%) | 233 (13.62%) | 180 (12.58%) | 173 (12.52%) |
| Mildly limited | 367 (21.23%) | 380 (22.21%) | 307 (21.45%) | 312 (22.58%) |
| Slightly limited | 552 (31.93%) | 538 (31.44%) | 471 (32.91%) | 449 (32.49%) |
| Not limited | 251 (14.52%) | 242 (14.14%) | 207 (14.47%) | 191 (13.82%) |
| Other reasons | 61 (3.53%) | 60 (3.51%) | 53 (3.70%) | 47 (3.40%) |
| Total | 1729 | 1711 | 1431 | 1382 |
| 9 months after treatment | | | | |
| Severely limited | 247 (14.29%) | 239 (13.97%) | 194 (13.71%) | 190 (14.00%) |
| Moderately limited | 205 (11.86%) | 230 (13.44%) | 154 (10.88%) | 158 (11.64%) |
| Mildly limited | 375 (21.69%) | 353 (20.63%) | 306 (21.63%) | 281 (20.71%) |
| Slightly limited | 540 (31.23%) | 554 (32.38%) | 456 (32.23%) | 463 (34.12%) |
| Not limited | 309 (17.87%) | 278 (16.25%) | 259 (18.30%) | 222 (16.36%) |
| Other reasons | 53 (3.07%) | 57 (3.33%) | 46 (3.25%) | 43 (3.17%) |
| Total | 1729 | 1711 | 1415 | 1357 |
| 12 months after treatment | | | | |
| Severely limited | 224 (12.95%) | 220 (12.86%) | 169 (12.05%) | 169 (12.56%) |
| Moderately limited | 192 (11.10%) | 209 (12.22%) | 138 (9.84%) | 137 (10.18%) |
| Mildly limited | 354 (20.46%) | 353 (20.63%) | 284 (20.24%) | 280 (20.80%) |
| Slightly limited | 549 (31.73%) | 552 (32.26%) | 456 (32.50%) | 456 (33.88%) |
| Not limited | 354 (20.46%) | 315 (18.41%) | 306 (21.81%) | 258 (19.17%) |
| Other limited | 57 (3.29%) | 62 (3.62%) | 50 (3.56%) | 46 (3.42%) |
| Total | 1730 | 1711 | 1403 | 1346 |
| Follow-up | | | | |
| Severely limited | 166 (11.67%) | 172 (12.55%) | 162 (11.68%) | 167 (12.51%) |
| Moderately limited | 96 (6.75%) | 102 (7.45%) | 92 (6.63%) | 101 (7.57%) |
| Mildly limited | 313 (22.01%) | 285 (20.80%) | 304 (21.92%) | 278 (20.82%) |
| Slightly limited | 497 (34.95%) | 489 (35.69%) | 483 (34.82%) | 478 (35.81%) |
| Not limited | 314 (22.08%) | 295 (21.53%) | 310 (22.35%) | 284 (21.27%) |
| Other reasons | 36 (2.53%) | 27 (1.97%) | 36 (2.60%) | 27 (2.02%) |
| Total | 1422 | 1370 | 1387 | 1335 |

TABLE 50 test of different observations (Question 1-7)

| Items | Test method | FAS Statistic | FAS P value | PP Statistic | PP P value |
|---|---|---|---|---|---|
| Baseline | Rank-sum test | −0.24 | 0.8095 | −0.78 | 0.4353 |
| 1 month after treatment | Rank-sum test | −0.20 | 0.8421 | −0.71 | 0.4769 |
| 3 months after treatment | Rank-sum test | −0.71 | 0.4807 | −1.04 | 0.3003 |
| 6 months after treatment | Rank-sum test | −0.28 | 0.7763 | −0.67 | 0.5024 |
| 9 months after treatment | Rank-sum test | −0.56 | 0.5786 | −0.72 | 0.4741 |
| 12 months after treatment | Rank-sum test | −0.91 | 0.3617 | −1.25 | 0.2130 |
| Follow-up | Rank-sum test | −0.76 | 0.4501 | −0.99 | 0.3216 |

TABLE 51 different observations (Question 1-8)

| Items | FAS Control group | FAS Trial group | PP Control group | PP Trial group |
|---|---|---|---|---|
| Baseline | | | | |
| Severely limited | 444 (25.96%) | 429 (25.34%) | 388 (26.45%) | 376 (26.37%) |
| Moderately limited | 386 (22.57%) | 408 (24.10%) | 329 (22.43%) | 348 (24.40%) |
| Mildly limited | 404 (23.63%) | 399 (23.57%) | 358 (24.40%) | 335 (23.49%) |
| Slightly limited | 297 (17.37%) | 278 (16.42%) | 246 (16.77%) | 229 (16.06%) |
| Not limited | 138 (8.07%) | 140 (8.27%) | 109 (7.43%) | 106 (7.43%) |
| Other reasons | 41 (2.40%) | 39 (2.30%) | 37 (2.52%) | 32 (2.24%) |
| Total | 1710 | 1693 | 1467 | 1426 |
| 1 month after treatment | | | | |
| Severely limited | 383 (22.27%) | 367 (21.51%) | 327 (22.37%) | 323 (22.60%) |
| Moderately limited | 353 (20.52%) | 353 (20.69%) | 304 (20.79%) | 291 (20.36%) |
| Mildly limited | 415 (24.13%) | 443 (25.97%) | 363 (24.83%) | 378 (26.45%) |
| Slightly limited | 366 (21.28%) | 340 (19.93%) | 305 (20.86%) | 274 (19.17%) |
| Not limited | 155 (9.01%) | 164 (9.61%) | 121 (8.28%) | 130 (9.10%) |
| Other reasons | 48 (2.79%) | 39 (2.29%) | 42 (2.87%) | 33 (2.31%) |
| Total | 1720 | 1706 | 1462 | 1429 |
| 3 months after treatment | | | | |
| Severely limieted | 362 (21.02%) | 360 (21.08%) | 307 (21.30%) | 305 (21.62%) |
| Moderately limited | 308 (17.89%) | 305 (17.86%) | 258 (17.90%) | 248 (17.58%) |
| Mildly limited | 440 (25.55%) | 456 (26.70%) | 372 (25.82%) | 385 (27.29%) |
| Slightly limited | 376 (21.84%) | 357 (20.90%) | 311 (21.58%) | 292 (20.69%) |
| Not limited | 184 (10.69%) | 189 (11.07%) | 151 (10.48%) | 149 (10.56%) |
| Other reasons | 52 (3.02%) | 41 (2.40%) | 42 (2.91%) | 32 (2.27%) |
| Total | 1722 | 1708 | 1441 | 1411 |
| 6 months after treatment | | | | |
| Severely limited | 334 (19.38%) | 331 (19.37%) | 270 (18.96%) | 269 (19.51%) |
| Moderately limited | 283 (16.42%) | 292 (17.09%) | 228 (16.01%) | 222 (16.10%) |
| Mildly limited | 436 (25.30%) | 447 (26.16%) | 369 (25.91%) | 374 (27.12%) |
| Slightly limited | 422 (24.49%) | 386 (22.59%) | 349 (24.51%) | 312 (22.63%) |
| Not limited | 183 (10.62%) | 205 (12.00%) | 154 (10.81%) | 165 (11.97%) |
| Other reasons | 65 (3.77%) | 48 (2.81%) | 54 (3.79%) | 37 (2.68%) |
| Total | 1723 | 1709 | 1424 | 1379 |
| 9 months after treatment | | | | |
| Severely limited | 309 (17.93%) | 311 (18.20%) | 243 (17.23%) | 241 (17.76%) |
| Moderately limited | 259 (15.03%) | 264 (15.45%) | 199 (14.11%) | 189 (13.93%) |
| Mildly limited | 423 (24.55%) | 428 (25.04%) | 354 (25.11%) | 355 (26.16%) |
| Slightly limited | 464 (26.93%) | 433 (25.34%) | 387 (27.45%) | 353 (26.01%) |
| Not limited | 206 (11.96%) | 217 (12.70%) | 174 (12.34%) | 175 (12.90%) |
| Other limited | 62 (3.60%) | 56 (3.28%) | 53 (3.76%) | 44 (3.24%) |
| Total | 1723 | 1709 | 1410 | 1357 |
| 12 months after treatment | | | | |
| Severely limited | 291 (16.89%) | 299 (17.50%) | 219 (15.68%) | 222 (16.55%) |
| Moderately limited | 230 (13.35%) | 247 (14.45%) | 170 (12.17%) | 177 (13.20%) |
| Mildly limited | 426 (24.72%) | 411 (24.05%) | 349 (24.98%) | 333 (24.83%) |
| Slightly limited | 473 (27.45%) | 448 (26.21%) | 397 (28.42%) | 361 (26.92%) |

TABLE 51-continued different observations (Question 1-8)

| | FAS | | PP | |
|---|---|---|---|---|
| Items | Control group | Trial group | Control group | Trial group |
| Not limited | 235 (13.64%) | 241 (14.10%) | 203 (14.53%) | 198 (14.77%) |
| Other reasons | 68 (3.95%) | 63 (3.69%) | 59 (4.22%) | 50 (3.73%) |
| Total | 1723 | 1709 | 1397 | 1341 |
| Follow-up | | | | |
| Severely limited | 208 (14.74%) | 210 (15.37%) | 203 (14.75%) | 205 (15.40%) |
| Moderately limited | 168 (11.91%) | 182 (13.32%) | 163 (11.85%) | 178 (13.37%) |
| Mildly limited | 353 (25.02%) | 335 (24.52%) | 343 (24.93%) | 329 (24.72%) |
| Slightly limited | 425 (30.12%) | 388 (28.40%) | 414 (30.09%) | 375 (28.17%) |
| Not limited | 212 (15.02%) | 215 (15.74%) | 208 (15.12%) | 208 (15.63%) |
| Other reasons | 45 (3.19%) | 36 (2.64%) | 45 (3.27%) | 36 (2.70%) |
| Total | 1411 | 1366 | 1376 | 1331 |

TABLE 52 test of different observations (Question 1-8)

| | | FAS | | PP | |
|---|---|---|---|---|---|
| Items | Test method | Statistic | P value | Statistic | P value |
| Baseline | Rank-sum test | −0.23 | 0.8193 | −0.64 | 0.5196 |
| 1 month after treatment | Rank-sum test | −0.01 | 0.9943 | −0.31 | 0.7548 |
| 3 months after treatment | Rank-sum test | −0.39 | 0.6969 | −0.51 | 0.6122 |
| 6 months after treatment | Rank-sum test | −0.52 | 0.6032 | −0.72 | 0.4724 |
| 9 months after treatment | Rank-sum test | −0.44 | 0.6604 | −0.51 | 0.6086 |
| 12 months after treatment | Rank-sum test | −0.69 | 0.4877 | −0.97 | 0.3307 |
| Follow-up | Rank-sum test | −0.85 | 0.3968 | −1.01 | 0.3130 |

TABLE 53 different observations (Question 1-9)

| | FAS | | PP | |
|---|---|---|---|---|
| Items | Control group | Trial group | Control group | Trial group |
| Baseline | | | | |
| Severely limited | 802 (47.34%) | 818 (48.69%) | 705 (48.55%) | 711 (50.25%) |
| Moderately limited | 359 (21.19%) | 341 (20.30%) | 301 (20.73%) | 277 (19.58%) |
| Mildly limited | 249 (14.70%) | 244 (14.52%) | 213 (14.67%) | 200 (14.13%) |
| Slightly limited | 145 (8.56%) | 142 (8.45%) | 108 (7.44%) | 111 (7.84%) |
| Not limited | 40 (2.36%) | 36 (2.14%) | 33 (2.27%) | 28 (1.98%) |
| Other reasons | 99 (5.84%) | 99 (5.89%) | 92 (6.34%) | 88 (6.22%) |
| Total | 1694 | 1680 | 1452 | 1415 |
| 1 month after treatment | | | | |
| Severely limited | 714 (41.93%) | 716 (42.24%) | 617 (42.70%) | 613 (43.35%) |
| Moderately limited | 358 (21.02%) | 341 (20.12%) | 310 (21.45%) | 285 (20.16%) |
| Mildly limited | 284 (16.68%) | 314 (18.53%) | 239 (16.54%) | 262 (18.53%) |
| Slightly limited | 193 (11.33%) | 172 (10.15%) | 143 (9.90%) | 131 (9.26%) |
| Not limited | 49 (2.88%) | 54 (3.19%) | 43 (2.98%) | 38 (2.69%) |
| Other reasons | 105 (6.17%) | 98 (5.78%) | 93 (6.44%) | 85 (6.01%) |
| Total | 1703 | 1695 | 1445 | 1414 |
| 3 months after treatment | | | | |
| Severely limited | 664 (38.90%) | 677 (39.85%) | 564 (39.41%) | 565 (40.41%) |
| Moderately limited | 342 (20.04%) | 338 (19.89%) | 293 (20.48%) | 281 (20.10%) |
| Mildly limited | 318 (18.63%) | 312 (18.36%) | 264 (18.45%) | 266 (19.03%) |
| Slightly limited | 220 (12.89%) | 205 (12.07%) | 170 (11.88%) | 153 (10.94%) |
| Not limited | 61 (3.57%) | 70 (4.12%) | 53 (3.70%) | 56 (4.01%) |
| Other reaons | 102 (5.98%) | 97 (5.71%) | 87 (6.08%) | 77 (5.51%) |
| Total | 1707 | 1699 | 1431 | 1398 |

TABLE 53-continued different observations (Question 1-9)

| | FAS | | PP | |
|---|---|---|---|---|
| Items | Control group | Trial group | Control group | Trial group |
| 6 months after treatment | | | | |
| Severely limited | 606 (35.42%) | 625 (36.76%) | 490 (34.70%) | 498 (36.32%) |
| Moderately limited | 357 (20.86%) | 339 (19.94%) | 305 (21.60%) | 276 (20.13%) |
| Mildly limited | 341 (19.93%) | 332 (19.53%) | 289 (20.47%) | 283 (20.64%) |
| Slightly limited | 243 (14.20%) | 230 (13.53%) | 188 (13.31%) | 179 (13.06%) |
| Not limited | 58 (3.39%) | 72 (4.24%) | 50 (3.54%) | 54 (3.94%) |
| Other limited | 106 (6.20%) | 102 (6.00%) | 90 (6.37%) | 81 (5.91%) |
| Total | 1711 | 1700 | 1412 | 1371 |
| 9 months after treatment | | | | |
| Severely limited | 572 (33.39%) | 585 (34.41%) | 452 (32.38%) | 443 (32.96%) |
| Moderately limited | 353 (20.61%) | 348 (20.47%) | 292 (20.92%) | 282 (20.98%) |
| Mildly limited | 332 (19.38%) | 340 (20.00%) | 275 (19.70%) | 288 (21.43%) |
| Slightly limited | 293 (17.10%) | 258 (15.18%) | 237 (16.98%) | 207 (15.40%) |
| Not limited | 67 (3.91%) | 70 (4.12%) | 59 (4.23%) | 47 (3.50%) |
| Other reasons | 96 (5.60%) | 99 (5.82%) | 81 (5.80%) | 77 (5.73%) |
| Total | 1713 | 1700 | 1396 | 1344 |
| 12 months after treatment | | | | |
| Severely limited | 542 (31.62%) | 552 (32.47%) | 412 (29.75%) | 406 (30.55%) |
| Moderately limited | 350 (20.42%) | 345 (20.29%) | 289 (20.87%) | 276 (20.77%) |
| Mildly limited | 336 (19.60%) | 322 (18.94%) | 278 (20.07%) | 271 (20.39%) |
| Slightly limited | 307 (17.91%) | 290 (17.06%) | 249 (17.98%) | 234 (17.61%) |
| Not limited | 78 (4.55%) | 92 (5.41%) | 70 (5.05%) | 67 (5.04%) |
| Other reasons | 101 (5.89%) | 99 (5.82%) | 87 (6.28%) | 75 (5.64%) |
| Total | 1714 | 1700 | 1385 | 1329 |
| Follow-up | | | | |
| Severely-limited | 379 (27.13%) | 380 (28.23%) | 372 (27.29%) | 374 (28.53%) |
| Moderately limited | 296 (21.19%) | 294 (21.84%) | 288 (21.13%) | 283 (21.59%) |
| Mildly limited | 285 (20.40%) | 264 (19.61%) | 276 (20.25%) | 259 (19.76%) |
| Slightly limited | 287 (20.54%) | 276 (20.51%) | 279 (20.47%) | 268 (20.44%) |
| Not limited | 85 (6.08%) | 73 (5.42%) | 83 (6.09%) | 68 (5.19%) |
| Other reasons | 65 (4.65%) | 59 (4.38%) | 65 (4.77%) | 59 (4.50%) |
| Total | 1397 | 1346 | 1363 | 1311 |

TABLE 54 test of different observations (Question 1-9)

| | | FAS | | PP | |
|---|---|---|---|---|---|
| Items | Test method | Statistic | P value | Statistic | P value |
| Baseline | Rank-sum test | −0.63 | 0.5316 | −0.70 | 0.4812 |
| 1 month after treatment | Rank-sum test | −0.20 | 0.8424 | −0.32 | 0.7475 |
| 3 months after treatment | Rank-sum test | −0.54 | 0.5911 | −0.63 | 0.5301 |
| 6 months after treatment | Rank-sum test | −0.44 | 0.6593 | −0.54 | 0.5887 |
| 9 months after treatment | Rank-sum test | −0.70 | 0.4839 | −0.76 | 0.4486 |
| 12 months after treatment | Rank-sum test | −0.30 | 0.7617 | −0.60 | 0.5458 |
| Follow-up | Rank-sum test | −0.90 | 0.3681 | −0.98 | 0.3292 |

TABLE 55 different observations ($2^{nd}$ question)

| | FAS | | PP | |
|---|---|---|---|---|
| Items | Control group | Trial group | Control group | Trial group |
| Baseline | | | | |
| Clearly increased | 55 (3.17%) | 59 (3.45%) | 46 (3.09%) | 46 (3.19%) |
| Slightly increased | 120 (6.92%) | 122 (7.13%) | 100 (6.72%) | 104 (7.22%) |
| Same | 1076 (62.09%) | 1091 (63.73%) | 938 (63.00%) | 938 (65.14%) |

TABLE 55-continued

| | different observations (2$^{nd}$ question) | | | |
|---|---|---|---|---|
| | FAS | | PP | |
| Items | Control group | Trial group | Control group | Trial group |
| Slightly reduced | 266 (15.35%) | 260 (15.19%) | 224 (15.04%) | 209 (14.51%) |
| Clearly reduced | 216 (12.46%) | 180 (10.51%) | 181 (12.16%) | 143 (9.93%) |
| Total | 1733 | 1712 | 1489 | 1440 |
| 1 month after treatment | | | | |
| Clearly increased | 16 (0.92%) | 14 (0.81%) | 8 (0.54%) | 9 (0.62%) |
| Slightly increased | 53 (3.05%) | 51 (2.96%) | 43 (2.90%) | 43 (2.98%) |
| Same | 853 (49.05%) | 831 (48.29%) | 735 (49.63%) | 698 (48.44%) |
| Slightly reduced | 530 (30.48%) | 544 (31.61%) | 447 (30.18%) | 451 (31.30%) |
| Clearly reduced | 287 (16.50%) | 281 (16.33%) | 248 (16.75%) | 240 (16.66%) |
| Total | 1739 | 1721 | 1481 | 1441 |
| 3 months after treatment | | | | |
| Clearly increased | 16 (0.92%) | 15 (0.87%) | 6 (0.41%) | 7 (0.49%) |
| Slightly increased | 66 (3.79%) | 59 (3.42%) | 50 (3.42%) | 42 (2.94%) |
| Same | 733 (42.13%) | 698 (40.51%) | 614 (41.97%) | 574 (40.20%) |
| Slightly reduced | 557 (32.01%) | 592 (34.36%) | 471 (32.19%) | 499 (34.94%) |
| Clearly reduced | 368 (21.15%) | 359 (20.84%) | 322 (22.01%) | 306 (21.43%) |
| Total | 1740 | 1723 | 1463 | 1428 |
| 6 months after treatment | | | | |
| Clearly increased | 17 (0.98%) | 25 (1.45%) | 3 (0.21%) | 10 (0.71%) |
| Slightly increased | 64 (3.68%) | 69 (4.00%) | 40 (2.76%) | 48 (3.42%) |
| Same | 650 (37.33%) | 584 (33.89%) | 528 (36.46%) | 460 (32.79%) |
| Slightly reduced | 610 (35.04%) | 658 (38.19%) | 522 (36.05%) | 554 (39.49%) |
| Clearly reduced | 400 (22.98%) | 386 (22.40%) | 355 (24.52%) | 331 (23.59%) |
| 6 | 0 (0.00%) | 1 (0.06%) | | |
| Total | 1741 | 1723 | 1448 | 1403 |
| 9 months after treatment | | | | |
| Clearly increased | 25 (1.44%) | 29 (1.68%) | 9 (0.63%) | 7 (0.51%) |
| Slightly increased | 69 (3.96%) | 58 (3.37%) | 46 (3.21%) | 31 (2.24%) |
| Same | 626 (35.94%) | 583 (33.84%) | 501 (34.94%) | 450 (32.59%) |
| Slightly reduced | 601 (34.50%) | 620 (35.98%) | 505 (35.22%) | 515 (37.29%) |
| Clearly reduced | 421 (24.17%) | 432 (25.07%) | 373 (26.01%) | 378 (27.37%) |
| 6 | 0 (0.00%) | 1 (0.06%) | | |
| Total | 1742 | 1723 | 1434 | 1381 |
| 12 months after treatment | | | | |
| Clearly increased | 23 (1.32%) | 30 (1.74%) | 2 (0.14%) | 4 (0.29%) |
| Slightly increased | 55 (3.16%) | 62 (3.60%) | 28 (1.96%) | 34 (2.49%) |
| Same | 659 (37.83%) | 638 (37.03%) | 528 (37.05%) | 500 (36.63%) |
| Slightly reduced | 525 (30.14%) | 510 (29.60%) | 439 (30.81%) | 404 (29.60%) |
| Clearly reduced | 480 (27.55%) | 482 (27.97%) | 428 (30.04%) | 423 (30.99%) |
| 6 | 0 (0.00%) | 1 (0.06%) | | |
| Total | 1742 | 1723 | 1425 | 1365 |
| Follow-up | | | | |
| Clearly increased | 3 (0.21%) | 6 (0.43%) | 3 (0.21%) | 6 (0.44%) |
| Slightly increased | 107 (7.40%) | 130 (9.36%) | 104 (7.38%) | 127 (9.39%) |
| Same | 567 (39.24%) | 552 (39.74%) | 552 (39.15%) | 539 (39.84%) |
| Slightly reduced | 366 (25.33%) | 315 (22.68%) | 361 (25.60%) | 305 (22.54%) |
| Clearly reduced | 402 (27.82%) | 386 (27.79%) | 390 (27.66%) | 376 (27.79%) |
| Total | 1445 | 1389 | 1410 | 1353 |

TABLE 56 test of different observations (2$^{nd}$ question)

| Items | Test method | FAS Statistic | FAS P value | PP Statistic | PP P value |
|---|---|---|---|---|---|
| Baseline | Rank-sum test | −1.49 | 0.1361 | −1.75 | 0.0805 |
| 1 month after treatment | Rank-sum test | 0.43 | 0.6660 | 0.35 | 0.7274 |
| 3 months after treatment | Rank-sum test | 0.83 | 0.4054 | 0.73 | 0.4662 |
| 6 months after treatment | Rank-sum test | 0.69 | 0.4929 | 0.39 | 0.6986 |
| 9 months after treatment | Rank-sum test | 1.30 | 0.1920 | 1.78 | 0.0754 |
| 12 months after treatment | Rank-sum test | −0.07 | 0.9480 | 0.07 | 0.9466 |
| Follow-up | Rank-sum test | −1.35 | 0.1774 | −1.38 | 0.1666 |

TABLE 57 different observations (3$^{rd}$ question)

| Items | FAS Control group | FAS Trial group | PP Control group | PP Trial group |
|---|---|---|---|---|
| Baseline | | | | |
| ≥4 times per day | 55 (3.17%) | 59 (3.45%) | 46 (3.09%) | 46 (3.19%) |
| 1-3 times per day | 120 (6.92%) | 122 (7.13%) | 100 (6.72%) | 104 (7.22%) |
| ≥3 times per week | 1076 (62.09%) | 1091 (63.73%) | 938 (63.00%) | 938 (65.14%) |
| 1-2 times per week | 266 (15.35%) | 260 (15.19%) | 224 (15.04%) | 209 (14.51%) |
| <1 time per week | 216 (12.46%) | 180 (10.51%) | 181 (12.16%) | 143 (9.93%) |
| No onset | 0 (0.00%) | 0 (0.00%) | 0 (0.00%) | 0 (0.00%) |
| Total | 1733 | 1712 | 1489 | 1440 |
| 1 month after treatment | | | | |
| ≥4 times per day | 16 (0.92%) | 14 (0.81%) | 8 (0.54%) | 9 (0.62%) |
| 1-3 times per day | 53 (3.05%) | 51 (2.96%) | 43 (2.90%) | 43 (2.98%) |
| ≥3 times per week | 853 (49.05%) | 831 (48.29%) | 735 (49.63%) | 698 (48.44%) |
| 1-2 times per week | 530 (30.48%) | 544 (31.61%) | 447 (30.18%) | 451 (31.30%) |
| <1 time per week | 287 (16.50%) | 281 (16.33%) | 248 (16.75%) | 240 (16.66%) |
| No onset | 0 (0.00%) | 0 (0.00%) | 0 (0.00%) | 0 (0.00%) |
| Total | 1739 | 1721 | 1481 | 1441 |
| 3 months after treatment | | | | |
| ≥4 times per day | 16 (0.92%) | 15 (0.87%) | 6 (0.41%) | 7 (0.49%) |
| 1-3 times per day | 66 (3.79%) | 59 (3.42%) | 50 (3.42%) | 42 (2.94%) |
| ≥3 times per week | 733 (42.13%) | 698 (40.51%) | 614 (41.97%) | 574 (40.20%) |
| 1-2 times per week | 557 (32.01%) | 592 (34.36%) | 471 (32.19%) | 499 (34.94%) |
| <1 time per week | 368 (21.15%) | 359 (20.84%) | 322 (22.01%) | 306 (21.43%) |
| No onset | 0 (0.00%) | 0 (0.00%) | 0 (0.00%) | 0 (0.00%) |
| Total | 1740 | 1723 | 1463 | 1428 |
| 6 months after treatment | | | | |
| ≥4 times per day | 17 (0.98%) | 25 (1.45%) | 3 (0.21%) | 10 (0.71%) |
| 1-3 times per day | 64 (3.68%) | 69 (4.00%) | 40 (2.76%) | 48 (3.42%) |
| ≥3 times per week | 650 (37.33%) | 584 (33.89%) | 528 (36.46%) | 460 (32.79%) |
| 1-2 times per week | 610 (35.04%) | 658 (38.19%) | 522 (36.05%) | 554 (39.49%) |
| <1 time per week | 400 (22.98%) | 386 (22.40%) | 355 (24.52%) | 331 (23.59%) |
| No onset | 0 (0.00%) | 1 (0.06%) | 0 (0.00%) | 0 (0.00%) |
| Total | 1741 | 1723 | 1448 | 1403 |
| 9 months after treatment | | | | |
| ≥4 times per day | 25 (1.44%) | 29 (1.68%) | 9 (0.63%) | 7 (0.51%) |
| 1-3 times per day | 69 (3.96%) | 58 (3.37%) | 46 (3.21%) | 31 (2.24%) |
| ≥3 times per week | 626 (35.94%) | 583 (33.84%) | 501 (34.94%) | 450 (32.59%) |
| 1-2 times per week | 601 (34.50%) | 620 (35.98%) | 505 (35.22%) | 515 (37.29%) |
| <1 time per week | 421 (24.17%) | 432 (25.07%) | 373 (26.01%) | 378 (27.37%) |
| No onset | 0 (0.00%) | 1 (0.06%) | 0 (0.00%) | 0 (0.00%) |
| Total | 1742 | 1723 | 1434 | 1381 |
| 12 months after treatment | | | | |
| ≥4 times per day | 23 (1.32%) | 30 (1.74%) | 2 (0.14%) | 4 (0.29%) |
| 1-3 times per day | 55 (3.16%) | 62 (3.60%) | 28 (1.96%) | 34 (2.49%) |
| ≥3 times per week | 659 (37.83%) | 638 (37.03%) | 528 (37.05%) | 500 (36.63%) |
| 1-2 times per week | 525 (30.14%) | 510 (29.60%) | 439 (30.81%) | 404 (29.60%) |

TABLE 57-continued different observations (3rd question)

| | FAS | | PP | |
|---|---|---|---|---|
| Items | Control group | Trial group | Control group | Trial group |
| <1 time per week | 480 (27.55%) | 482 (27.97%) | 428 (30.04%) | 423 (30.99%) |
| No onset | 0 (0.00%) | 1 (0.06%) | 0 (0.00%) | 0 (0.00%) |
| Total | 1742 | 1723 | 1425 | 1365 |
| Follow-up | | | | |
| ≥4 times per day | 3 (0.21%) | 6 (0.43%) | 3 (0.21%) | 6 (0.44%) |
| 1-3 times per day | 107 (7.40%) | 130 (9.36%) | 104 (7.38%) | 127 (9.39%) |
| ≥3 times per week | 567 (39.24%) | 552 (39.74%) | 552 (39.15%) | 539 (39.84%) |
| 1-2 times per week | 366 (25.33%) | 315 (22.68%) | 361 (25.60%) | 305 (22.54%) |
| <1 time per week | 402 (27.82%) | 386 (27.79%) | 390 (27.66%) | 376 (27.79%) |
| No onset | 0 (0.00%) | 0 (0.00%) | 0 (0.00%) | 0 (0.00%) |
| Total | 1445 | 1389 | 1410 | 1353 |

TABLE 58 test of different observations (3rd question)

| | | FAS | | PP | |
|---|---|---|---|---|---|
| Items | Test method | Statistic | P value | Statistic | P value |
| Baseline | Rank-sum test | −1.49 | 0.1361 | −1.75 | 0.0805 |
| 1 month after treatment | Rank-sum test | 0.43 | 0.6660 | 0.35 | 0.7274 |
| 3 months after treatment | Rank-sum test | 0.83 | 0.4054 | 0.73 | 0.4662 |
| 6 months after treatment | Rank-sum test | 0.69 | 0.4929 | 0.39 | 0.6986 |
| 9 months after treatment | Rank-sum test | 1.30 | 0.1920 | 1.78 | 0.0754 |
| 12 months after treatment | Rank-sum test | −0.07 | 0.9480 | 0.07 | 0.9466 |
| Follow-up | Rank-sum test | −1.35 | 0.1774 | −1.38 | 0.1666 |

TABLE 59 different observations (4th question)

| | FAS | | PP | |
|---|---|---|---|---|
| Items | Control group | Trial group | Control group | Trial group |
| Baseline | | | | |
| ≥4 times per day | 16 (0.92%) | 20 (1.17%) | 14 (0.94%) | 18 (1.25%) |
| 1-3 times per day | 150 (8.64%) | 133 (7.75%) | 131 (8.78%) | 120 (8.31%) |
| ≥3 times per week | 293 (16.87%) | 291 (16.96%) | 260 (17.43%) | 247 (17.11%) |
| 1-2 times per week | 344 (19.80%) | 367 (21.39%) | 301 (20.17%) | 310 (21.47%) |
| <1 time per week | 176 (10.13%) | 195 (11.36%) | 142 (9.52%) | 163 (11.29%) |
| Not used | 758 (43.64%) | 710 (41.38%) | 644 (43.16%) | 586 (40.58%) |
| Total | 1737 | 1716 | 1492 | 1444 |
| 1 month after treatment | | | | |
| ≥4 times per day | 1 (0.06%) | 8 (0.46%) | 1 (0.07%) | 8 (0.55%) |
| 1-3 times per day | 114 (6.54%) | 111 (6.44%) | 97 (6.52%) | 106 (7.33%) |
| ≥3 times per week | 230 (13.19%) | 195 (11.31%) | 204 (13.71%) | 160 (11.06%) |
| 1-2 times per week | 306 (17.55%) | 363 (21.06%) | 259 (17.41%) | 301 (20.80%) |
| <1 time per week | 167 (9.58%) | 196 (11.37%) | 135 (9.07%) | 159 (10.99%) |
| Not used | 926 (53.10%) | 851 (49.36%) | 792 (53.23%) | 713 (49.27%) |
| Total | 1744 | 1724 | 1488 | 1447 |
| 3 months after treatment | | | | |
| ≥4 times per day | 1 (0.06%) | 4 (0.23%) | 0 (0.00%) | 3 (0.21%) |
| 1-3 times per day | 97 (5.56%) | 93 (5.39%) | 78 (5.31%) | 87 (6.08%) |
| ≥3 times per week | 187 (10.72%) | 172 (9.98%) | 155 (10.55%) | 141 (9.85%) |
| 1-2 times per week | 291 (16.69%) | 336 (19.49%) | 251 (17.09%) | 280 (19.55%) |
| <1 time per week | 200 (11.47%) | 209 (12.12%) | 152 (10.35%) | 160 (11.17%) |
| Not used | 968 (55.50%) | 910 (52.78%) | 833 (56.71%) | 761 (53.14%) |
| Total | 1744 | 1724 | 1469 | 1432 |

TABLE 59-continued different observations (4th question)

| | FAS | | PP | |
|---|---|---|---|---|
| Items | Control group | Trial group | Control group | Trial group |
| 6 months after treatment | | | | |
| ≥4 times per day | 2 (0.11%) | 2 (0.12%) | 1 (0.07%) | 0 (0.00%) |
| 1-3 times per day | 82 (4.70%) | 83 (4.81%) | 56 (3.85%) | 74 (5.25%) |
| ≥3 times per week | 127 (7.28%) | 119 (6.90%) | 95 (6.53%) | 85 (6.03%) |
| 1-2 times per week | 306 (17.55%) | 324 (18.78%) | 263 (18.08%) | 261 (18.52%) |
| <1 time per week | 209 (11.98%) | 239 (13.86%) | 165 (11.34%) | 200 (14.19%) |
| Not used | 1018 (58.37%) | 958 (55.54%) | 875 (60.14%) | 789 (56.00%) |
| Total | 1744 | 1725 | 1455 | 1409 |
| 9 months after treatment | | | | |
| ≥4 times per day | 2 (0.11%) | 3 (0.17%) | 1 (0.07%) | 0 (0.00%) |
| 1-3 times per week | 75 (4.30%) | 79 (4.58%) | 49 (3.41%) | 69 (4.99%) |
| ≥3 times per week | 90 (5.16%) | 93 (5.39%) | 58 (4.03%) | 51 (3.68%) |
| 1-2 times per week | 272 (15.60%) | 255 (14.78%) | 230 (15.99%) | 191 (13.80%) |
| <1 time per week | 264 (15.14%) | 291 (16.87%) | 215 (14.95%) | 246 (17.77%) |
| Not used | 1041 (59.69%) | 1004 (58.20%) | 885 (61.54%) | 827 (59.75%) |
| Total | 1744 | 1725 | 1438 | 1384 |
| 12 months after treatment | | | | |
| ≥4 times per day | 2 (0.11%) | 4 (0.23%) | 0 (0.00%) | 1 (0.07%) |
| 1-3 times per week | 74 (4.24%) | 78 (4.52%) | 48 (3.36%) | 66 (4.82%) |
| ≥3 times per week | 69 (3.96%) | 77 (4.46%) | 32 (2.24%) | 29 (2.12%) |
| 1-2 times per week | 185 (10.61%) | 198 (11.48%) | 147 (10.29%) | 134 (9.80%) |
| <1 time per week | 288 (16.51%) | 234 (13.57%) | 234 (16.38%) | 194 (14.18%) |
| Not used | 1126 (64.56%) | 1134 (65.74%) | 968 (67.74%) | 944 (69.01%) |
| Total | 1744 | 1725 | 1429 | 1368 |
| Follow-up | | | | |
| ≥4 times per day | 0 (0.00%) | 0 (0.00%) | 0 (0.00%) | 0 (0.00%) |
| 1-3 times per week | 41 (2.84%) | 57 (4.10%) | 40 (2.83%) | 56 (4.14%) |
| ≥3 times per week | 26 (1.80%) | 25 (1.80%) | 26 (1.84%) | 25 (1.85%) |
| 1-2 times per week | 192 (13.28%) | 173 (12.45%) | 186 (13.17%) | 168 (12.41%) |
| <1 time per week | 232 (16.04%) | 234 (16.83%) | 227 (16.08%) | 233 (17.21%) |
| Not used | 955 (66.04%) | 901 (64.82%) | 933 (66.08%) | 872 (64.40%) |
| Total | 1446 | 1390 | 1412 | 1354 |

TABLE 60 test of different observations (4th question)

| | | FAS | | PP | |
|---|---|---|---|---|---|
| Items | Test method | Statistic | P value | Statistic | P value |
| Baseline | Rank-sum test | −0.63 | 0.5273 | −0.69 | 0.4891 |
| 1 month after treatment | Rank-sum test | −1.36 | 0.1727 | −1.46 | 0.1453 |
| 3 months after treatment | Rank-sum test | −1.24 | 0.2164 | −1.73 | 0.0828 |
| 6 months after treatment | Rank-sum test | −1.26 | 0.2064 | −1.91 | 0.0559 |
| 9 months after treatment | Rank-sum test | −0.68 | 0.4937 | −0.73 | 0.4657 |
| 12 months after treatment | Rank-sum test | 0.18 | 0.8556 | 0.31 | 0.7588 |
| Follow-up | Rank-sum test | −0.75 | 0.4507 | −0.96 | 0.3348 |

TABLE 61 different observations (5th question)

| | FAS | | PP | |
|---|---|---|---|---|
| Items | Control group | Trial group | Control group | Trial group |
| Baseline | | | | |
| Severe | 60 (3.45%) | 46 (2.68%) | 48 (3.21%) | 40 (2.77%) |
| Moderate | 356 (20.50%) | 391 (22.75%) | 318 (21.29%) | 349 (24.14%) |
| Mild | 534 (30.74%) | 518 (30.13%) | 467 (31.26%) | 432 (29.88%) |

TABLE 61-continued

| | different observations (5th question) | | | |
|---|---|---|---|---|
| | FAS | | PP | |
| Items | Control group | Trial group | Control group | Trial group |
| Few | 328 (18.88%) | 328 (19.08%) | 287 (19.21%) | 269 (18.60%) |
| None | 407 (23.43%) | 387 (22.51%) | 329 (22.02%) | 315 (21.78%) |
| Not medicated by doctors | 52 (2.99%) | 49 (2.85%) | 45 (3.01%) | 41 (2.84%) |
| Total | 1737 | 1719 | 1494 | 1446 |
| 1 month after treatment | | | | |
| Severe | 42 (2.41%) | 36 (2.09%) | 32 (2.15%) | 31 (2.14%) |
| Moderate | 304 (17.43%) | 288 (16.70%) | 271 (18.24%) | 245 (16.92%) |
| Mild | 504 (28.90%) | 490 (28.41%) | 430 (28.94%) | 400 (27.62%) |
| Few | 376 (21.56%) | 409 (23.71%) | 322 (21.67%) | 357 (24.65%) |
| None | 459 (26.32%) | 454 (26.32%) | 378 (25.44%) | 374 (25.83%) |
| Not medicated by doctors | 59 (3.38%) | 48 (2.78%) | 53 (3.57%) | 41 (2.83%) |
| Total | 1744 | 1725 | 1486 | 1448 |
| 3 months after treatment | | | | |
| Severe | 30 (1.72%) | 22 (1.28%) | 21 (1.43%) | 16 (1.12%) |
| Moderate | 273 (15.65%) | 266 (15.42%) | 237 (16.13%) | 221 (15.43%) |
| Mild | 458 (26.26%) | 443 (25.68%) | 384 (26.14%) | 364 (25.42%) |
| Few | 429 (24.60%) | 464 (26.90%) | 361 (24.57%) | 392 (27.37%) |
| None | 478 (27.41%) | 467 (27.07%) | 399 (27.16%) | 383 (26.75%) |
| Not medicated by doctors | 76 (4.36%) | 63 (3.65%) | 67 (4.56%) | 56 (3.91%) |
| Total | 1744 | 1725 | 1469 | 1432 |
| 6 months after treatment | | | | |
| ≥4 times per day | 15 (0.86%) | 15 (0.87%) | 6 (0.41%) | 8 (0.57%) |
| 1-3 times per day | 201 (11.53%) | 200 (11.59%) | 160 (11.00%) | 146 (10.36%) |
| ≥3 times per week | 503 (28.84%) | 464 (26.90%) | 421 (28.93%) | 382 (27.11%) |
| 1-2 times per week | 460 (26.38%) | 495 (28.70%) | 393 (27.01%) | 418 (29.67%) |
| <1 time per week | 490 (28.10%) | 476 (27.59%) | 410 (28.18%) | 391 (27.75%) |
| No onset | 75 (4.30%) | 75 (4.35%) | 65 (4.47%) | 64 (4.54%) |
| Total | 1744 | 1725 | 1455 | 1409 |
| 9 months after treatment | | | | |
| ≥4 times per day | 16 (0.92%) | 22 (1.28%) | 7 (0.49%) | 12 (0.87%) |
| 1-3 times per day | 139 (7.97%) | 139 (8.06%) | 96 (6.68%) | 85 (6.13%) |
| ≥3 times per week | 513 (29.42%) | 468 (27.13%) | 424 (29.49%) | 376 (27.13%) |
| 1-2 times per week | 500 (28.67%) | 527 (30.55%) | 432 (30.04%) | 444 (32.03%) |
| <1 time per week | 498 (28.56%) | 490 (28.41%) | 412 (28.65%) | 401 (28.93%) |
| No onset | 78 (4.47%) | 79 (4.58%) | 67 (4.66%) | 68 (4.91%) |
| Total | 1744 | 1725 | 1438 | 1386 |
| 12 months after treatment | | | | |
| ≥4 times per day | 14 (0.80%) | 21 (1.22%) | 4 (0.28%) | 8 (0.58%) |
| 1-3 times per day | 107 (6.14%) | 127 (7.36%) | 59 (4.13%) | 71 (5.19%) |
| ≥3 times per week | 451 (25.86%) | 397 (23.01%) | 362 (25.33%) | 300 (21.91%) |
| 1-2 times per week | 558 (32.00%) | 573 (33.22%) | 486 (34.01%) | 486 (35.50%) |
| <1 time per week | 522 (29.93%) | 525 (30.43%) | 437 (30.58%) | 432 (31.56%) |
| No onset | 92 (5.28%) | 82 (4.75%) | 81 (5.67%) | 72 (5.26%) |
| Total | 1744 | 1725 | 1429 | 1369 |
| Follow-up | | | | |
| ≥4 times per day | 2 (0.14%) | 4 (0.29%) | 2 (0.14%) | 3 (0.22%) |
| 1-3 times per day | 46 (3.17%) | 48 (3.45%) | 45 (3.18%) | 48 (3.54%) |
| ≥3 times per week | 363 (25.03%) | 331 (23.78%) | 355 (25.09%) | 323 (23.82%) |
| 1-2 times per week | 478 (32.97%) | 469 (33.69%) | 465 (32.86%) | 456 (33.63%) |
| <1 time per week | 452 (31.17%) | 445 (31.97%) | 442 (31.24%) | 431 (31.78%) |
| No onset | 109 (7.52%) | 95 (6.82%) | 106 (7.49%) | 95 (7.01%) |
| Total | 1450 | 1392 | 1415 | 1356 |

TABLE 62 test of different observations (5$^{th}$ question)

| Items | Test method | FAS Statistic | FAS P value | PP Statistic | PP P value |
|---|---|---|---|---|---|
| Baseline | Chi-square test | 4.23 | 0.5166 | 3.82 | 0.5754 |
| 1 month after treatment | Chi-square test | 3.53 | 0.6184 | 5.28 | 0.3831 |
| 3 months after treatment | Chi-square test | 4.18 | 0.5234 | 3.89 | 0.5660 |
| 6 months after treatment | Rank-sum test | 0.40 | 0.6867 | 0.62 | 0.5356 |
| 9 months after treatment | Rank-sum test | 0.47 | 0.6408 | 0.92 | 0.3566 |
| 12 months after treatment | Rank-sum test | −0.03 | 0.9779 | 0.49 | 0.6242 |
| Follow-up | Rank-sum test | 0.07 | 0.9404 | 0.10 | 0.9221 |

TABLE 63 different observations (6$^{th}$ question)

| Items | FAS Control group | FAS Trial group | PP Control group | PP Trial group |
|---|---|---|---|---|
| Baseline | | | | |
| Dissatisfied | 20 (1.15%) | 12 (0.70%) | 17 (1.14%) | 12 (0.83%) |
| Mostly dissatisfied | 114 (6.54%) | 104 (6.07%) | 97 (6.48%) | 93 (6.45%) |
| Partly satisfied | 548 (31.46%) | 546 (31.86%) | 497 (33.20%) | 480 (33.29%) |
| Mostly satisfied | 793 (45.52%) | 789 (46.03%) | 663 (44.29%) | 647 (44.87%) |
| Highly satisfied | 267 (15.33%) | 263 (15.34%) | 223 (14.90%) | 210 (14.56%) |
| Total | 1742 | 1714 | 1497 | 1442 |
| 1 month after treatment | | | | |
| Dissatisfied | 8 (0.46%) | 4 (0.23%) | 3 (0.20%) | 3 (0.21%) |
| Mostly dissatisfied | 70 (4.01%) | 69 (4.00%) | 65 (4.37%) | 57 (3.94%) |
| Partly satisfied | 495 (28.38%) | 469 (27.20%) | 442 (29.68%) | 405 (27.97%) |
| Mostly satisfied | 857 (49.14%) | 860 (49.88%) | 713 (47.88%) | 718 (49.59%) |
| Highly consent | 314 (18.00%) | 322 (18.68%) | 266 (17.86%) | 265 (18.30%) |
| Total | 1744 | 1724 | 1489 | 1448 |
| 3 months after treatment | | | | |
| Dissatisfied | 4 (0.23%) | 3 (0.17%) | 1 (0.07%) | 2 (0.14%) |
| Mostly dissatisfied | 46 (2.64%) | 51 (2.96%) | 37 (2.51%) | 41 (2.86%) |
| Partly satisfied | 448 (25.69%) | 410 (23.78%) | 387 (26.29%) | 342 (23.87%) |
| Mostly satisfied | 904 (51.83%) | 905 (52.49%) | 752 (51.09%) | 759 (52.97%) |
| Highly satisfied | 342 (19.61%) | 355 (20.59%) | 295 (20.04%) | 289 (20.17%) |
| Total | 1744 | 1724 | 1472 | 1433 |
| 6 months after treatment | | | | |
| Dissatisfied | 3 (0.17%) | 2 (0.12%) | 0 (0.00%) | 1 (0.07%) |
| Mostly dissatisfied | 34 (1.95%) | 37 (2.15%) | 24 (1.65%) | 21 (1.49%) |
| Partly satisfied | 358 (20.53%) | 360 (20.88%) | 293 (20.14%) | 285 (20.23%) |
| Mostly satisfied | 972 (55.73%) | 941 (54.58%) | 814 (55.95%) | 782 (55.50%) |
| Highly satisfied | 377 (21.62%) | 384 (22.27%) | 324 (22.27%) | 320 (22.71%) |
| Total | 1744 | 1724 | 1455 | 1409 |
| 9 months after treatment | | | | |
| Dissatisfied | 4 (0.23%) | 3 (0.17%) | 1 (0.07%) | 2 (0.14%) |
| Mostly dissatisfied | 34 (1.95%) | 31 (1.80%) | 22 (1.53%) | 13 (0.94%) |
| Partly satisfied | 269 (15.42%) | 284 (16.47%) | 203 (14.10%) | 197 (14.22%) |
| Mostly satisfied | 1025 (58.77%) | 996 (57.77%) | 855 (59.38%) | 825 (59.57%) |
| Highly satisfied | 412 (23.62%) | 410 (23.78%) | 359 (24.93%) | 348 (25.13%) |
| Total | 1744 | 1724 | 1440 | 1385 |
| 12 months after treatment | | | | |
| Dissatisfied | 5 (0.29%) | 3 (0.17%) | 1 (0.07%) | 0 (0.00%) |
| Mostly dissatisfied | 27 (1.55%) | 27 (1.57%) | 12 (0.84%) | 8 (0.58%) |
| Partly satisfied | 204 (11.70%) | 236 (13.69%) | 137 (9.59%) | 144 (10.53%) |
| Mostly satisfied | 1057 (60.61%) | 1017 (58.99%) | 882 (61.72%) | 842 (61.55%) |
| Highly satisfied | 451 (25.86%) | 441 (25.58%) | 397 (27.78%) | 374 (27.34%) |
| Total | 1744 | 1724 | 1429 | 1368 |

TABLE 63-continued different observations (6$^{th}$ question)

| | FAS | | PP | |
|---|---|---|---|---|
| Items | Control group | Trial group | Control group | Trial group |
| Follow-up | | | | |
| Dissatisfied | 0 (0.00%) | 0 (0.00%) | 0 (0.00%) | 0 (0.00%) |
| Mostly dissatisfied | 9 (0.62%) | 5 (0.36%) | 9 (0.63%) | 5 (0.37%) |
| Partly satisfied | 123 (8.45%) | 136 (9.74%) | 122 (8.59%) | 131 (9.63%) |
| Mostly satisfied | 913 (62.75%) | 845 (60.53%) | 884 (62.25%) | 821 (60.37%) |
| Highly satisfied | 410 (28.18%) | 410 (29.37%) | 405 (28.52%) | 403 (29.63%) |
| Total | 1455 | 1396 | 1420 | 1360 |

TABLE 64 test of different observations (6$^{th}$ question)

| | | FAS | | PP | |
|---|---|---|---|---|---|
| Items | Test method | Statistic | P value | Statistic | P value |
| Baseline | Rank-sum test | 0.44 | 0.6613 | 0.07 | 0.9403 |
| 1 month after treatment | Rank-sum test | 0.91 | 0.3654 | 1.06 | 0.2889 |
| 3 months after treatment | Rank-sum test | 1.06 | 0.2890 | 0.78 | 0.4379 |
| 6 months after treatment | Rank-sum test | 0.06 | 0.9548 | 0.19 | 0.8514 |
| 9 months after treatment | Rank-sum test | −0.26 | 0.7923 | 0.28 | 0.7817 |
| 12 months after treatment | Rank-sum test | −0.93 | 0.3518 | −0.42 | 0.6713 |
| Follow-up | Rank-sum test | 0.20 | 0.8407 | 0.26 | 0.7977 |

TABLE 65 different observations (7$^{th}$ question)

| | FAS | | PP | |
|---|---|---|---|---|
| Items | Control group | Trial group | Control group | Trial group |
| Baseline | | | | |
| Dissatisfied | 7 (0.40%) | 2 (0.12%) | 5 (0.33%) | 2 (0.14%) |
| Mostly dissatisfied | 80 (4.60%) | 78 (4.55%) | 73 (4.88%) | 72 (5.00%) |
| Partly satisfied | 463 (26.61%) | 447 (26.09%) | 418 (27.94%) | 396 (27.48%) |
| Mostly satisfied | 835 (47.99%) | 840 (49.04%) | 696 (46.52%) | 696 (48.30%) |
| Highly satisfied | 355 (20.40%) | 346 (20.20%) | 304 (20.32%) | 275 (19.08%) |
| Total | 1740 | 1713 | 1496 | 1441 |
| 1 month after treatment | | | | |
| Dissatisfied | 3 (0.17%) | 1 (0.06%) | 2 (0.13%) | 1 (0.07%) |
| Mostly dissatisfied | 54 (3.10%) | 55 (3.20%) | 50 (3.36%) | 49 (3.39%) |
| Partly satisfied | 409 (23.48%) | 389 (22.60%) | 363 (24.41%) | 336 (23.25%) |
| Mostly satisfied | 870 (49.94%) | 878 (51.02%) | 724 (48.69%) | 738 (51.07%) |
| Highly satisfied | 406 (23.31%) | 398 (23.13%) | 348 (23.40%) | 321 (22.21%) |
| Total | 1742 | 1721 | 1487 | 1445 |
| 3 months after treatment | | | | |
| Dissatisfied | 2 (0.11%) | 2 (0.12%) | 1 (0.07%) | 2 (0.14%) |
| Mostly dissatisfied | 34 (1.95%) | 38 (2.21%) | 27 (1.84%) | 33 (2.31%) |
| Partly satisfied | 369 (21.18%) | 344 (19.99%) | 317 (21.56%) | 286 (20.00%) |
| Mostly satisfied | 942 (54.08%) | 919 (53.40%) | 786 (53.47%) | 765 (53.50%) |
| Highly satisfied | 395 (22.68%) | 418 (24.29%) | 339 (23.06%) | 344 (24.06%) |
| Total | 1742 | 1721 | 1470 | 1430 |
| 6 months after treatment | | | | |
| Dissatisfied | 2 (0.11%) | 0 (0.00%) | 1 (0.07%) | 0 (0.00%) |
| Mostly dissatisfied | 23 (1.32%) | 21 (1.22%) | 16 (1.10%) | 15 (1.07%) |
| Partly satisfied | 267 (15.33%) | 269 (15.63%) | 217 (14.93%) | 206 (14.66%) |
| Mostly satisfied | 1014 (58.21%) | 1005 (58.40%) | 846 (58.22%) | 833 (59.29%) |
| Highly satisfied | 436 (25.03%) | 426 (24.75%) | 373 (25.67%) | 351 (24.98%) |
| Total | 1742 | 1721 | 1453 | 1405 |

TABLE 65-continued different observations (7$^{th}$ question)

| Items | FAS | | PP | |
|---|---|---|---|---|
| | Control group | Trial group | Control group | Trial group |
| 9 months after treatment | | | | |
| Dissatisfied | 2 (0.11%) | 0 (0.00%) | 1 (0.07%) | 0 (0.00%) |
| Most dissatisfied | 19 (1.09%) | 15 (0.87%) | 12 (0.83%) | 8 (0.58%) |
| Partly satisfied | 210 (12.06%) | 210 (12.20%) | 157 (10.92%) | 139 (10.06%) |
| Mostly satisfied | 1037 (59.53%) | 1043 (60.60%) | 859 (59.74%) | 855 (61.87%) |
| Highly satisfied | 474 (27.21%) | 453 (26.32%) | 409 (28.44%) | 380 (27.50%) |
| Total | 1742 | 1721 | 1438 | 1382 |
| 12 months after treatment | | | | |
| Dissatisfied | 2 (0.11%) | 0 (0.00%) | 1 (0.07%) | 0 (0.00%) |
| Mostly dissatisfied | 13 (0.75%) | 15 (0.87%) | 4 (0.28%) | 7 (0.51%) |
| Partly satisfied | 170 (9.76%) | 171 (9.94%) | 115 (8.06%) | 98 (7.17%) |
| Mostly satisfied | 1042 (59.82%) | 1041 (60.49%) | 861 (60.34%) | 845 (61.86%) |
| Highly satisfied | 515 (29.56%) | 494 (28.70%) | 446 (31.25%) | 416 (30.45%) |
| Total | 1742 | 1721 | 1427 | 1366 |
| Follow-up | | | | |
| Dissatisfied | 0 (0.00%) | 0 (0.00%) | 0 (0.00%) | 0 (0.00%) |
| Mostly dissatisfied | 4 (0.28%) | 4 (0.29%) | 4 (0.28%) | 4 (0.29%) |
| Partly satisfied | 97 (6.68%) | 109 (7.82%) | 97 (6.84%) | 104 (7.66%) |
| Mostly satisfied | 908 (62.49%) | 823 (59.08%) | 881 (62.13%) | 800 (58.95%) |
| Highly satisfied | 444 (30.56%) | 457 (32.81%) | 436 (30.75%) | 449 (33.09%) |
| Total | 1453 | 1393 | 1418 | 1357 |

TABLE 66 test of different observations (7$^{th}$ question)

| Items | Test method | FAS | | PP | |
|---|---|---|---|---|---|
| | | Statistic | P value | Statistic | P value |
| Baseline | Rank-sum test | 0.33 | 0.7387 | −0.20 | 0.8442 |
| 1 month after treatment | Rank-sum test | 0.29 | 0.7680 | 0.02 | 0.9879 |
| 3 months after treatment | Rank-sum test | 1.06 | 0.2902 | 0.72 | 0.4725 |
| 6 months after treatment | Rank-sum test | −0.15 | 0.8824 | −0.15 | 0.8806 |
| 9 months after treatment | Rank-sum test | −0.35 | 0.7300 | 0.02 | 0.9822 |
| 12 months after treatment | Rank-sum test | −0.53 | 0.5985 | −0.13 | 0.8935 |
| Follow-up | Rank-sum test | 0.69 | 0.4897 | 0.84 | 0.3991 |

TABLE 67 different observations (8$^{th}$ question)

| Items | FAS | | PP | |
|---|---|---|---|---|
| | Control group | Trial group | Control group | Trial group |
| Baseline | | | | |
| Dissatisfied | 16 (0.92%) | 9 (0.53%) | 13 (0.87%) | 8 (0.56%) |
| Mostly dissatisfied | 114 (6.55%) | 101 (5.90%) | 99 (6.61%) | 94 (6.52%) |
| Partly satisfied | 538 (30.90%) | 542 (31.64%) | 487 (32.53%) | 466 (32.34%) |
| Mostly satisfied | 801 (46.01%) | 809 (47.23%) | 676 (45.16%) | 673 (46.70%) |
| Highly satisfied | 272 (15.62%) | 252 (14.71%) | 222 (14.83%) | 200 (13.88%) |
| Total | 1741 | 1713 | 1497 | 1441 |
| 1 month after treatment | | | | |
| Dissatisfied | 6 (0.34%) | 5 (0.29%) | 2 (0.13%) | 4 (0.28%) |
| Mostly dissatisfied | 71 (4.07%) | 65 (3.77%) | 63 (4.23%) | 54 (3.73%) |
| Partly satisfied | 487 (27.92%) | 472 (27.39%) | 435 (29.23%) | 402 (27.78%) |
| Mostly satisfied | 877 (50.29%) | 876 (50.84%) | 729 (48.99%) | 738 (51.00%) |
| Highly satisfied | 303 (17.37%) | 305 (17.70%) | 259 (17.41%) | 249 (17.21%) |
| Total | 1744 | 1723 | 1488 | 1447 |

TABLE 67-continued different observations (8th question)

| | FAS | | PP | |
|---|---|---|---|---|
| Items | Control group | Trial group | Control group | Trial group |
| 3 months after treatment | | | | |
| Dissatisfied | 3 (0.17%) | 4 (0.23%) | 1 (0.07%) | 3 (0.21%) |
| Mostly dissatisfied | 54 (3.10%) | 57 (3.31%) | 42 (2.85%) | 43 (3.01%) |
| Partly satisfied | 433 (24.83%) | 409 (23.72%) | 373 (25.34%) | 338 (23.64%) |
| Mostly satisfied | 921 (52.81%) | 910 (52.78%) | 770 (52.31%) | 764 (53.43%) |
| Highly satisfied | 333 (19.09%) | 344 (19.95%) | 286 (19.43%) | 282 (19.72%) |
| Total | 1744 | 1724 | 1472 | 1430 |
| 6 months after treatment | | | | |
| Dissatisfied | 3 (0.17%) | 6 (0.35%) | 1 (0.07%) | 3 (0.21%) |
| Mostly satisfied | 39 (2.24%) | 38 (2.20%) | 23 (1.58%) | 21 (1.49%) |
| Partly satisfied | 361 (20.70%) | 365 (21.17%) | 305 (20.96%) | 286 (20.34%) |
| Mostly satisfied | 987 (56.59%) | 950 (55.10%) | 825 (56.70%) | 792 (56.33%) |
| Highly satisfied | 354 (20.30%) | 365 (21.17%) | 301 (20.69%) | 304 (21.62%) |
| Total | 1744 | 1724 | 1455 | 1406 |
| 9 months after treatment | | | | |
| Dissatisfied | 6 (0.34%) | 6 (0.35%) | 4 (0.28%) | 2 (0.14%) |
| Mostly dissatisfied | 33 (1.89%) | 36 (2.09%) | 17 (1.18%) | 19 (1.37%) |
| Partly satisfied | 298 (17.09%) | 274 (15.89%) | 239 (16.59%) | 183 (13.23%) |
| Mostly satisfied | 1017 (58.31%) | 1027 (59.57%) | 847 (58.78%) | 858 (62.04%) |
| Highly satisfied | 390 (22.36%) | 381 (22.10%) | 334 (23.18%) | 321 (23.21%) |
| Total | 1744 | 1724 | 1441 | 1383 |
| 12 months after treatment | | | | |
| Dissatisfied | 5 (0.29%) | 5 (0.29%) | 0 (0.00%) | 0 (0.00%) |
| Mostly dissatisfied | 35 (2.01%) | 40 (2.32%) | 18 (1.26%) | 22 (1.61%) |
| Partly satisfied | 215 (12.33%) | 235 (13.63%) | 154 (10.78%) | 141 (10.31%) |
| Mostly satisfied | 1048 (60.09%) | 1014 (58.82%) | 874 (61.16%) | 838 (61.26%) |
| Highly satisfied | 441 (25.29%) | 430 (24.94%) | 383 (26.80%) | 367 (26.83%) |
| Total | 1744 | 1724 | 1429 | 1368 |
| Follow-up | | | | |
| Dissatisfied | 1 (0.07%) | 1 (0.07%) | 1 (0.07%) | 1 (0.07%) |
| Mostly dissatisfied | 9 (0.62%) | 9 (0.65%) | 9 (0.64%) | 9 (0.66%) |
| Partly satisfied | 155 (10.67%) | 137 (9.82%) | 154 (10.87%) | 133 (9.79%) |
| Mostly satisfied | 880 (60.61%) | 842 (60.36%) | 854 (60.27%) | 819 (60.26%) |
| Highly satisfied | 407 (28.03%) | 406 (29.10%) | 399 (28.16%) | 397 (29.21%) |
| Total | 1452 | 1395 | 1417 | 1359 |

TABLE 68 test of different observations (8th question)

| | | FAS | | PP | |
|---|---|---|---|---|---|
| Items | Test method | Statistic | P value | Statistic | P value |
| Baseline | Rank-sum test | 0.05 | 0.9587 | 0.04 | 0.9701 |
| 1 month after treatment | Rank-sum test | 0.57 | 0.5686 | 0.71 | 0.4753 |
| 3 months after treatment | Rank-sum test | 0.66 | 0.5063 | 0.62 | 0.5342 |
| 6 months after treatment | Rank-sum test | 0.09 | 0.9285 | 0.59 | 0.5535 |
| 9 months after treatment | Rank-sum test | 0.29 | 0.7730 | 1.32 | 0.1885 |
| 12 months after treatment | Rank-sum test | −0.88 | 0.3799 | 0.04 | 0.9715 |
| Follow-up | Rank-sum test | 0.82 | 0.4136 | 0.88 | 0.3792 |

TABLE 69

| | FAS | | PP | |
|---|---|---|---|---|
| Items | Control group | Trial group | Control group | Trial group |
| Baseline | | | | |
| Severe | 63 (3.62%) | 60 (3.50%) | 50 (3.34%) | 52 (3.60%) |
| Moderate | 468 (26.88%) | 427 (24.90%) | 404 (26.99%) | 371 (25.71%) |
| Mild | 639 (36.70%) | 624 (36.38%) | 554 (37.01%) | 516 (35.76%) |
| Few | 366 (21.02%) | 409 (23.85%) | 313 (20.91%) | 335 (23.22%) |
| Uneffective | 205 (11.77%) | 195 (11.37%) | 176 (11.76%) | 169 (11.71%) |
| Total | 1741 | 1715 | 1497 | 1443 |
| 1 month after treatment | | | | |
| Severe | 39 (2.24%) | 30 (1.74%) | 30 (2.01%) | 24 (1.66%) |
| Moderate | 328 (18.81%) | 309 (17.93%) | 282 (18.94%) | 267 (18.45%) |
| Mild | 629 (36.07%) | 613 (35.58%) | 535 (35.93%) | 513 (35.45%) |
| Few | 467 (26.78%) | 517 (30.01%) | 385 (25.86%) | 429 (29.65%) |
| Uneffective | 281 (16.11%) | 254 (14.74%) | 257 (17.26%) | 214 (14.79%) |
| Total | 1744 | 1723 | 1489 | 1447 |
| 3 months after treatment | | | | |
| Severe | 26 (1.49%) | 20 (1.16%) | 14 (0.95%) | 14 (0.98%) |
| Moderate | 272 (15.60%) | 264 (15.32%) | 228 (15.51%) | 220 (15.36%) |
| Mild | 585 (33.54%) | 586 (34.01%) | 485 (32.99%) | 475 (33.17%) |
| Few | 556 (31.88%) | 573 (33.26%) | 464 (31.56%) | 480 (33.52%) |
| Uneffective | 305 (17.49%) | 280 (16.25%) | 279 (18.98%) | 243 (16.97%) |
| Total | 1744 | 1723 | 1470 | 1432 |
| 6 months after treatment | | | | |
| Severe | 15 (0.86%) | 18 (1.04%) | 3 (0.21%) | 9 (0.64%) |
| Moderate | 203 (11.64%) | 213 (12.35%) | 153 (10.54%) | 161 (11.43%) |
| Mild | 604 (34.63%) | 583 (33.82%) | 500 (34.44%) | 480 (34.09%) |
| Few | 606 (34.75%) | 604 (35.03%) | 508 (34.99%) | 497 (35.30%) |
| Uneffective | 316 (18.12%) | 306 (17.75%) | 288 (19.83%) | 261 (18.54%) |
| Total | 1744 | 1724 | 1452 | 1408 |
| 9 months after treatment | | | | |
| Severe | 17 (0.97%) | 17 (0.99%) | 5 (0.35%) | 4 (0.29%) |
| Moderate | 153 (8.77%) | 161 (9.34%) | 101 (7.01%) | 109 (7.88%) |
| Mild | 577 (33.08%) | 573 (33.24%) | 472 (32.78%) | 454 (32.83%) |
| Few | 659 (37.79%) | 652 (37.82%) | 556 (38.61%) | 535 (38.68%) |
| Uneffective | 338 (19.38%) | 321 (18.62%) | 306 (21.25%) | 281 (20.32%) |
| Total | 1744 | 1724 | 1440 | 1383 |
| 12 months after treatment | | | | |
| Severe | 17 (0.97%) | 18 (1.04%) | 3 (0.21%) | 3 (0.22%) |
| Moderate | 119 (6.82%) | 145 (8.41%) | 64 (4.48%) | 89 (6.51%) |
| Mild | 533 (30.56%) | 487 (28.25%) | 423 (29.64%) | 367 (26.83%) |
| Few | 693 (39.74%) | 706 (40.95%) | 591 (41.42%) | 588 (42.98%) |
| Uneffective | 382 (21.90%) | 368 (21.35%) | 346 (24.25%) | 321 (23.46%) |
| Total | 1744 | 1724 | 1427 | 1368 |
| Follow-up | | | | |
| Severe | 2 (0.14%) | 2 (0.14%) | 2 (0.14%) | 2 (0.15%) |
| Moderate | 55 (3.78%) | 66 (4.73%) | 55 (3.87%) | 65 (4.78%) |
| Mild | 397 (27.29%) | 361 (25.86%) | 388 (27.32%) | 353 (25.97%) |
| Few | 644 (44.26%) | 599 (42.91%) | 628 (44.23%) | 588 (43.27%) |
| Uneffective | 357 (24.54%) | 368 (26.36%) | 347 (24.44%) | 351 (25.83%) |
| Total | 1455 | 1396 | 1420 | 1359 |

TABLE 70 test of different observations (9$^{th}$ question)

| Items | Test method | FAS Statistic | FAS P value | PP Statistic | PP P value |
|---|---|---|---|---|---|
| Baseline | Rank-sum test | 1.40 | 0.1616 | 0.91 | 0.3620 |
| 1 month after treatment | Rank-sum test | 0.76 | 0.4460 | 0.14 | 0.8882 |
| 3 months after treatment | Rank-sum test | −0.09 | 0.9289 | −0.48 | 0.6278 |
| 6 months after treatment | Rank-sum test | −0.37 | 0.7115 | −0.99 | 0.3215 |
| 9 months after treatment | Rank-sum test | −0.64 | 0.5213 | −0.72 | 0.4698 |
| 12 months after treatment | Rank-sum test | −0.27 | 0.7852 | −0.31 | 0.7529 |
| Follow-up | Rank-sum test | 0.64 | 0.5233 | 0.48 | 0.6342 |

TABLE 71 different observations (10$^{th}$ question)

| Items | FAS Control group | FAS Trial group | PP Control group | PP Trial group |
|---|---|---|---|---|
| Baseline | | | | |
| Dissatisfied | 451 (25.90%) | 416 (s24.21%) | 378 (25.25%) | 343 (23.74%) |
| Mostly dissatisfied | 413 (23.72%) | 454 (26.43%) | 361 (24.11%) | 398 (27.54%) |
| Partly satisfied | 543 (31.19%) | 509 (29.63%) | 483 (32.26%) | 434 (30.03%) |
| Mostly satisfied | 294 (16.89%) | 304 (17.69%) | 244 (16.30%) | 242 (16.75%) |
| Highly satisfied | 40 (2.30%) | 35 (2.04%) | 31 (2.07%) | 28 (1.94%) |
| Total | 1741 | 1718 | 1497 | 1445 |
| 1 month after treatment | | | | |
| Dissatisfied | 396 (22.71%) | 390 (22.62%) | 331 (22.24%) | 326 (22.58%) |
| Mostly dissatisfied | 400 (22.94%) | 384 (22.27%) | 344 (23.12%) | 327 (22.65%) |
| Partly satisfied | 516 (29.59%) | 498 (28.89%) | 455 (30.58%) | 415 (28.74%) |
| Mostly satisfied | 361 (20.70%) | 376 (21.81%) | 295 (19.83%) | 312 (21.61%) |
| Highly satisfied | 71 (4.07%) | 76 (4.41%) | 63 (4.23%) | 64 (4.43%) |
| Total | 1744 | 1724 | 1488 | 1444 |
| 3 months after treatment | | | | |
| Dissatisfied | 372 (21.33%) | 373 (21.64%) | 307 (20.88%) | 306 (21.37%) |
| Mostly dissatisfied | 387 (22.19%) | 375 (21.75%) | 329 (22.38%) | 313 (21.86%) |
| Partly satisfied | 481 (27.58%) | 464 (26.91%) | 417 (28.37%) | 387 (27.03%) |
| Mostly satisfied | 422 (24.20%) | 425 (24.65%) | 345 (23.47%) | 350 (24.44%) |
| Highly satisfied | 82 (4.70%) | 87 (5.05%) | 72 (4.90%) | 76 (5.31%) |
| Total | 1744 | 1724 | 1470 | 1432 |
| 6 months after treatment | | | | |
| Dissatisfied | 364 (20.87%) | 353 (20.48%) | 296 (20.36%) | 279 (19.82%) |
| Mostly dissatisfied | 376 (21.56%) | 379 (21.98%) | 310 (21.32%) | 313 (22.23%) |
| Partly satisfied | 459 (26.32%) | 450 (26.10%) | 394 (27.10%) | 369 (26.21%) |
| Mostly satisfied | 464 (26.61%) | 458 (26.57%) | 383 (26.34%) | 375 (26.63%) |
| Highly satisfied | 81 (4.64%) | 84 (4.87%) | 71 (4.88%) | 72 (5.11%) |
| Total | 1744 | 1724 | 1454 | 1408 |
| 9 months after treatment | | | | |
| Dissatisfied | 341 (19.55%) | 342 (19.84%) | 271 (18.81%) | 263 (18.99%) |
| Mostly dissatisfied | 357 (20.47%) | 341 (19.78%) | 288 (19.99%) | 271 (19.57%) |
| Partly satisfied | 443 (25.40%) | 442 (25.64%) | 372 (25.82%) | 353 (25.49%) |
| Mostly satisfied | 503 (28.84%) | 499 (28.94%) | 421 (29.22%) | 407 (29.39%) |
| Highly satisfied | 100 (5.73%) | 100 (5.80%) | 89 (6.18%) | 91 (6.57%) |
| Total | 1744 | 1724 | 1441 | 1385 |
| 12 months after treatment | | | | |
| Dissatisfied | 340 (19.50%) | 354 (20.53%) | 267 (18.68%) | 274 (20.01%) |
| Mostly dissatisfied | 335 (19.21%) | 328 (19.03%) | 266 (18.61%) | 253 (18.48%) |
| Partly dissatisfied | 399 (22.88%) | 372 (21.58%) | 323 (22.60%) | 277 (20.23%) |
| Mostly satisfied | 538 (30.85%) | 549 (31.84%) | 455 (31.84%) | 457 (33.38%) |
| Highly satisfied | 132 (7.57%) | 121 (7.02%) | 118 (8.26%) | 108 (7.89%) |
| Total | 1744 | 1724 | 1429 | 1369 |

TABLE 71-continued different observations (10$^{th}$ question)

| Items | FAS | | PP | |
|---|---|---|---|---|
| | Control group | Trial group | Control group | Trial group |
| Follow-up | | | | |
| Dissatisfied | 269 (18.50%) | 268 (19.20%) | 257 (18.11%) | 257 (18.90%) |
| Mostly dissatisfied | 277 (19.05%) | 236 (16.91%) | 275 (19.38%) | 231 (16.99%) |
| Partly satisfied | 302 (20.77%) | 288 (20.63%) | 295 (20.79%) | 284 (20.88%) |
| Mostly satisfied | 467 (32.12%) | 472 (33.81%) | 457 (32.21%) | 460 (33.82%) |
| Highly satisfied | 139 (9.56%) | 132 (9.46%) | 135 (9.51%) | 128 (9.41%) |
| Total | 1454 | 1396 | 1419 | 1360 |

TABLE 72 test of different observations (10$^{th}$ question)

| Items | Test method | FAS | | PP | |
|---|---|---|---|---|---|
| | | Statistic | P value | Statistic | P value |
| Baseline | Rank-sum test | 0.26 | 0.7940 | −0.10 | 0.9211 |
| 1 month after treatment | Rank-sum test | 0.65 | 0.5140 | 0.47 | 0.6390 |
| 3 months after treatment | Rank-sum test | 0.23 | 0.8147 | 0.31 | 0.7579 |
| 6 months after treatment | Rank-sum test | 0.17 | 0.8644 | 0.19 | 0.8489 |
| 9 months after treatment | Rank-sum test | 0.10 | 0.9219 | 0.23 | 0.8173 |
| 12 months after treatment | Rank-sum test | −0.39 | 0.7000 | −0.24 | 0.8140 |
| Follow-up | Rank-sum test | 0.53 | 0.5966 | 0.52 | 0.6009 |

TABLE 73 different observations (11$^{th}$ question)

| Items | FAS | | PP | |
|---|---|---|---|---|
| | Control group | Trial group | Control group | Trial group |
| Baseline | | | | |
| Continuously worried | 167 (9.59%) | 144 (8.38%) | 138 (9.21%) | 120 (8.30%) |
| Often worried | 416 (23.88%) | 421 (24.51%) | 376 (25.10%) | 364 (25.19%) |
| Occasionally worried | 713 (40.93%) | 720 (41.91%) | 619 (41.32%) | 604 (41.80%) |
| Seldom Worried | 374 (21.47%) | 377 (21.94%) | 306 (20.43%) | 309 (21.38%) |
| No worried | 72 (4.13%) | 56 (3.26%) | 59 (3.94%) | 48 (3.32%) |
| Total | 1742 | 1718 | 1498 | 1445 |
| 1 month after treatment | | | | |
| Continuously worried | 117 (6.71%) | 115 (6.67%) | 90 (6.04%) | 94 (6.50%) |
| Often worried | 365 (20.93%) | 339 (19.66%) | 324 (21.76%) | 290 (20.04%) |
| Occasionally worried | 714 (40.94%) | 694 (40.26%) | 614 (41.24%) | 576 (39.81%) |
| Seldom worried | 466 (26.72%) | 488 (28.31%) | 389 (26.12%) | 412 (28.47%) |
| No worried | 82 (4.70%) | 88 (5.10%) | 72 (4.84%) | 75 (5.18%) |
| Total | 1744 | 1724 | 1489 | 1447 |
| 3 months after treatment | | | | |
| Continuously worried | 94 (5.39%) | 86 (4.99%) | 68 (4.62%) | 66 (4.61%) |
| Often worried | 319 (18.29%) | 306 (17.75%) | 280 (19.03%) | 251 (17.53%) |
| Occasionally worried | 714 (40.94%) | 696 (40.37%) | 610 (41.47%) | 572 (39.94%) |
| Seldom worried | 532 (30.50%) | 544 (31.55%) | 443 (30.12%) | 465 (32.47%) |
| No worried | 85 (4.87%) | 92 (5.34%) | 70 (4.76%) | 78 (5.45%) |
| Total | 1744 | 1724 | 1471 | 1432 |
| 6 months after treatment | | | | |
| Continuously worried | 77 (4.42%) | 60 (3.48%) | 50 (3.44%) | 41 (2.91%) |
| Often worried | 259 (14.85%) | 274 (15.89%) | 212 (14.57%) | 216 (15.33%) |
| Occasionally worried | 727 (41.69%) | 686 (39.79%) | 621 (42.68%) | 555 (39.39%) |
| Seldom worried | 595 (34.12%) | 601 (34.86%) | 502 (34.50%) | 513 (36.41%) |
| No worried | 86 (4.93%) | 103 (5.97%) | 70 (4.81%) | 84 (5.96%) |
| Total | 1744 | 1724 | 1455 | 1409 |

TABLE 73-continued different observations (11$^{th}$ question)

| | FAS | | PP | |
|---|---|---|---|---|
| Items | Control group | Trial group | Control group | Trial group |
| 9 months after treatment | | | | |
| Continuously worried | 60 (3.44%) | 50 (2.90%) | 35 (2.43%) | 29 (2.09%) |
| Often worried | 215 (12.33%) | 209 (12.12%) | 169 (11.73%) | 151 (10.90%) |
| Occasionally worried | 729 (41.80%) | 722 (41.88%) | 611 (42.40%) | 575 (41.52%) |
| Seldom worried | 635 (36.41%) | 634 (36.77%) | 538 (37.34%) | 534 (38.56%) |
| No worried | 105 (6.02%) | 109 (6.32%) | 88 (6.11%) | 96 (6.93%) |
| Total | 1744 | 1724 | 1441 | 1385 |
| 12 months after treatment | | | | |
| Continuously worried | 55 (3.15%) | 48 (2.78%) | 28 (1.96%) | 27 (1.97%) |
| Often worried | 161 (9.23%) | 182 (10.56%) | 114 (7.98%) | 122 (8.91%) |
| Occasionally worried | 708 (40.60%) | 668 (38.75%) | 580 (40.59%) | 512 (37.40%) |
| Seldom worried | 696 (39.91%) | 712 (41.30%) | 601 (42.06%) | 610 (44.56%) |
| No worried | 124 (7.11%) | 114 (6.61%) | 106 (7.42%) | 98 (7.16%) |
| Total | 1744 | 1724 | 1429 | 1369 |
| Follow-up | | | | |
| Continuously worried | 20 (1.38%) | 24 (1.72%) | 19 (1.34%) | 23 (1.69%) |
| Often worried | 98 (6.74%) | 104 (7.45%) | 97 (6.84%) | 103 (7.58%) |
| Occasionally worried | 566 (38.93%) | 527 (37.75%) | 551 (38.83%) | 513 (37.75%) |
| Seldom worried | 642 (44.15%) | 622 (44.56%) | 628 (44.26%) | 605 (44.52%) |
| No worried | 128 (8.80%) | 119 (8.52%) | 124 (8.74%) | 115 (8.46%) |
| Total | 1454 | 1396 | 1419 | 1359 |

TABLE 74 test of different observations (11$^{th}$ question)

| | | FAS | | PP | |
|---|---|---|---|---|---|
| Items | Test method | Statistic | P value | Statistic | P value |
| Baseline | Rank-sum test | 0.16 | 0.8695 | 0.45 | 0.6513 |
| 1 month after treatment | Rank-sum test | 1.23 | 0.2195 | 1.28 | 0.2003 |
| 3 months after treatment | Rank-sum test | 1.02 | 0.3068 | 1.65 | 0.0994 |
| 6 months after treatment | Rank-sum test | 1.02 | 0.3085 | 1.37 | 0.1714 |
| 9 months after treatment | Rank-sum test | 0.62 | 0.5353 | 1.31 | 0.1886 |
| 12 months after treatment | Rank-sum test | 0.03 | 0.9761 | 0.62 | 0.5325 |
| Follow-up | Rank-sum test | −0.28 | 0.7817 | −0.34 | 0.7341 |

I.7 Safety Evaluation

No severe adverse events were observed.

ILLUSTRATION OF THE DRAWINGS

FIG. 1 was the Kaplan-Meier curve of main endpoint event time (FAS).

FIG. 2 was the Kaplan-Meier curve of main endpoint event time (FAS).

FIG. 3 was the Kaplan-Meier curve of main endpoint event time (PP).

FIG. 4 was the Kaplan-Meier curve of main endpoint event time (PP).

FIG. 5 was the Kaplan-Meier curve of death endpoint event time (FAS).

FIG. 6 was the Kaplan-Meier curve of death endpoint event time (FAS).

FIG. 7 was the Kaplan-Meier curve of death endpoint event time (PP).

FIG. 8 was the Kaplan-Meier curve of death endpoint event time (PP).

EMBODIMENTS

The medicaments of the present invention will be further described with reference to the following examples, which are solely used to illustrate the present invention without limitation.

Example 1

| (1) Formulation | |
|---|---|
| Radix Astragali | 86.5 g |
| Radix Salviae Miltiorrhizae | 21.3 g |
| Radix Notoginseng | 3.5 g |
| Lignum Dalbergiae Odoriferae | 20.6 g |
| Adjuvant PEG-6000 | 30 g |

Extraction of Radix Salvia Miltiorrhizae and Radix Notoginseng:

Coarsely-ground Radix salvia Miltiorrhizae and Radix Notoginseng were placed into an extraction tank, into which water with 7 times the weight of the Radix salvia Miltiorrhizae and Radix Notoginseng crude drugs was poured to decoct for 2 times, 2 hours each time. After combination of the decoction, the solution was filtered and concentrated to obtain an extract in a volume of 900 ml. Then, 95% (v/v) ethanol was slowly added into the obtained extract solution to make a final ethanol content of 70% (v/v), and allowed to stand still for 12~24 hours to separate the supernatant, and the supernatant was filtered. The filtrate was concentrated by removing the ethanol to obtain an extract with a relative density of 1.32~1.38 (50~60° C.).

Extraction of Radix Astragali

Ground Radix Astragali was placed into an extraction tank, into which water with 6 times the weight of the Radix Astragali crude drugs was poured to decoct for 2 times, 2 hours for the first time and 1 hour for the second time. After combination of the decoction, the solution was filtered and concentrated to obtain an extract in a volume of 1500 ml. Then, 95% (v/v) ethanol was slowly added into the obtained extract solution to make a final ethanol content of 60% (v/v), and allowed to stand still for 12~24 hours to separate the supernatant, and the supernatant was concentrated by removing the ethanol to an extract in a volume of about 400 ml. Repeatedly, 95% (v/v) ethanol was slowly added into the obtained extract solution to make a final ethanol content of 80% (v/v), and allowed to stand still for 12~24 hours to separate the supernatant, and the supernatant was concentrated by removing the ethanol to an extract with a relative density of 1.32~1.38 (50~60° C.).

Extraction of Lignum Dalbergiae Odoriferae

The Lignum Dalbergiae Odoriferae was reflux extracted for 5 hours by addition of water with 5 times the weight of the Lignum Dalbergiae Odoriferae crude drugs to collect the volatile oil.

Afore-mentioned Radix salvia Miltiorrhizae and Radix Notoginseng extract, Radix Astragali extract and PEG-6000 were mixed and melted on water bath. Until being well-melted, the volatile oil of Lignum Dalbergiae Odoriferae was added. After homogenized mixing, the mixture was transferred to a dripping machine to give 1000 dripping pills.

Example 2

1000 dripping pills were prepared by the same method as that in EXAMPLE 1, except the formulation:

| | |
|---|---|
| Radix Astragali | 40.6 g |
| Radix salvia Miltiorrhizae | 44.8 g |
| Radix Notoginseng | 11.2 g |
| Lignum Dalbergiae Odoriferae | 38.6 g |
| Adjuvant PEG-6000 | 30 g. |

Example 3

1000 dripping pills were prepared by the same method as that in EXAMPLE 1, except the formulation:

| | |
|---|---|
| Radix Astragali | 77.3 g |
| Radix salvia Miltiorrhizae | 22.8 g |
| Radix Notoginseng | 4.8 g |
| Lignum Dalbergiae Odoriferae | 30.5 g |
| Adjuvant PEG-6000 | 28 g. |

Example 4

1000 dripping pills were prepared by the same method as that in EXAMPLE 1, except the formulation:

| | |
|---|---|
| Radix Astragali | 40.3 g |
| Radix salvia Miltiorrhizae | 39.2 g |
| Radix Notoginseng | 8.2 g |
| Lignum Dalbergiae Odoriferae | 46.8 g |
| Adjuvant PEG-6000 | 25 g. |

Example 5

1000 dripping pills were prepared by the same method as that in EXAMPLE 1, except the formulation:

| | |
|---|---|
| Radix Astragali | 36.5 g |
| Radix salvia Miltiorrhizae | 32.4 g |
| Radix Notoginseng | 6.2 g |
| Lignum Dalbergiae Odoriferae | 41.7 g |
| Adjuvant PEG-6000 | 22 g. |

Example 6

1000 dripping pills were prepared by the same method as that in EXAMPLE 1, except the formulation:

| | |
|---|---|
| Radix Astragali | 65.2 g |
| Radix salvia Miltiorrhizae | 38.9 g |
| Radix Notoginseng | 9.3 g |
| Lignum Dalbergiae Odoriferae | 32.5 g |
| Adjuvant PEG-6000 | 40 g. |

Example 7

1000 dripping pills were prepared by the same method as that in EXAMPLE 1, except the formulation:

| | |
|---|---|
| Radix Astragali | 56.2 g |
| Radix salvia Miltiorrhizae | 32.5 g |
| Radix Notoginseng | 6.2 g |
| Lignum Dalbergiae Odoriferae | 41.6 g |
| Adjuvant PEG-6000 | 22 g. |

Example 8

| Formulation | |
|---|---|
| Radix Astragali | 86.5 g |
| Radix salvia Miltiorrhizae | 21.3 g |
| Radix Notoginseng | 3.5 g |
| Lignum Dalbergiae Odoriferae | 20.6 g |

Extraction method of afore-mentioned crude drug was the same as that in EXAMPLE 1, and the extract, sucrose and dextrin were provided in a ratio of 1:3:1 by weight and prepared into capsule by a conventional method.

Example 9

| Formulation | |
|---|---|
| Radix Astragali | 65.5 g |
| Radix salvia Miltiorrhizae | 25.8 g |
| Radix Notoginseng | 9.5 g |
| Lignum Dalbergiae Odoriferae | 46.4 g |

Extraction method of afore-mentioned crude drug was the same as that in EXAMPLE 1, and the extract, sucrose and dextrin were provided in a ratio of 1:3:1 by weight and prepared into 200 tablets by a conventional method.

Example 10

| Formulation | |
|---|---|
| Radix Astragali | 35.5 g |
| Radix salvia Miltiorrhizae | 50.8 g |
| Radix Notoginseng | 16.3 g |
| Lignum Dalbergiae Odoriferae | 52.3 g |

Extraction method of afore-mentioned crude drug was the same as that in EXAMPLE 1, and the extract, sucrose and dextrin were provided in a ratio of 1:3:1 by weight and prepared into 125 bags of granules by a conventional method.

What is claimed is:

1. A method for secondary prevention of myocardial infarction, said method comprising administrating to a subject in need thereof a Chinese medicine composition prepared from a formulation comprising the crude drugs by the following weight percentage:

| Radix Astragali | 22.2%-66.8%, |
|---|---|
| Radix Salviae Miltiorrhizae | 11.6%-33.4%, |
| Radix Notoginseng | 2.5%-13.5%, and |
| Lignum Dalbergiae Odoriferae | 14.5%-44.3%. |

2. The method according to claim 1, characterized in that said secondary prevention of myocardial infarction is to decrease the occurrence of cardiovascular events in patients after acute myocardial infarction.

3. The method according to claim 2, characterized in that said cardiovascular events include one or more diseases of re-infarction, severe arrhythmia, heart failure, cardiogenic shock and revascularization.

4. The method according to claim 2, characterized in that said Chinese medicine composition is prepared from a formula comprising the crude drugs by weight percentages:

| Radix Astragali | 30.8%-57.2%, |
|---|---|
| Radix Salviae Miltiorrhizae | 15.4%-28.6%, |
| Radix Notoginseng | 3.5%-6.5%, and |
| Lignum Dalbergiae Odoriferae | 20.6%-38.2%. |

5. The method according to claim 1, characterized in that said secondary prevention of myocardial infarction is to decrease the occurrence of non-cardiovascular events in patients after acute myocardial infarction.

6. The method according to claim 5, characterized in that said non-cardiovascular events include one or more diseases of stroke, pulmonary embolism, peripheral vascular events and tumor.

7. The method according to claim 5, characterized in that said Chinese medicine composition is prepared from a formula comprising the crude drugs by weight percentages:

| Radix Astragali | 30.8%-57.2%, |
|---|---|
| Radix Salviae Miltiorrhizae | 15.4%-28.6%, |
| Radix Notoginseng | 3.5%-6.5%, and |
| Lignum Dalbergiae Odoriferae | 20.6%-38.2%. |

8. The method according to claim 1, characterized in that said secondary prevention of myocardial infarction is to decrease the occurrence of death events.

9. The method according to claim 8, characterized in that said death events include one or more diseases of coronary heart disease death, other cardiovascular death and non-cardiovascular disease death.

10. The method according to claim 8, characterized in that said Chinese medicine composition is prepared from a formula comprising the crude drugs by weight percentages:

| Radix Astragali | 44.7%, |
|---|---|
| Radix Salviae Miltiorrhizae | 26.7%, |
| Radix Notoginseng | 6.3%, and |
| Lignum Dalbergiae Odoriferae | 22.3%. |

11. The method according to claim 8, characterized in that said Chinese medicine composition is prepared from a formula comprising the crude drugs by weight percentages:

| Radix Astragali | 41.2%, |
|---|---|
| Radix Salviae Miltiorrhizae | 23.8%, |
| Radix Notoginseng | 4.5%, and |
| Lignum Dalbergiae Odoriferae | 30.5%. |

12. The method according to claim 8, characterized in that said Chinese medicine composition is prepared from a formula comprising the crude drugs by weight percentages:

| Radix Astragali | 30.8%-57.2%, |
|---|---|
| Radix Salviae Miltiorrhizae | 15.4%-28.6%, |
| Radix Notoginseng | 3.5%-6.5%, and |
| Lignum Dalbergiae Odoriferae | 20.6%-38.2%. |

13. The method according to claim 1, characterized in that said secondary prevention of myocardial infarction is to alleviate the attack of angina pectoris in patients after acute myocardial infarction.

14. The method according to claim 13, characterized in that the effect of alleviating the attack of angina pectoris in patients after acute myocardial infarction includes reducing the frequency of attack, shortening the duration, relieving pain degree, decreasing the dose of nitroglycerin and improving one or more symptoms of chest pain, chest tightness, short breath, fatigue, palpitation, spontaneous perspiration as well as pale complexion.

15. The method according to claim 13, characterized in that said Chinese medicine composition is prepared from a formula comprising the crude drugs by weight percentages:

| Radix Astragali | 30.8%-57.2%, |
|---|---|
| Radix Salviae Miltiorrhizae | 15.4%-28.6%, |
| Radix Notoginseng | 3.5%-6.5%, and |
| Lignum Dalbergiae Odoriferae | 20.6%-38.2%. |

16. The method according to claim 1, characterized in that said secondary prevention of myocardial infarction is to improve life quality in patients after acute myocardial infarction.

17. The method according to claim 16, characterized in that the effect of improving life quality in patients after acute myocardial infarction is to ameliorate one or more symptoms of limitation degree of physical activity, steady status of angina pectoris and attack frequency of angina.

18. The method according to claim 16, characterized in that said Chinese medicine composition is prepared from a formula comprising the crude drugs by weight percentages:

| | |
|---|---|
| *Radix* Astragali | 30.8%-57.2%, |
| *Radix* Salviae Miltiorrhizae | 15.4%-28.6%, |
| *Radix Notoginseng* | 3.5%-6.5%, and |
| Lignum Dalbergiae Odoriferae | 20.6%-38.2%. |

19. The method according to claim 1, characterized in that said Chinese medicine composition is prepared from a formula comprising the crude drugs by weight percentages:

| | |
|---|---|
| *Radix* Astragali | 30.8%-57.2%, |
| *Radix* Salviae Miltiorrhizae | 15.4%-28.6%, |
| *Radix Notoginseng* | 3.5%-6.5%, and |
| Lignum Dalbergiae Odoriferae | 20.6%-38.2%. |

\* \* \* \* \*